US005883224A

United States Patent [19]
Kirkpatrick et al.

[11] Patent Number: 5,883,224
[45] Date of Patent: Mar. 16, 1999

[54] CHARACTERIZATION OF TRANSFER FACTORS AND METHODS OF USE

[75] Inventors: Charles H. Kirkpatrick, Denver; Martin J. McDermott; Stephen P. Eisenberg, both of Boulder, all of Colo.

[73] Assignee: Cytokine Sciences, Inc., Denver, Colo.

[21] Appl. No.: 635,062

[22] Filed: Apr. 19, 1996

[51] Int. Cl.$^6$ ............................. A61K 38/08; C07K 7/06
[52] U.S. Cl. ........................................... 530/328; 930/801
[58] Field of Search ................................... 530/328, 329, 530/350; 514/2, 15, 17; 930/801

[56] References Cited

U.S. PATENT DOCUMENTS

| | | |
|---|---|---|
| 3,991,182 | 11/1976 | Spitter . |
| 4,001,080 | 1/1977 | Goust et al. . |
| 4,132,776 | 1/1979 | Jeter . |
| 4,289,690 | 9/1981 | Pestra et al. . |
| 4,435,384 | 3/1984 | Warren . |
| 4,468,379 | 8/1984 | Gottlieb . |
| 4,610,878 | 9/1986 | Wilson et al. . |
| 4,616,079 | 10/1986 | Gottlieb . |
| 4,778,750 | 10/1988 | Gottlieb . |
| 4,816,563 | 3/1989 | Wilson et al. . |
| 5,470,835 | 11/1995 | Kirkpatrick et al. . |

FOREIGN PATENT DOCUMENTS

| | | |
|---|---|---|
| 0 101 200 | 7/1983 | European Pat. Off. . |
| 0 143 445 | 6/1985 | European Pat. Off. . |

OTHER PUBLICATIONS

Kirkpatrick, "Transfer Factor: Perspectives In Human and Veterinary Medicine," J. Exp. Path., vol. 3, No. 4, pp. 383–398 (1987).

Kirkpatrick, et al., "Transfer Factor: Progress Toward Isolation And Chemical Characterization," The Lympokines, pp. 261–274 (The Humana Press 1981).

Petersen, et al., "Selective Removal of Transfer Factor Activity With Antigen," Immunobiology of Transfer Factor, ed. Kirkpatrick, pp. 65–74 (Academic Press, 1983).

Borkowsky, et al., "Deletion Of Antigen–Specific Activity from Leukocyte Dialysates Containing Transfer Factor By Antigen–Coated Polystyrene," J. Immunol., vol. 126, No. 2, pp. 486–489 (1981).

Rozzo et al., "Purification of Transfer Factors," Molecular Immunology, vol. 29, No. 2, pp. 167–182 (1992).

Creighton, Proteins: Structures and Molecular Principles, W.H. Freeman and Company, New York, pp. 25–28 (1984).

Peterson, et al., "Murine Transfer Factor: I. Description of the Model and Evidence for Specificity," J. Immunol., vol. 126, No. 6, pp. 2480–2484 (1981).

Kirkpatrick, et al., "Murine Transfer Factor: II. Transfer of Delayed Hypersensitivity to Synthetic Antigens," J. Immunol., vol. 134, No. 3, pp. 1723–1727 (1985).

Kirkpatrick, et al., "Murine Transfer Factor: III. Specific Interactions Between Transfer Factor and Antigen," J. Immunol., vol. 135, No. 6, pp. 4027–4033 (1985).

Huang, et al., "Nature and Antigen–Specific Activities of Transfer Factor Against Herpes Simplex Virus Type 1.," Acta Virol., vol. 31, pp. 449–457 (1987).

Burger, et al., "Human Transfer Factor: Structural Properties Suggested By HPRP Chromatography and Enzymatic Sensitivities," J. Immunol., vol. 122, No. 3, pp. 1091–1098 (1979).

Rozzo, et al., "Murine Transfer Factor IV. Studies with Genetically Regulated Immune Responses," Cell. Immunol., vol. 115, pp. 130–145 (1988).

Lawrence, et al., "A New Basis for the Immunoregulatory Activities of Transfer Factor—An Arcane Dialect in the Language of Cells," Cell. Immunol., vol. 82, pp. 102–116 (1983).

Borkowsky, et al., "Antigen–Specific Suppressor Factor in Human Leukocyte Dialysates: A Product of Ts Cells Which Bind to Anti–V Region and Anti–Ia Region Antibodies," Immunobiology of Transfer Factor, ed. Kirkpatrick, pp. 91–115 (Academic Press, 1983).

Vandenbark, et al., "Human Transfer Factor: Fractionation By Electrofocusing and High Pressure, Reverse Phase Chromatography," J. Immunol., vol. 118, No. 2, pp. 636–641 (1977).

Wilson, et al., "The Chemical Nature of the Antigen–Specific Moiety of Transfer Factor", Chemical Structure of Transfer Factor, Publication No. 295, Dept. of Basic and Clinical Immunology and Microbiology, Medical University of South Carolina, pp. 239–256.

Sinha, et al., "Immunomodulatory Components Present in IMREG–1, an Experimental Immunosupportive Biologic", Bio/Technology, vol. 6, pp. 810–815 (1988).

Lawrence, et al., "Transfer of Immunologic Information in Humans with Dialysates of Leukocyte Extracts", Department of Medicine, New York University School of Medicine, pp. 84–89.

Kirkpatrick, "Transfer Factor", J. Allergy Clin. Immunol., vol. 81, No. 5, pp. 803–813 (1988).

Steele, et al., "Transfer Factor for the Prevention of Varicella–Zoster Infection in Childhood Leukemia", N. Engl. J. Med., vol. 303, No. 7, pp. 355–359 (1980).

Dwyer, "The Use of Antigen Specific Transfer Factor in the Management of Infection with Herpes Viruses", Immunobiology of Transfer Factor, Academic Press, New York, pp. 233–243 (1983).

Viza, et al., "Orally Administered Specific Transfer Factor for the Treatment of Herpes Infections", Lymphokine Res., vol. 4, No. 1, pp. 27–30 (1985).

(List continued on next page.)

*Primary Examiner*—David Saunders
*Assistant Examiner*—F. Pierre VanderVegt
*Attorney, Agent, or Firm*—Jones & Askew, LLP

[57] ABSTRACT

Characterization of transfer factors is provided in the form of amino acid and nucleic acid sequences corresponding to at least a portion of a conserved transfer factor region. The amino acid and nucleic acid sequences, or functional homologues thereof, are provided along with methods of use thereof for diagnostic, therapeutic and other purposes.

2 Claims, 26 Drawing Sheets

OTHER PUBLICATIONS

McMeeking, et al., "A Controlled Trial of Bovine Dialyzable Leukocyte Extract for Cryptosporidiosis in Patients with AIDS", J. Infect. Dis., vol. 161, pp. 108–112 (1990).

Kirkpatrick, et al., "Treatment of Chronic Mucocutaneous Candidiasis with Transfer Factor", Immune Regulators in Transfer Factor, Academic Press, New York, pp. 547–562 (1979).

Bonnerjea et al., "Protein Purification: The Right Step at the Right Time," Bio/Technology, vol. 4, pp. 955–958 (Nov. 1986).

Dunnick et al., "Specificity and Structural Analysis of a Guinea–Pig Transfer Factor–Like Activity," J. Immunology, vol. 118, No. 6, pp. 1944–1950 (Jun. 1977).

Kirkpatrick et al., "Effect of Transfer Factor on Lymphocyte Function in Anergic Patients," J. Clinical Investigation, vol. 51, pp. 2948–2958 (1972).

Sofer et al., "Designing an Optimal Chromatographic Purification Scheme for Proteins," Biofeature, pp. 198–203 (Nov./Dec. 1983).

Qi, H. Y. et al. "Chemical Characterization of the Purified Component of Specific Transfer Factor in the Leukocyte Dialysates from HSV–1 Immunized Goats" *Acta virol.,* vol. 36, pp. 239–244 (1992).

Biemann, K. "Methods for Protein Sequencing", *Analytical Chemistry,* vol. 58, No. 13, pp. 1289A–1300A (1986).

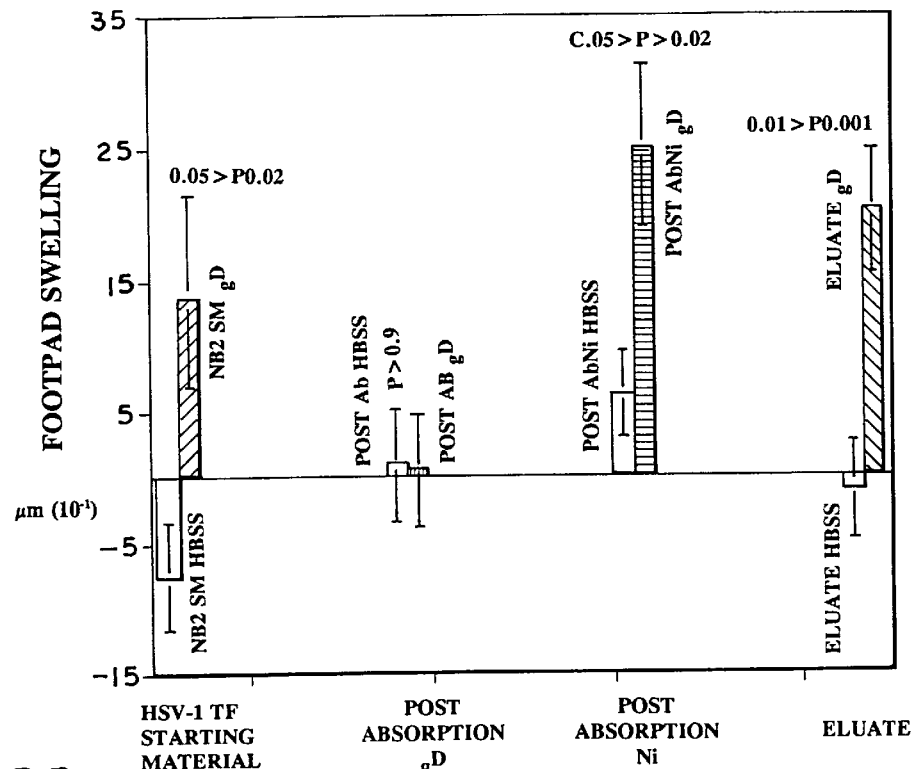
Fig_20
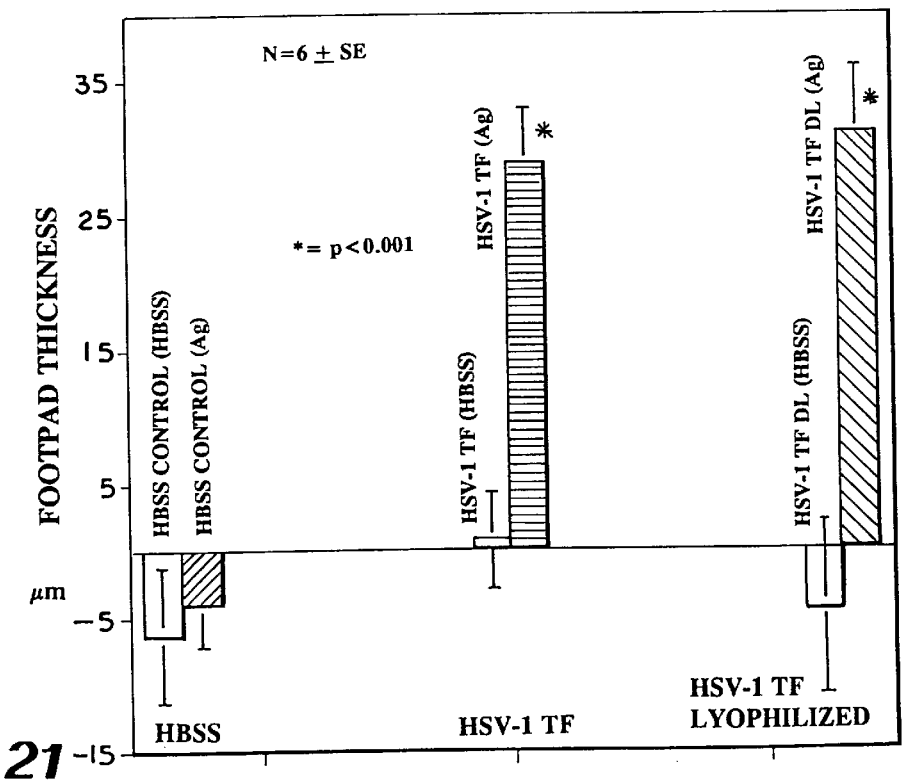
Fig_21

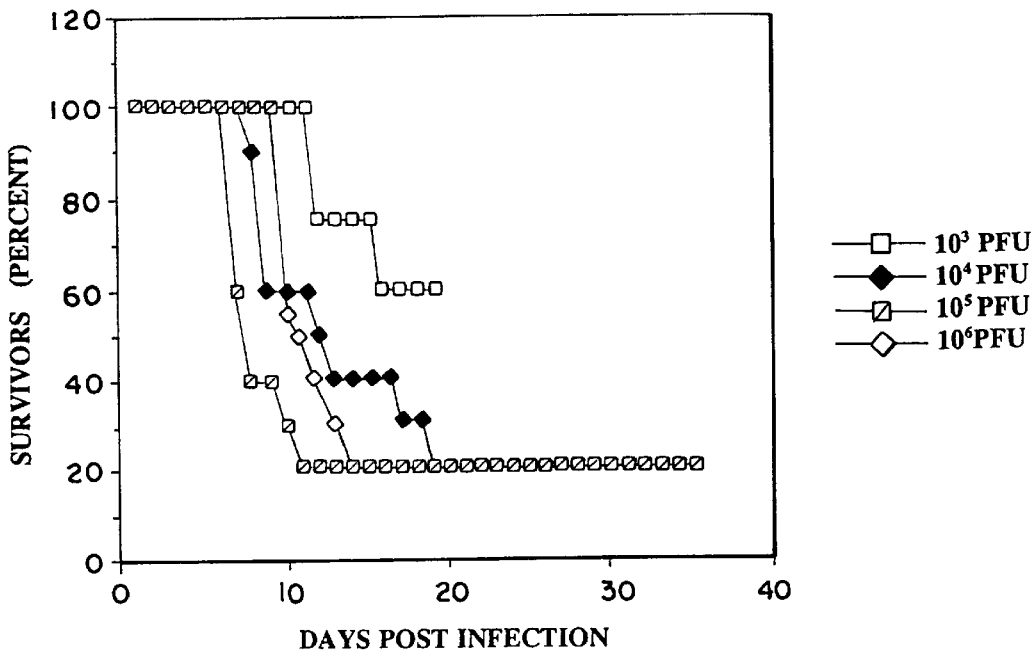
Fig_22
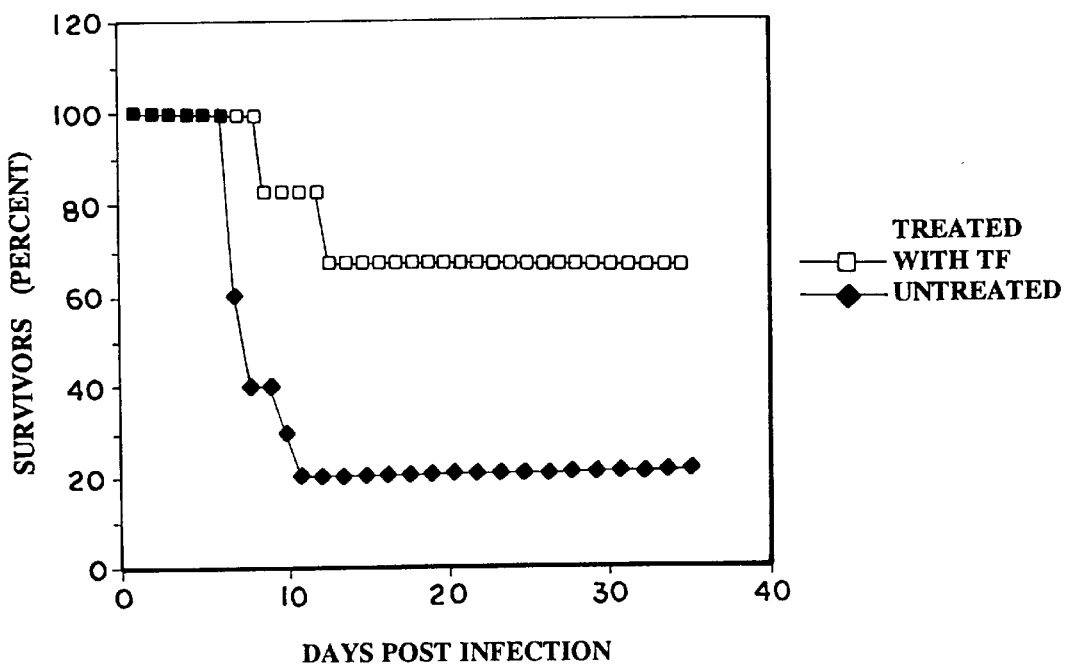
Fig_24

| EVENT | UNTREATED MICE | | | | | | | | | | | | | |
|---|---|---|---|---|---|---|---|---|---|---|---|---|---|---|
| DEATH | | | | | | | | | + | + | + | | | |
| NEURO | | | | | | | | + | + | + | + | | | |
| WEIGHT LOSS | | | | | | | | | + | + | + | | | |
| SATELLITE | | | | | + | + | + | + | + | + | + | | | |
| POCK | | + | + | + | + | + | + | + | + | + | + | | | |
| EDEMA | | + | + | + | + | + | + | + | + | + | + | + | + | + |
| | 1 | 2 | 3 | 4 | 5 | 6 | 7 | 8 | 9 | 10 | 11 | 12 | 13 | 14 |
DAY AFTER INFECTION
UNTREATED MICE
| | | | | | | | | | | | | | | |
|---|---|---|---|---|---|---|---|---|---|---|---|---|---|---|
| DEATH | | | | | | | | | + | + | + | | | |
| NEURO | | | | | | | | + | + | + | + | | | |
| WEIGHT LOSS | | | | | | | | | + | + | + | | | |
| SATELLITE | | | | | | + | + | + | + | + | + | + | | |
| POCK | | + | + | + | + | + | + | + | + | + | + | + | | |
| EDEMA | | + | + | + | + | + | + | + | + | + | + | + | + | + |
| DAY | 1 | 2 | 3 | 4 | 5 | 6 | 7 | 8 | 9 | 10 | 11 | 12 | 13 | 14 |
TREATED MICE
| | | | | | | | | | | | | | | |
|---|---|---|---|---|---|---|---|---|---|---|---|---|---|---|
| EDEMA | | + | + | + | + | | | | | | | | | |
| POCK | | (+) | | | (+) | (+) | (+) | (+) | | | | | | |
| SATELLITE | | | | | | (+) | (+) | (+) | | | | | | |
| WT LOSS | | | | | | | | | | | | | | |
| NEURO | | | | | | | | | (+) | | | | | |
| DEATH | | | | | | | | | (+) | | | | | |

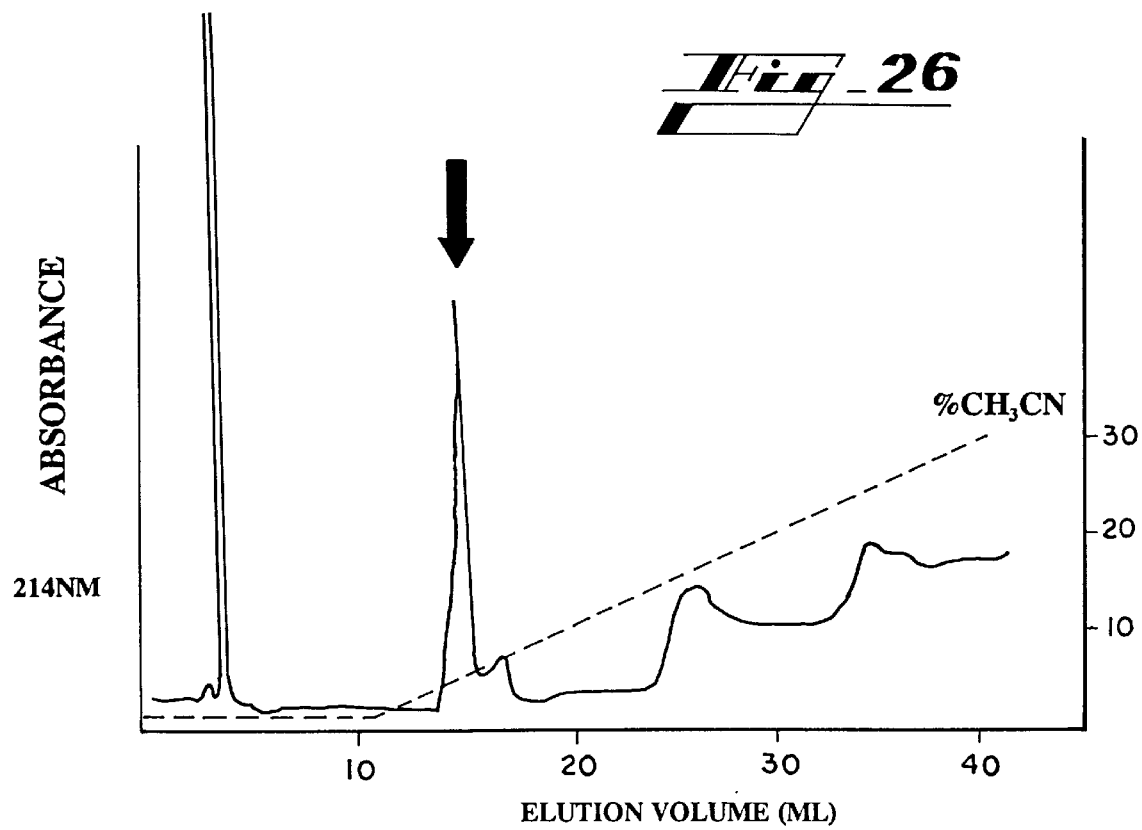
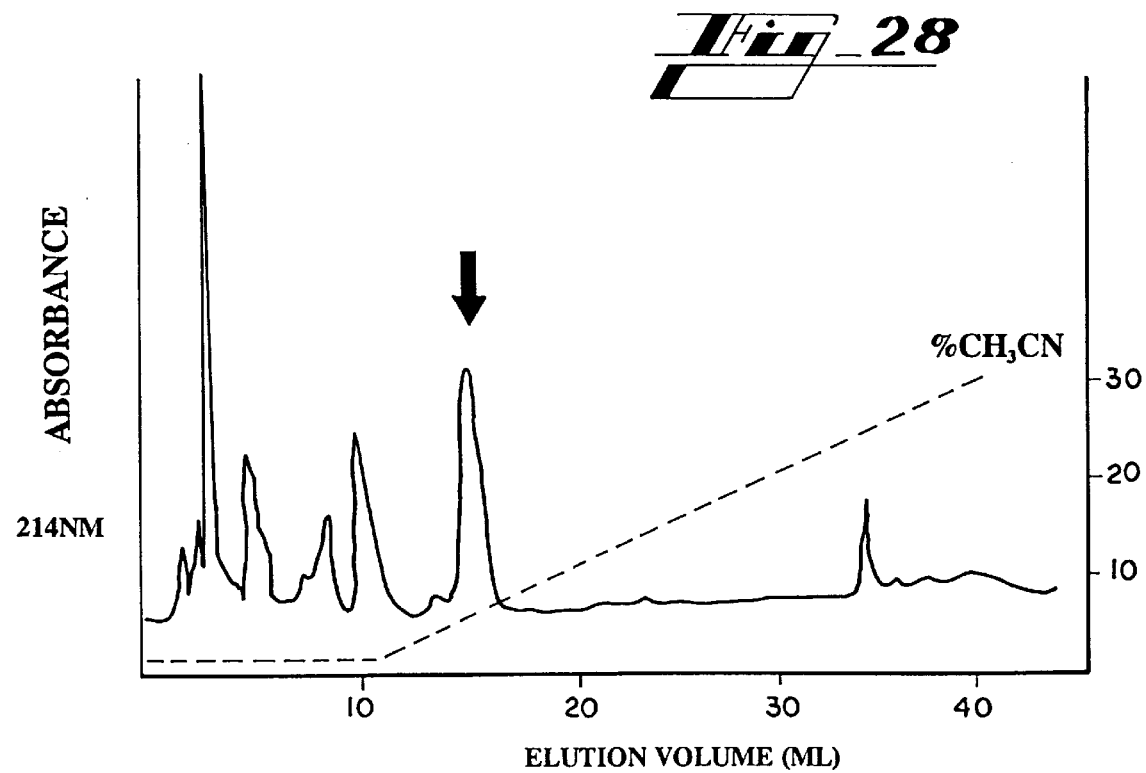

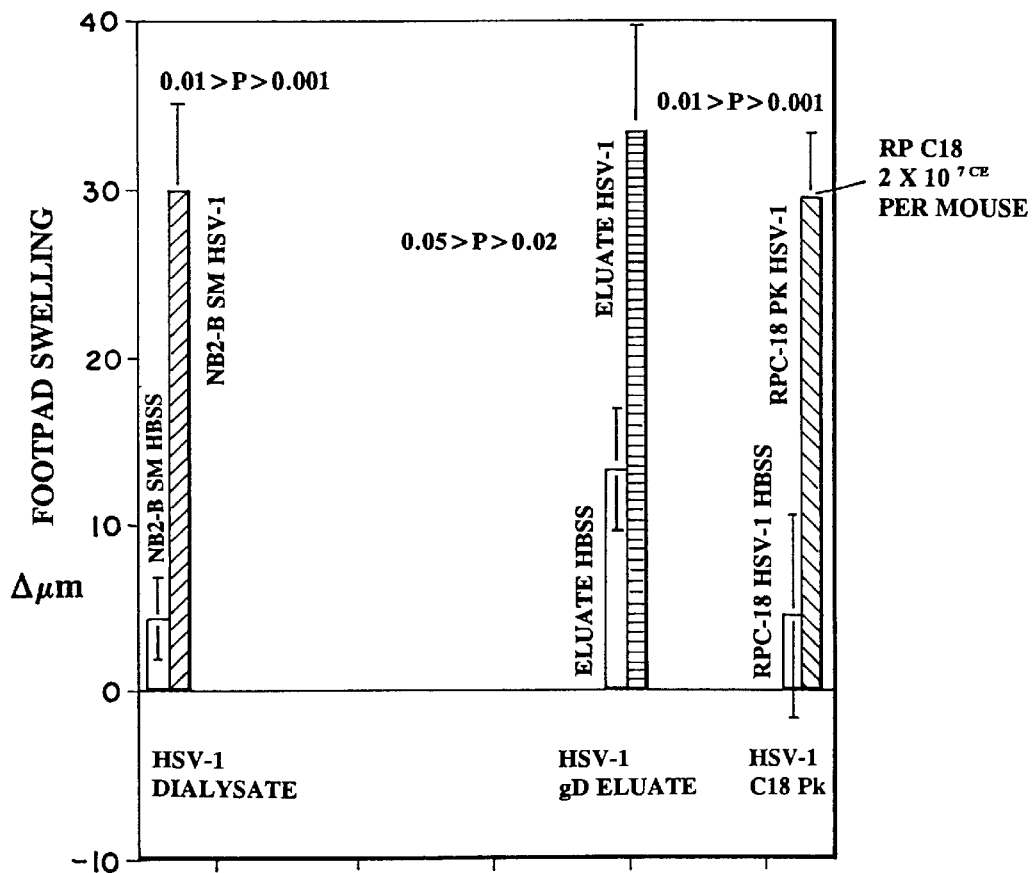
*Fig_27*
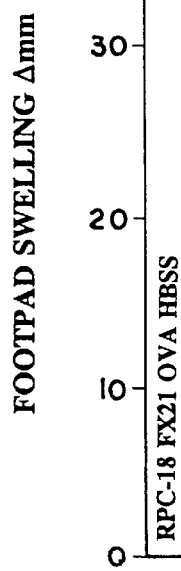
*Fig_31*

CHARACTERIZATION OF TRANSFER FACTORS AND METHODS OF USE

FIELD OF INVENTION

This invention relates to the transfer of cell-mediated immunity by administering transfer factors to a human or animal. More particularly, it relates to processes for obtaining and characterizing transfer factors and methods of using the transfer factors and conserved regions thereof to diagnose, prevent and treat diseases.

BACKGROUND OF THE INVENTION

The terms "antigenic determinant" and "epitope" are defined as the parts of a molecule that can interact specifically with either the cellular or the humoral products associated with the immune response. The term "antigen" is defined as anything that can serve as a target for an immune response. The immune response can be either cellular or humoral. The term "cell mediated immunity" is defined as an immune response mediated by cells rather than by antibody. The term "delayed type hypersensitivity" is defined as a T-lymphocyte-mediated inflammatory response that occurs in close proximity to the site of injection or application of the inciting antigen. It includes, but is not limited to, delayed type hypersensitivity and cytotoxic T cells. A "hapten" is defined herein as a substance that reacts selectively with appropriate antibodies or T cells but the hapten itself is usually not immunogenic. Most haptens are small molecules or small parts of large molecules, but some macromolecules can also function as haptens. The term "antibody" means molecules that also bind antigens, however, they are distinguished from transfer factor in that the molecular weight of antibodies is between approximately 160,000 Daltons and 1,000,000 Daltons.

Transfer factors have been defined as a dialyzable material or family of materials that can be extracted from lymphoid cells of humans and certain other animals and have the capacity to transfer immune responses from one individual to another, even across species. The material is a substance obtained from leukocytes, usually lysed, from humans and other vertebrates that have been sensitized so as to express delayed type hypersensitivity or other cell mediated responses to a sensitizing antigen. Transfer factor binds homologous antigen and has the capacity to mediate transfer of delayed type hypersensitivity and other cell mediated immune responses from one individual to another. In such a situation the individual from whom the transfer factor is obtained has been sensitized to the antigen of interest.

Notwithstanding the above properties, the transfer factors are smaller than antibodies, and do not transfer antibody mediated responses, nor do they induce antibody production.[1,2,3] These properties of transfer factor are also described by Spitler et al. which discusses a "transfer factor" secured from the leukocytes of healthy donors.[4] The material suppresses disease symptoms. Spitler et al. describe the material as being heat stable, and having a molecular weight of less than 20,000 Daltons. It is secured by lysing leukocytes, and then incubating the lysate with $Mg^{+2}$ and DNase, followed by filtration through a Millipore filter.

There have been numerous additional attempts to characterize the substance referred to as transfer factor, these being reported in both the scientific and patent literature. In all of these reports, the transfer factor material was a crude fraction of cell lysate. To the inventors knowledge, no one has characterized a substantially pure transfer factor. See U.S. Pat. No. 5,470,835 to Kirkpatrick et al. for purification of transfer factors. Baram et al fractionated human leukocyte extracts through ion exchange chromatography, using diethylaminoethyl cellulose (DEAE).[5] This work was continued and, as reported by Baram et al., gel filtration and paper chromatography were used to further fractionate human leukocyte extracts.[6] Among the conclusions presented by this work was that transfer factor contained nucleosides. Work by Lawrence et al. using gel filtration chromatography on leukocyte extracts of sensitized humans, led to a proposal that transfer factor is (i) water soluble, (ii) dialyzable, (iii) has a molecular weight of less than 10,000 Daltons, (iv) was resistant to deoxyribonuclease, ribonuclease and trypsin digestion, and (v) possessed a chromatographic peak showing greater absorbance at 260 nm than at 280 nm.[7,8,9] This combination of factors led to a proposal that transfer factor was a small, ribonuclease resistant polyribonucleotide.

Progress toward the molecular characterization of transfer factors has been slow, limited largely by the lack of an adequate purification methodology and the need for quantitative assay methods. It has been shown that molecules having transfer factor activity are relatively small, i.e. less than 6000 Daltons, hydrophilic, and polar in native form. Furthermore, transfer factor activity survives heating at 56° C., but not at 75° C., for 30 minutes, and at least brief exposure to 95% ethanol. Results from enzyme sensitivity and activity depletion studies have produced results compatible with a nucleopeptide or nucleoprotein model for the structure of transfer factors. Caution must be used in interpreting prior art results, however, because impure preparations were studied and quantitative determinations were not performed. Thus, the molecular nature of transfer factors is, as yet, not well understood.

The inclination toward the assumption that a nucleotide or nucleoside was a part of the transfer factor molecule was continued by Gottlieb et al.[10,11,12] Gottlieb differentiated transfer factors from immune modulators (the '379 patent), and amplifiers (the '079 patent). In the Lancet publication, Gottlieb postulated that transfer factor consisted of 12 amino acids and an oligonucleotide. As a result, research focused on the study of eluates at wavelengths of 254 nm or greater. Many reports noted high 254/260 nm to 280 nm absorbance ratios, again suggesting oligonucleotides as part of the transfer factor fraction.[13,14,15,16,17,18,19,20,21] Similarly, Warren hypothesizes a molecule of a molecular weight of from 5000 to 10,000 Daltons containing protein and RNA.[22] Goust et al. describes dialyzable transfer factor as a mixture of molecules of molecular weight generally from 4000 to 7000 Daltons and containing a ribonucleotide.[23] Again, Wilson et al.[24] describes three forms of transfer factor, all of which contain a nucleotide moiety and a peptide moiety. (Note column 11 of this reference.)

The progress that has been made in characterizing the impure transfer factor material is summarized in a review by Kirkpatrick.[25] In that review, the dialyzable material that contains transfer factor activity is described as a polypeptide with a molecular weight of between 4000 and 6000 Daltons and is protease sensitive. The transfer factor material apparently binds specifically to antigen.[26] The review states that the presence of nucleic acids, ribose, and phosphodiester groups has not been ruled out.[27]

Interest in the molecule and its structure has, if anything, increased because of its therapeutic efficacy. Apart from therapeutic uses described by the references set forth above, reference may be made, e.g., to Viza et al.[28] suggesting transfer factor therapy for *Herpes simplex* virus. One also notes Warren[29], describing dermatological efficacy for blemishes, acne, condyloma and HSV. The transfer factor fraction has been shown to be efficacious against *C. albicans*, as shown in Kirkpatrick et al,[30] the disclosure of which is incorporated by reference. Additional showings of efficacy against Herpes simplex may be found.[31,32,33] *Varicella zoster* infection has been prevented with transfer factor.[34] Transfer factor has showed efficacy against cryptosporidiosis in AIDS patients.[35,36] All of these studies were performed with only partially purified transfer factor fractions. No clinical or biochemical studies have been performed to date with substantially pure transfer factor material because of the difficulty in isolating and characterizing pure transfer factor material.

As can be seen by the foregoing review of the literature on transfer factor, the isolation and characterization of a substantially pure transfer factor material has eluded the research community for over thirty years. Despite keen scientific and clinical interests, and after deducing several important physical parameters about the elusive transfer factor material, the actual physical isolation of substantially pure material has not been possible.

What is needed is characterization of transfer factor material. Furthermore, there is a need to provide a conserved amino acid sequence for transfer factors in order to identify, isolate and produce transfer factor either chemically or by recombinant methods. These molecules could then be administered to humans or animals thereby transferring immunity to a specific antigen or epitope. Substantially pure transfer factor could be made to treat already infected humans or animals or could be used to prevent disease. Characterization of transfer factors would be of great benefit to the treatment of disease.

SUMMARY OF THE INVENTION

The present invention provides the characterization of transfer factor, methods of producing purified transfer factor, and methods of diagnosing, preventing and treating various diseases with the purified transfer factor containing a conserved transfer factor region. The invention provides amino acid and nucleic acid sequences encoding for a conserved transfer factor region.

The present invention includes the characterization of transfer factors that are isolated from natural sources or are produced synthetically. Substantially pure or isolated transfer factors or a conserved transfer factor region from either source can be used according to the present invention to diagnose, prevent or treat a wide variety of pathological conditions. For example, a transfer factor or factors that transfer cell mediated immunity against *Herpes simplex* virus can be used either to treat a *Herpes simplex* infection or to protect a human from *Herpes simplex* infection.

The advantages of using transfer factors to impart immunity are many. They include speed of transfer of immunity. Immunity to a specific antigen can be detected in as little as several hours after administration of the transfer factor. This is a vast improvement over conventional immunization which can take weeks or months to impart protection.

Because each unique transfer factor molecule is thought to transfer immunity to a specific antigen or epitope, several different transfer factor molecules specific for different antigens can be admixed to custom design a complex immune response.

In addition, characterization of a conserved transfer factor region provides compositions and methods for diagnosing and treating abnormal immune conditions and for isolating all transfer factors sharing the conserved region.

Accordingly, it is an object of the present invention to characterize transfer factors and in particular a conserved transfer factor region.

It is another object of the present invention to provide a conserved transfer factor region.

It is another object of the present invention to provide an amino acid sequence encoding a conserved transfer factor region.

It is another object of the present invention to provide a nucleic acid encoding a conserved transfer factor region.

It is yet another object of the present invention to provide a conserved transfer factor region that can be administered to a human or animal to elicit a desired immune response.

It is another object of the present invention to provide an oligonucleotide representative of the conserved region of transfer factor for identification of transfer factor encoding genetic material.

It is another object of the present invention to provide a method of recombinantly producing a conserved transfer factor region.

It is another object of the present invention to provide a conserved transfer factor region for treating infectious diseases.

It is another object of the present invention to provide a conserved transfer factor region for protecting against infectious diseases.

It is yet another object of the present invention to provide a means for isolating transfer factors that share a conserved region from one species and transfer immunity to another species.

These and other objects, features and advantages of the present invention will become apparent after a review of the following detailed description of the disclosed embodiment and the appended claims.

BRIEF DESCRIPTION OF THE DRAWINGS

FIG. 20 shows the glycoprotein D affinity purification of HSV-1 transfer factor. The footpad responses (DTH) to HBSS and recombinant glycoprotein D in mice that were treated with the transfer factor-containing ultrafiltrate (HSV-1 specific transfer factor starting material) are shown at the left of the Figure. Note that incubation of the starting material on the gD-Ni-NTA-agarose beads completely removed the transfer factor activity (post-absorption gD), but that incubation of the same material on Ni-NTA-agarose beads without gD did not remove the transfer factor activity (post-absorption Ni). The transfer factor could be recovered from the gD beads by elution.

FIG. 21 shows the effect of bovine HSV-1 transfer factor on DTH response to HSV-1 antigen in mice. The HSV antigen was a suspension of a human clinical isolate that had been rendered non-infectious by ultraviolet irradiation. The control preparation was Hank's balanced saline solution (HBSS) that was also used as the diluent for the HSV-1 antigen. The results are expressed as the change in thickness of the footpad 18–24 hours after the initial measurement and injection of the test materials. Note that control mice that had been injected with HBSS did not develop footpad swelling after injection with the HSV-1 antigen. This activity of the transfer factor was not altered by lyophilization of the sample.

FIG. 22 shows the survival of BALB/c mice after intraperitoneal infection with various doses of infectious *Herpes simplex* Type-1. Each group represents at least 10 mice. The study with mice that were infected with $10^3$ pfu was terminated on day 18.

FIG. 23 shows the clinical course of cutaneous *Herpes simplex* infections in untreated BALB/c mice.

FIG. 24 shows mice that were infected with $10^5$ pfu of *Herpes simplex* virus on day 0. By day 11, 80% of the untreated mice had succumbed. In contrast, only 17% of the transfer factor-treated mice died of *Herpes simplex* infections by day 11, and 67% of mice survived the infections.

FIG. 25 is a comparison of the clinical courses of *Herpes simplex* infections in transfer factor-treated (lower panel) and control mice (upper panel).

FIG. 26 shows the reverse phase chromatography of *Herpes simplex* virus type-1 gD (HSV-1gD). Affinity purified HSV-1 specific transfer factor (25 to $30 \times 10^8$ ce) isolated from 800–1,000 ml of bovine blood) was redissolved in 1.0 ml of deionized water. The sample was centrifuged at 10,000×g for 4 minutes and passed through a 0.2 μm filter. Aliquots of 200 μl ($8 \times 10^8$ ce) of the filtered sample were injected onto a reverse phase C18 column (RP-C18, Vydac 4.6×250 mm) previously equilibrated with 5 mM tetrabutyl ammonium phosphate (TBAP, hplc grade Pierce, Rockford Ill.; buffer A). The bound protein was eluted with a linear gradient (1% change in % buffer B/min) of 5 mM TBAP, 100% acetonitrile (CH3CN hplc grade Fisher, Pittsburgh, Pa.; buffer B) at a flow rate of 1 ml/min. Elution of protein was monitored at 214 nm. A single major peak (arrow) eluted at 5 to 10% $CH_3CN$. The peaks from four separate runs were pooled, dialyzed against deionized water and lyophilized. An aliquot ($7 \times 10^8$ ce) was used to assay for bioactivity.

FIG. 27 shows the delayed type hypersensitivity response (DTH) assay of purified HSV-1 specific transfer factor. Bovine HSV-1 specific transfer factor dialysate was lyophilized and dissolved in 2.0 ml water. HSV-1 dialysate, the acetonitrile eluate of gD Ni-NTA beads (gD eluate) and RP-C18 peak were diluted in HBSS to a concentration of $5 \times 10^7$ ce/ml. $5 \times 10^7$ ce (1.0 ml) of each fraction was administered intraperitoneally (ip) to each mouse in all experimental groups (n=6). Twenty-four hours later, footpads were injected with 25 μg of recombinant HSV-1 glycoprotein D (rHSV-1 gD) in 200 μl HBSS; contralateral footpads were injected with 200 μl HBSS. DTH response (footpad swelling) induced by HSV-1 specific transfer factor dialysate, gD eluate, and C18 Pk was determined twenty-four hours after injection of the antigen.

FIG. 28 shows the reverse phase chromatography of ovalbumin specific transfer factor (OVA-specific transfer factor) using TBAP solvent system. Affinity purified ovalbumin specific transfer factor ($13 \times 10^8$ ce) isolated from murine spleen lymphocytes was redissolved in 0.5 ml of deionized water. The sample was centrifuged at 10,000×g for four minutes and passed through a 0.2 μm filter. Aliquots (200 μl) of the filtered sample were injected onto a reverse phase C18 column (RP-C18, Vydac 4.6×250 mm) previously equilibrated with 5 mM tetrabutyl ammonium phosphate (TBAP, hplc grade Pierce, Rockford, Ill.; buffer A). The bound protein was eluted with a linear gradient (1% change in % buffer B/min) of 5 mM TBAP, 100% acetonitrile ($CH_3CN$ hplc grade Fisher, Pittsburgh, Pa.; buffer B) at a flow rate of 1 ml/min. Elution of protein was monitored at 214 nm. A single major peak (arrow) eluted at 5 to 10% $CH_3CN$. The peaks from three separate runs were pooled, dialyzed against deionized water and lyophilized.

of 0.045% specific transfer factor A, 100% acetonitrile (CH$_3$CN hplc grade Fisher, Pittsburgh, Pa.; buffer B) at a flow rate of 100 μl/min. Elution of protein was monitored at 214, 260 and 280 nm. The peak observed from an injection of 3×10$^8$ ce of affinity purified ovalbumin specific transfer factor was collected, and subjected to N-terminal sequence analysis. An aliquot (6×10$^7$ ce) was saved to test bioactivity.

Figure 30:
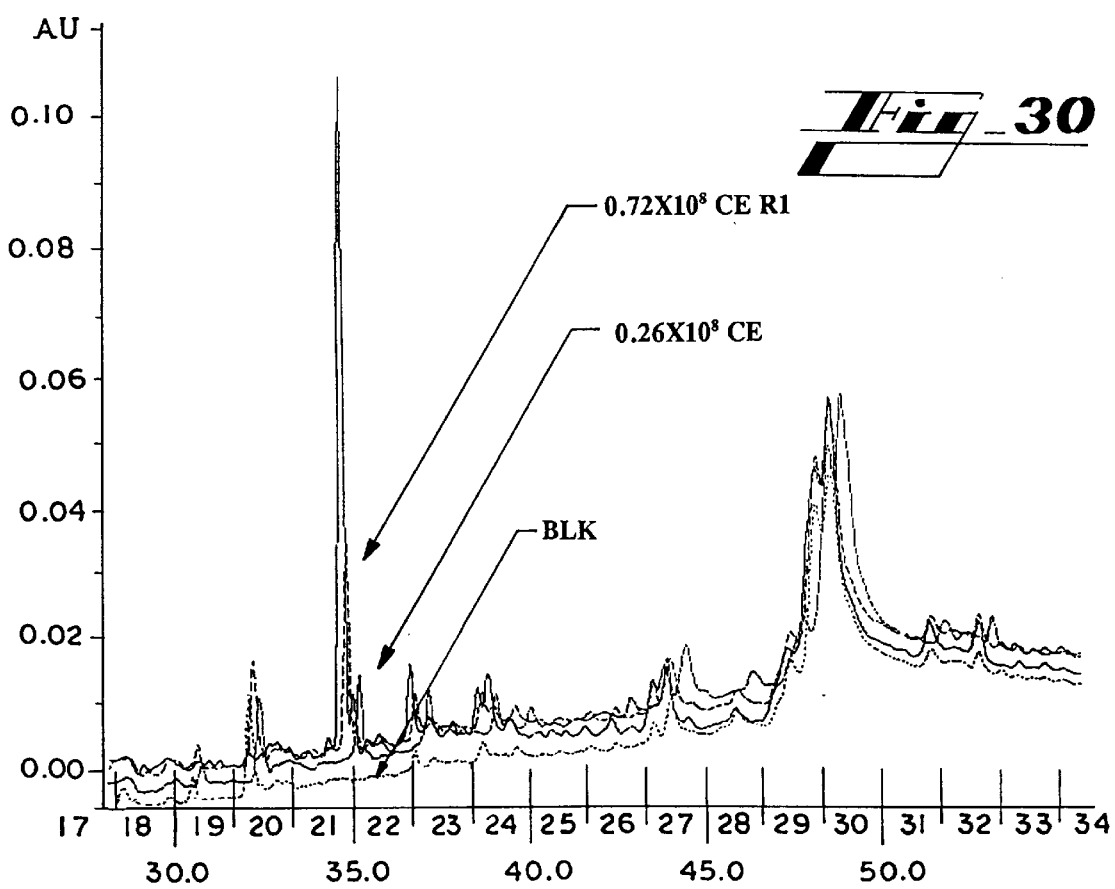

FIG. 30 shows sequential injections of increasing quantities of specific transfer factors (blank, 0.26, 0.72 and 3×10$^8$ ce) demonstrating that a single major peak eluted at 30% CH$_3$CN. The height of this peak increased in direct proportion to quantity injected. Background peaks (present in buffer A blank) did not increase in height.

FIG. 31 shows a delayed type hypersensitivity response (DTH) assay of purified ovalbumin specific transfer factor. The RP-C18 peak observed from an injection of 3×10$^8$ ce of affinity purified ovalbumin specific transfer factor using the specific TFA solvent system, was collected. An aliquot (6×10$^7$ ce) was dialyzed and diluted in HBSS to a concentration of 5×10$^7$ ce/ml and 1.0 ml was administered intraperitoneally (ip) to each mouse (n=6). Twenty-four hours later, footpads were injected with 100 μg of ovalbumin in 25 μl HBSS; contralateral footpads were injected with 25 μl HBSS. DTH responses (footpad swelling) induced by the ovalbumin-specific transfer factor RP-C18 peak was determined twenty-four hours after injection of the antigen.

Figure 32:
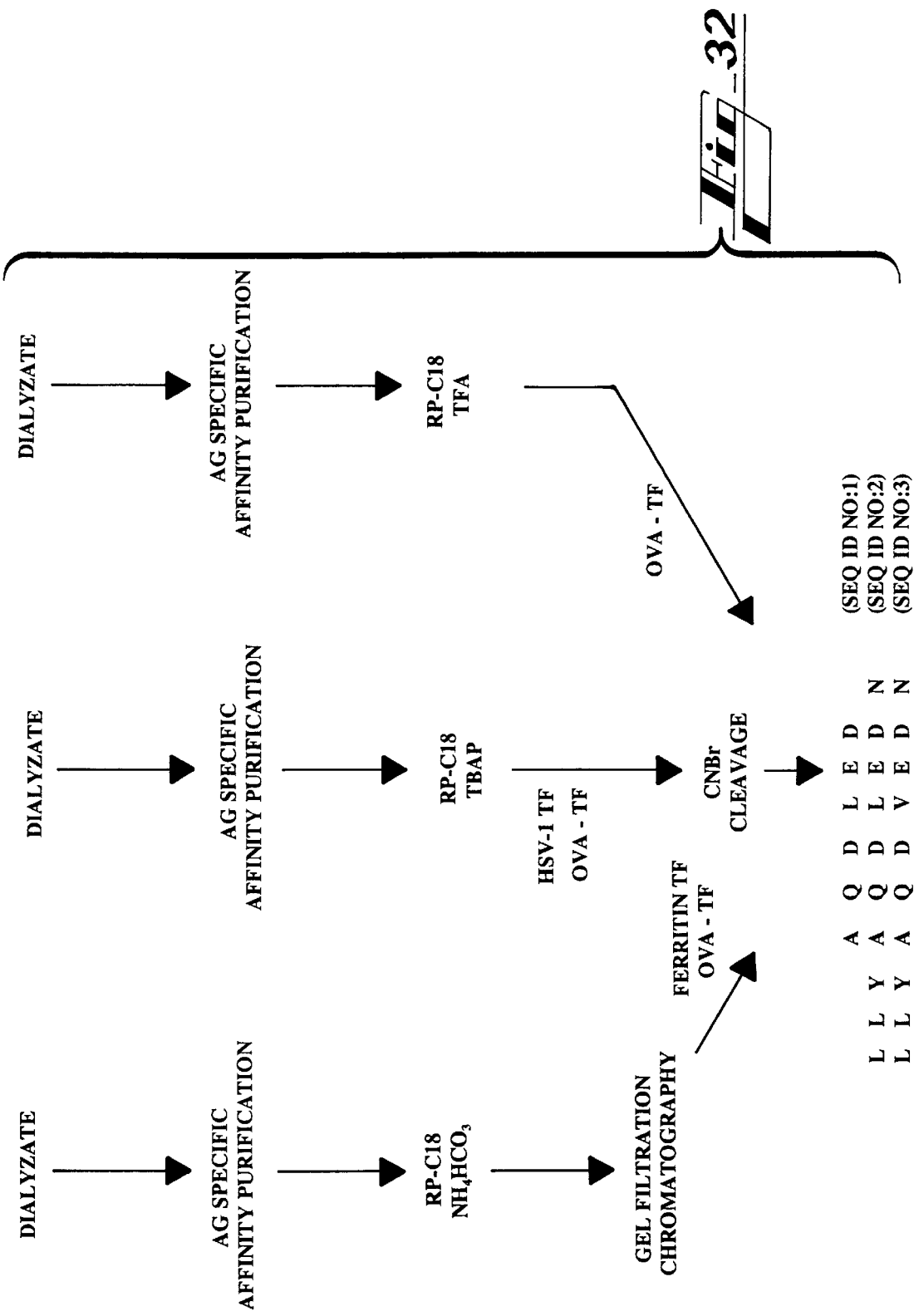

FIG. 32 shows that methods for the purification of specific transfer factors with different specificities yields an amino acid sequence of a common conserved region. Specific transfer factors with different specificities (ferritin, ovalbumin (Ova), and *Herpes simplex* type-1 (HSV-1) were isolated using the purification processes diagrammed. Three different preparations of ovalbumin-specific transfer factor were isolated using three different purification processes. All of the purified specific transfer factors were subjected to CNBr cleavage, followed by N-terminal sequence analysis. A highly conserved amino acid sequence was observed in all of the CNBr fragments.

Figure 33:
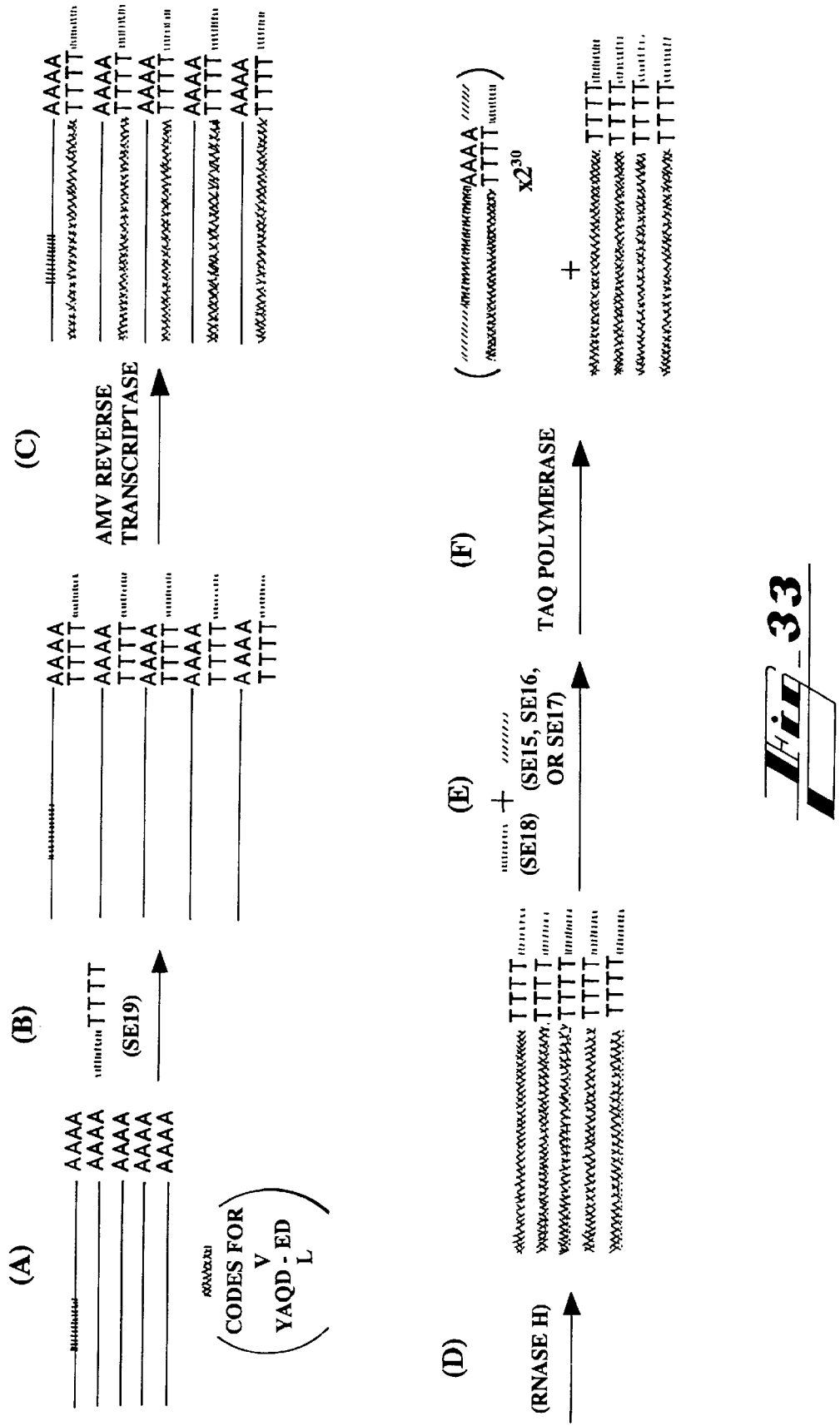

FIG. 33 shows the strategy for amplifying partial transfer factor cDNAs using 3' RACE. A portion of the poly A+ RNA contained in the total RNA from spleen cells and lymphocytes codes for the amino conserved acid sequence (a). Annealing of oligonucleotide SE19 to the RNA (b) is followed by primer extension with AMV reverse transcriptase (c); and RNA hydrolysis (due to the AMV reverse transcriptase's inherent RNase H activity) (d). A PCR reaction containing oligonucleotide SE18 is divided into three separate reactions, containing either SE15, SE16, or SE17 (e). At 90° C., Taq polymerase is added (f) and the reactions are subjected to 30 cycles of denaturation, annealing, and extension.

Figure 34:
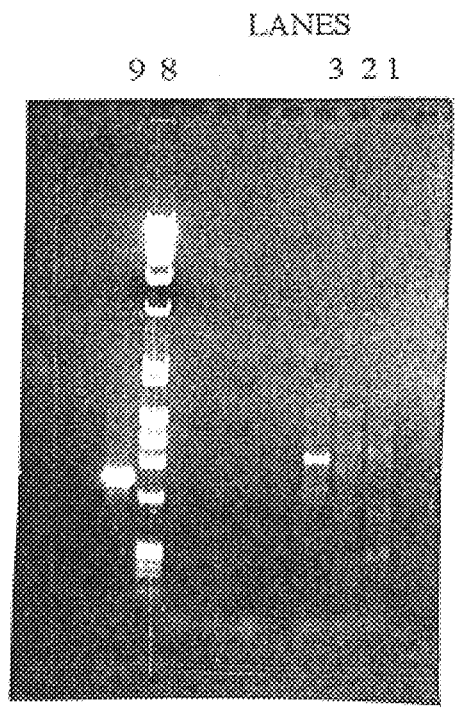

FIG. 34 shows that samples (10 μl) from PCR reactions were subjected to electrophoresis through a 1.1% agarose (TAE buffer, see Maniatis) gel. PCR reactions were identical, except for the oligonucleotide primers: Lane 1, primers SE15 and SE18; Lane 2, SE16 and SE18; Lane 3, SE17 and SE18. Lanes 8 and 9 contain molecular weight markers.

Figure 35:
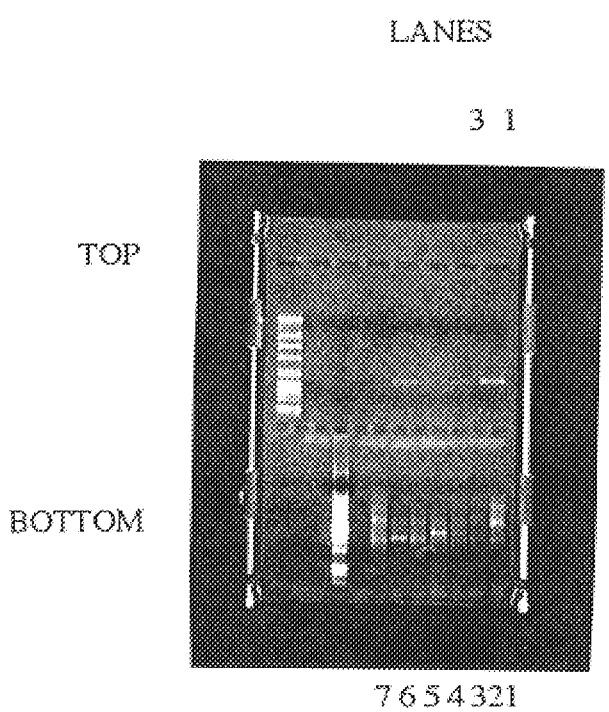

FIG. 35 shows that PCR samples were electrophoresed as in FIG. 34. Top Panel: Lane 1, RNA (used for cDNA synthesis) was from spleen cells of ferritin-immunized mice; Lane 3, RNA was from circulating blood lymphocytes of a HSV-1-immunized calf. Bottom Panel: RNA from various mouse tissues were used for cDNA synthesis, as follows: Lane 1, brain; Lane 2, heart; Lane 3, kidney; Lane 4, liver; Lane 5, ovary; Lane 6, spleen; Lane 7, thymus.

DETAILED DESCRIPTION

The present invention provides the characterization of a conserved transfer factor region, methods of isolating or producing such a conserved transfer factor region or a transfer factor containing the conserved region, and methods of diagnosing, preventing and treating various diseases with the transfer factor, or a conserved transfer factor region. The invention provides amino acid and nucleic acid sequences encoding for a conserved transfer factor region.

The invention provides an isolated nucleic acid comprising a nucleotide sequence encoding at least a portion of a conserved transfer factor region. In preferred embodiments, the conserved transfer factor region comprises the amino acid sequence of SEQ ID NO:1, SEQ ID NO:2 or SEQ ID NO:3, or a functional homologue thereof. In preferred embodiments, the nucleotide sequence encoding at least a portion of a conserved transfer factor region comprises SEQ ID NO:14, or a functional homologue thereof.

The invention provides that the nucleic acid can be present in a vector capable of expressing at least a portion of the conserved transfer factor region when in a cell. The invention provides a method of expressing at least a portion of a conserved transfer factor region comprising transfecting a cell with a vector containing a nucleic acid sequence encoding at least a portion of a conserved transfer factor region, wherein the vector is capable of expressing the conserved transfer factor region when in the cell. The invention also contemplates the extracellular expression of at least a portion of a conserved transfer factor region, such as in a cell free system.

The invention further provides an isolated nucleic acid comprising an antisense nucleotide sequence capable of selectively hybridizing to at least a portion of a conserved transfer factor region nucleotide sequence, and which inhibits expression of the conserved transfer factor region. The invention also provides a method of expressing such a nucleic acid comprising an antisense nucleotide sequence capable of selectively hybridizing to at least a portion of a conserved transfer factor region nucleotide sequence, and which inhibits expression of the conserved transfer factor region.

The invention provides an isolated antibody capable of specific binding with a conserved transfer factor region. The invention provides a hybridoma producing monoclonal or polyclonal antibodies capable of specific binding with a conserved transfer factor region.

The invention provides a substantially pure, or isolated transfer factor comprising a conserved region, preferably having an amino acid sequence comprising SEQ ID NO:1, SEQ ID NO:2 or SEQ ID NO:3, or a functional homologue thereof. The transfer factor preferably has a specific activity of at least 5000 units of transfer factor activity per absorbance unit at 214 nm wherein a unit of transfer factor activity is defined as the amount of material that produces a half-maximal footpad swelling response in mice, and wherein the isolated transfer factor is capable of transferring delayed-type cell mediated immunity to a non-immune human or animal.

The invention further provides an isolated peptide encoding at least a portion of a conserved transfer factor region, preferably comprising SEQ ID NO:1, SEQ ID NO:2 or SEQ ID NO:3, or a functional homologue thereof.

The invention also provides a method of identifying genetic material encoding at least a portion of a conserved region of transfer factor in a sample containing a first nucleic acid comprising combining the sample with a second nucleic acid encoding at least a portion of the conserved region of transfer factor, and detecting hybridization between the first and second nucleic acids. Furthermore, the invention provides a method of diagnosing an abnormal immune condition in a subject mammal comprising combining a bodily fluid sample containing a first nucleic acid from the subject mammal with a second nucleic acid encoding at least a portion of the conserved region of transfer factor; detecting hybridization between the first and second nucleic acids; comparing the level of hybridization to the sample with a level of hybridization to a sample from a normal mammal; and diagnosing the subject mammal as having an abnormal immune condition when the hybridization levels are significantly different. Preferably the nucleic acid sequence comprises SEQ ID NO:14 or a functional homologue thereof.

The invention provides a method of preventing or treating an infection in a mammal comprising administering to the mammal a preventative or treatment effective amount of a transfer factor, preferably having an amino acid sequence comprising SEQ ID NO:1, SEQ ID NO:2 or SEQ ID NO:3 or a functional homologue thereof. Such amounts can be routinely determined by a skilled artesan given the particulars of the infection or disease and the individual being treated.

The invention also provides a method of diagnosing an abnormal immune condition in a subject mammal comprising combining a bodily fluid sample from the subject mammal with an antibody capable of specific binding with at least a portion of a conserved transfer factor region; detecting binding of the antibody to the sample; comparing the level of binding to the sample with a level of binding to a sample from a normal mammal; and diagnosing the subject mammal as having an abnormal immune condition when the binding levels are significantly different.

As used in the claims, the term "a" can mean one or more than one, depending upon the context within which it is used. By "substantially pure" or "isolated" is meant in a form free from at least some of the components with which it is normally found in nature. By the term "homologue" is meant a sequence that has greater than 60%, more preferably 70%, and more preferably 80% identity to the subject sequence to which it refers. The term "functional homologue" means that altered sequences can be used in accordance with the invention which include deletions, additions or substitutions of different residues resulting in a sequence that encodes the same or a functionally equivalent gene product. The gene product itself may contain deletions, additions or substitutions of amino acid residues within a transfer factor sequence, which result in a silent change thus producing a functionally equivalent transfer factor protein. Such amino acid substitutions may be made on the basis of similarity in polarity, charge, solubility, hydrophibicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The utilities described herein are intended as exemplary and are not intended to be limiting. For example, a peptide containing at least a portion of the conserved transfer factor region, or a homologue thereof, can be used for regulating transfer factor levels in a diseased mammal by interacting with conserved transfer factor receptor mechanisms. Such a peptide can also be used for the production of antibodies for isolating, detecting or disabling transfer factors, as in a dialysis treatment, or for harvesting transfer factors sharing the conserved region to which the antibody is directed.

A nucleic acid encoding the conserved transfer factor region can be used for the recombinant production of protein or fusion proteins to be used in disease treatment or for the production of antibodies, as above, or a complementary nucleic acid strand can be used as antisense for the inhibition of transfer factor expression in vivo or for the detection of abnormal immune conditions based on comparing sample hybridizations. Antisense technology is described in more detail in U.S. Pat. No. 5,489,677, and the references cited therein. The particulars of refining each above mentioned technique for each set of circumstances and individuals are routine and well-known to skilled artisans.

The nucleotide sequence of the invention may be engineered in order to alter a transfer factor coding sequence for a variety of ends, including but not limited to, alterations which modify processing and expression of the gene product.

For example, mutations may be introduced using techniques which are well known in the art, e.g., site-directed mutagenesis, to insert new restriction sites, to alter glycosylation patterns, phosphorylation, etc.

In another embodiment of the invention, a conserved transfer factor region or a modified transfer factor sequence may be ligated to a heterologous sequence to encode a fusion protein. For example, for screening of peptide libraries for molecules that bind transfer factors, it may be useful to encode a chimeric transfer factor protein expressing a heterologous epitope that is recognized by a commercially available antibody. A fusion protein may also be engineered to contain a cleavage site located between a transfer factor sequence and the heterologous protein sequence, so that the transfer factor may be cleaved away from the heterologous moiety.

In an alternate embodiment of the invention, the coding sequence of transfer factors could be synthesized in whole or in part, using chemical methods well known in the art. See, for example, Caruthers et al., 1980, *Nuc. Acids Res. Symp. Ser.* 7:215–233; Crea and Horn, 180, *Nuc. Acids Res.* 9(10):2331; Matteucci and Caruthers, 1980, *Tetrahedron Letter* 21:719; and Chow and Kempe, 1981, *Nuc. Acids Res.* 9(12):2807–2817. Alternatively, the protein itself could be produced using chemical methods to synthesize a transfer factor amino acid sequence in whole or in part. For example, peptides can be synthesized by solid phase techniques, cleaved from the resin, and purified by preparative high performance liquid chromatography. (e.g., see Creighton, 1983, *Proteins Structures And Molecular Principles*, W. H. Freeman and Co., N.Y. pp. 50–60). The composition of the synthetic peptides may be confirmed by amino acid analysis or sequence (e.g., the Edman degradation procedure; see Creighton, 1983, *Proteins, Structures and Molecular Principles*, W. H. Freeman and Co., N.Y., pp. 34–49).

In order to express a biologically functional or active transfer factor, or conserved transfer factor region, the nucleotide sequence coding for transfer factors, or a homologue or functional equivalent, can be used directly as a probe for the detection of hybridizing nucleic acids in a sample or individual, or be inserted into an appropriate expression vector, i.e., a vector which contains the necessary elements for the transcription and translation of the inserted coding sequence. The transfer factor gene products as well as host cells or cell lines transfected or transformed with recombinant transfer factor expression vectors can be used for a variety of purposes. These include but are not limited to generating antibodies (i.e., monoclonal or polyclonal) that competitively inhibit activity of transfer factor protein and neutralize its activity; and antibodies that mimic the activity of transfer factor binding partners such as a receptor. Anti-transfer factor antibodies may be used in detecting and quantifying expression of transfer factor levels in cells and tissues, as well as isolating transfer factor-positive cells.

The substantially pure transfer factor has a specific activity of at least 5,000 units per $AU_{214}$. The preferred specific activity is at least 10,000 units per $AU_{214}$ with the most preferred specific activity of at least 20,000 units per $AU_{214}$ to 60,000 units per $AU_{214}$. The substantially pure transfer factor is a polypeptide with a molecular weight of approximately 4900 to 5500 Daltons. The substantially pure transfer factor can transfer delayed type cell mediated immunity to a non-immune human or animal.

The substantially pure transfer factor is effective in transferring cell mediated immunity in humans or animals for a wide variety of antigens or epitopes. The substantially pure transfer factor can be administered either by injection or can be administered orally or nasally. Injection can be intravenously, intramuscularly or subcutaneously or a combination of routes.

When injected, the dose of transfer factor required to impart immunity to a human is between approximately 1 ng and 500 ng with a preferred dose range of between 25 ng and 250 ng with a most preferred dose of approximately 50 ng. The optimal dose for any particular transfer factor will vary within the stated range. The invention also contemplates a variety of other modes of administrations, such as by liposomes.[37]

The present invention also provides an oligonucleotide encoding at least a portion of the conserved region of transfer factor which can be used for identification of transfer factors encoding genetic material or for the production of recombinant transfer factor, including chimeric proteins.

There is strong evidence that immunity against certain viruses, especially the human Herpes viruses, is dependent upon the cell-mediated immune system. Activation of cell-mediated immunity with a specific transfer factor would be expected to improve the normal mechanisms that act to clear active viral infections. A similar activation of specific immunity by a transfer factor can provide protective immunity against the virus even before it is encountered. The latter proposal is supported by the report of Steele et al., in which children with acute leukemia were protected against chicken pox infections by administration of a *Varicella zoster* (chicken pox)-specific transfer factor fraction.[38] It is important to consider the rapidity of action of transfer factors. The recipients acquire specific immunity in 24 to 48 hours. This is much more rapid than the 2 to 6 weeks required for induction of immunity by conventional vaccines.

Tuberculosis, leprosy and infections caused by "atypical" mycobacteria (i.e., *Mycobacterium avium* complex) may produce immunodeficiency in the patients or may occur because the patient had an immune deficiency that allowed the organism to establish an infection. Similar evidence exists for certain fungal infections. There is evidence that many patients with these diseases have impaired cell mediated immunity and that these immune deficiencies may be corrected with a specific transfer factor.

Mechanisms of immunity to intestinal parasites are variable. However, AIDS, a disease in which cell-mediated immunity is severely impaired has provided evidence that certain parasitic diseases of man are related to cell-mediated immune responses. These include cryptosporidiosis and isosporosis. A placebo controlled, clinical trial of specific transfer factor in patients with intestinal cryptosporidiosis showed significant beneficial responses in the transfer factor recipients.[39]

The observation of Steele, et al.[40] that chicken pox infections could be prevented by pretreatment of children with the appropriate transfer factor indicates an important role for transfer factors as agents to prevent certain infectious diseases. Because transfer factors activate the cell mediated immune system and act very rapidly, they provide an important novel approach to prophylactic immunity that is not provided by currently used vaccines (that are used because they stimulate antibody production). Specific examples include, but are not limited to:

a. prevention of varicella;

b. prevention of parasitic infections, i.e., cutaneous leishmaniasis, in travelers to endemic areas;

c. prevention of cytomegalovirus infections in recipients of organ transplants;

d. prevention of *Pneumocystis carinii* pneumonia in patients with cellular immunodeficiency because of viral infections (i.e., HIV) or immunosuppressive treatments;

e. prophylaxis against certain infectious diseases (i.e., leishmaniasis) that are endemic in certain geographic areas.

The substantially pure transfer factor of the present invention is useful in treating a wide variety of pathological conditions in both humans and animals. For example, the substantially pure transfer factor of the present invention can be used to treat or prevent viral infections, including, but not limited to, *Herpes simplex*, types I and II, Epstein-Barr virus, cytomegalovirus, measles, human immunodeficiency virus (HIV), and other viruses that cause disease in humans and animals. The substantially pure transfer factor of the present invention can be used to treat or prevent fungal infections, including, but not limited to, *Candida albicans, Histoplasma capsulatum, Coccidioidies immitis*, and *Pneumocystis carinii*. The substantially pure transfer factor of the present invention can be used to treat or prevent mycobacterium infections, including, but not limited to, *Mycobacterium leprae, Mycobacterium tuberculosis*, and *Mycobacterium avium* complex. The substantially pure transfer factor of the present invention can be used to treat or prevent parasitic infections including, but not limited to, *cryptosporidia, isospora, leishmania* species, *coccidia*, and other parasites that infect humans and animals.

Certain immunodeficiency syndromes are characterized by selective defects in cell-mediated immunity. Patients with these disorders are susceptible to infections with common ubiquitous microorganisms such as *Candida albicans*, herpes viruses, *Pneumocystis carinii* and certain intestinal parasites.

The immunologic deficiencies in certain diseases such as the Wiskott-Aldrich syndrome and chronic mucocutaneous candidiasis are genetically determined and usually are diagnosed within the first few years of life. Others are acquired through immunosuppressive treatments, immunosuppressive diseases or through unknown mechanisms.

Kirkpatrick, et al., have shown that specific transfer factor therapy corrects the immune deficiency in patients with chronic mucocutaneous candidiasis and these patients resist relapses after their infections are cleared with antifungal agents. Specific examples of immune deficiency diseases that can be treated with the substantially pure transfer factor of the present invention include, but are not limited to, a. chronic mucocutaneous candidiasis;
b. hyper IgE syndrome;
c. Wiskott-Aldrich syndrome;

Although not wanting to be bound by the following hypothesis, it is believed that transfer factors are specific for a particular antigen or epitope. Thus, each transfer factor molecule can transfer immunity to a specific epitope. It is believed from the data obtained from the substantially pure transfer factor made according to the present invention that each transfer factor molecule has a region with a constant amino acid sequence. In another region, the amino acid sequence is variable. It is the variable region that provides the specificity for a particular antigen.

By isolating a substantially pure transfer factor that is specific for a particular epitope, one can then sequence the transfer factor and, using the sequence data, produce the transfer factor in large quantities by either chemical synthesis or by recombinant technology.

In addition, it is contemplated as part of the present invention to produce large amounts of a substantially pure transfer factor from an immunized animal by the process described herein. This substantially pure transfer factor can then be used to transfer immunity to another, non-immune animal or human.

It is important to note that the substantially pure transfer factor according to the present invention can be produced from one species, for example, bovine, and the substantially pure transfer factor from the bovine source can successfully be used to transfer specific immunity to another species, for example, a human.

Although not wanting to be bound by the following hypothesis, results suggest transfer factors are produced by CD4+ (L3T4+) peripheral T cells. These experiments were performed by isolating macrophages, B cells, CD4+ T cells, and CD8+ T cells from actively-sensitized mice, preparing dialysates from these cells, and performing dose-response studies for transfer factor activity using these preparations in naive recipient mice. Comparison of the titration curves for each dialyzate preparation with data on the purity of each cell preparation (from cytofluorography) suggests that all transfer factor activity was contributed by CD4+ T cells. The major histocompatibility complex restricted production of transfer factors is compatible with the notion they are produced by T cells. It is believed that transfer factors are encoded by a set of germ-line genes in CD4+ cells which are rearranged through processes similar to those known to effect rearrangement of other antigen-specific molecules. The similar physicochemical properties of transfer factors of differing antigen specificities might suggest genes encoding constant and variable regions for transfer factors. It is further suggested that transfer factors are produced in a clonal manner, and that the transfer factor produced by a given T cell will have specificity for an epitope of the same antigen as the T cell receptor (TCR) on that T cell. Clonality for transfer factor production is compatible with the antigen-specific activity of transfer factors. In this regard, it is suggested that different amino acid residues on the same epitope-containing peptide are recognized by a transfer factor and its corresponding TCR.

Perhaps the most provocative issue raised by these proposals is the mechanism by which the random rearrangement of T cell receptor genes might be coordinated with the rearrangement of transfer factor genes. Implicit from this model is a specific signaling mechanism between TCR and transfer factor genes. There are no data for the coordination of a system as complex as this in the literature. In this regard, one can conceive of a unique set of trans-acting factors which regulate transfer factor gene rearrangement. Alternatively, one might envision antigen, recycled TCR, or fragments of one of these serving this purpose. Whatever the mechanism, this is one of the most enigmatic features for this model. As opposed to models of random transfer factor gene rearrangement, this model provides for the elimination of cells which might otherwise produce transfer factors with specificity for autologous antigens. That is, the clonal deletion of autoreactive T cells based on their TCR reactivity would also eliminate transfer factors having corresponding specificity. In this regard, Burnet[41] proposed a germ-line model for transfer factor genes, also proposing clonal production of transfer factors, as part of what is often called the "minireceptor hypothesis." Other than the issue of coordinated regulation of gene rearrangement, the present model closely resembles what is known for immunoglobulin and TCR gene organization and rearrangement.

It is believed that transfer factors are not constitutively produced, and are not necessary for the induction of primary immune responses. Transfer factor activity in experimental in vivo systems is only evident for preparations from sensitized donors. At minimum, a 10,000-fold enhancement of transfer factor activity for such preparations is suggested. Also, the rapid (24 hour) induction of DTH responsiveness in transfer factor recipients is not consistent with a natural role for transfer factors in induction of primary immune responses.

It is believed that transfer factors can be obtained from memory T lymphocytes. The kinetics observed for transfer factor activity using in vivo experimental models (i.e., the induction of responsiveness within 24 h), are consistent with secondary immune response kinetics. The failure of transfer factors to induce in vitro T cell proliferation is compatible with the notion that memory T cells contain transfer factor activity. The diminution of memory T cell responses to antigen challenge in the absence of periodic antigen-driven T cell activation is compatible with a similar decline in the DTH responsiveness of transfer factor recipients with time under similar conditions. The rapid induction of DTH responsiveness subsequent to administration of highly purified transfer factors may suggest that these molecules play a pivotal role in secondary immune responses, which is also compatible with the notion transfer factors may be present in memory T cells.

In summary, it is believed that transfer factors are encoded by rearranged germ-line genes in CD4+ T cells. It is further believed that transfer factors are produced subsequent to primary, MHC-restricted sensitization and may be obtained from memory T cells.

It is believed that under natural conditions transfer factors are functional following MHC-restricted antigen presentation to appropriate transfer factor-containing T cells. Results from experimental in vivo models show transfer factors function in allogeneic, and even xenogeneic, recipients. In contrast, passive transfer of DTH using cloned CD4+ T cells, which have been shown to mediate DTH, function in an MHC-restricted manner. These results may be reconciled by suggesting that administration of exogenous transfer factor in experimental in vivo models may circumvent an otherwise natural requirement for MHC-restricted antigen presentation before transfer factor functional activity is expressed.

It is further believed that following MHC-restricted antigen presentation to the TCR, transfer factors participate in reactions which lead to a secondary immune response phenotype for transfer factor-containing T cells. It is further believed that transfer factors may be released by transfer factor-containing T cells into the extracellular milieu, enter nearby naive T cells, and exert a similar effect on these cells as they do on transfer factor-producing cells. This would be compatible with results from experimental in vivo models showing administration of exogenous transfer factor stimulates DTH responsiveness for naive recipient animals or humans. Entry into naive T cells might involve an as yet unidentified receptor on the surface of these cells which binds transfer factors. Burnet[42] proposed the existence of "minireceptors" which would be complementary in structure to transfer factors. Thus, for a transfer factor of a given antigen specificity there would exist a minireceptor which would bind that transfer factor specifically. For the model presented here, a non-polymorphic receptor is proposed. Although no evidence is available for such a transfer factor receptor, one might envision molecules, such as CD-45R, which are expressed in greater quantity on naive than memory T cells as candidates for the receptor.

It is believed that transfer factors only function in T cells with specificity for antigen corresponding to that of the transfer factor. Thus, although any T cell in the vicinity of transfer factor-releasing T cells might have the ability to bind and take up any transfer factor, only those which have taken up the appropriate transfer factor and are subsequently presented with the appropriate antigen by syngeneic antigen presenting cells (APC) will respond to the transfer factor activity.

It is believed that transfer factors participate in T cell activation through specific binding of transfer factors to antigen. Results from study of the genetic regulation of transfer factor activity indicate transfer factors can confer a high responder phenotype to low responder mice in systems where tolerance is otherwise manifested through determinant selection mechanisms. In one experiment, DTH responsiveness was established for chicken ovalbumin or the ovalbumin immunodominant peptide in low responder CBA/J (H-$2^k$) mice using transfer factor preparations from high responder BALB/cBy (H-$2^d$) mice. It has been shown that the failure of H-$2^k$ mice to respond to this antigen is due to the inability of antigenic ovalbumin peptides to bind H-$2^k$ class II antigen. Additionally, the results indicate transfer factors bind intact protein antigens, including chicken ovalbumin, in a specific manner. Together, these results are compatible with a role for transfer factors in antigen presentation to T cells. This may occur through the formation of MHC product/transfer factor/antigen complexes on the surface of APC. Observations of transfer factor activity in allogeneic and xenogeneic systems might be compatible with the notion that transfer factors interact with conserved portions of MHC-encoded molecules distal to the antigen-binding cleft in a manner analogous to that proposed for superantigen binding to MHC products. Thus, an MHC-encoded molecule to which a transfer factor is bound distal to the antigen-binding cleft in an orientation which places transfer factor-bound antigen in the cleft might comprise the configuration of a functional MHC product/transfer factor/antigen complex.

Results from experimental in vivo models show that if transfer factors interact with intact, homologous antigen in solution prior to administration to recipients that transfer factor activity is abrogated. These results suggest that transfer factors must interact with immune system components prior to interaction with antigen. This would be compatible with results showing transfer factors must be administered prior to antigen challenge for DTH responses to be observed subsequently. Alternatively, this phenomenon may not be relevant under physiological conditions, and transfer factors may normally interact with antigen in vivo with full retention of transfer factor activity. The utility of a transfer factor antigen-binding function may be to reduce antigen competition for antigen presentation. That is, the binding of transfer factors to foreign antigens may facilitate the presentation of these antigens to T cells under conditions where an abundance of autologous antigens might otherwise compete effectively for binding with MHC molecules.

In summary, it is believed that transfer factor functional activity is enabled following MHC-restricted antigen presentation to transfer factor-containing T cells. This activity would be manifested in transfer factor-containing T cells through mechanisms resulting in a secondary immune response phenotype for these cells. It is also believed that transfer factors are released by stimulated T cells into the extracellular milieu where they bind to a transfer factor receptor molecule on the surface of nearby naive T cells. Following MHC-restricted antigen presentation, it is believed that these cells will also adopt a secondary immune response phenotype. It is also believed that transfer factors released by T cells have a role in antigen presentation which may be manifested through the specific antigen binding activity of transfer factors and facilitated through the formation of MHC product/transfer factor/antigen complexes on the surface of antigen presenting cells.

The purification strategy was based on several considerations not considered by the prior art. The defining and most well-established assay for transfer factors is an in vivo assay for delayed typed hypersensitivity. Therefore, there was a need to preserve the biological activity of the transfer factors throughout the purification process. Second, the in vivo assay for transfer activity has traditionally been performed using a single dose sample. Whereas this approach provides important qualitative information on the presence of transfer factor activity, it was necessary to develop a quantitative assay to properly monitor the purification process. Third, early experiments indicated only picomolar quantities of transfer factors were obtained from gram quantities of tissue. Furthermore, methods were sought which would yield material of sufficient quality and quantity for biochemical characterization and structural studies. In the interests of minimizing sample handling, and therefore minimizing non-specific sample loss, volatile buffers were used throughout the purification process. It was also found that conventional high performance liquid chromatography solvents, such as trifluoroacetic acid, inactivates transfer factors. It was therefore necessary to devise a new solvent system that would allow purification of the transfer factor while not affecting the biological activity.

Figure 1:
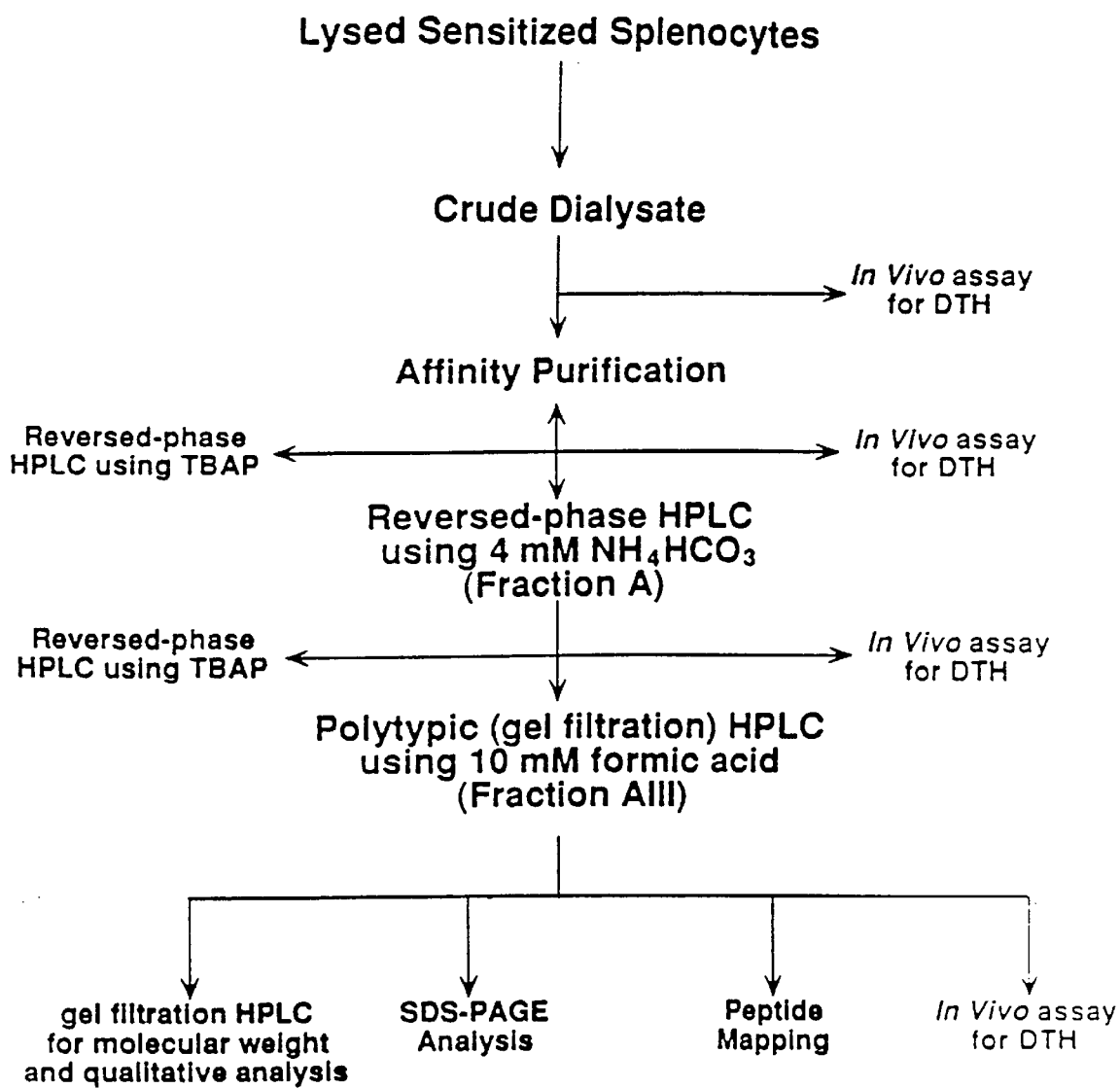
FIG. 1 is a schematic of one strategy used to purify transfer factor.

Fourth, preliminary data indicated that even samples containing relatively large quantities of transfer factor activity absorb only small amounts of light at wavelengths over 235 nm. Thus, chromatographic solvent systems were selected which have utility at short wavelengths. The strategy that was developed is shown in FIG. 1. It should be noted that in FIG. 1, the two high performance liquid chromatography steps may be reversed, i.e., the polytypic (gel filtration) high performance liquid chromatography can be performed first and the reversed-phase high performance liquid chromatography can be performed second. In some cases, the desired specific activity can be obtained after the affinity purification step.

Specific activity is defined in terms of transfer factor activity per absorbance unit at 214 nm. This measurement of specific activity was developed because substantial portions of the samples would have been required to make conventional protein determinations, and because absorbance of short wavelength UV light is an accepted, non-destructive means for the detection of peptides and proteins. Development of this system for relating transfer factor activity in units to protein concentration allowed specific activity to be monitored throughout the purification process.

Briefly, the isolation procedure is a method of producing substantially pure transfer factor comprising the steps of contacting a transfer factor-containing sample to an immobilized antigen to which the transfer factor binds specifically under conditions favoring binding of antigen-specific transfer factor to the antigen to form a transfer factor:antigen complex. The antigen-specific transfer factor is then separated from the complex. The antigen-specific transfer factor is then applied to a first reversed phase, high performance liquid chromatography column. The antigen-specific transfer factor is eluted from the first reversed phase, high performance liquid chromatography column and is then applied onto a second, gel filtration, high performance liquid chromatography column. The two high performance liquid chromatography column steps can be reversed. The substantially pure transfer factor is then eluted from the second high performance liquid chromatography column, the antigen-specific transfer factor having a specific activity of at least 5,000 units per absorbance unit at 214 nm.

The following specific examples will illustrate the invention as it applies to enhancing the immune response of an organism to small haptens. It will be appreciated that other examples will be apparent to those of ordinary skill in the art and that the invention is not limited to these specific illustrative examples. Various references are mentioned throughout this specification, which are hereby incorporated by reference in their entireties.

EXAMPLE 1

This example explains the preparation of crude dialysates which contain transfer factor.
Preparation of Ferritin and Ovalbumin Specific Transfer Factors Following Petersen et al.,[43] groups of 100–150 BALB/cByJ mice, 8–14 weeks old, which have been maintained on water and pellet food ad libitum, were "sensitized". This means that either ferritin or chicken egg albumin in aqueous solution was emulsified in equal amounts of Freund's complete adjuvant. Each mouse received 100 $\mu$g of the sensitizing antigen in a 40 $\mu$l volume, which was injected into two sites at the base of the tail, subcutaneously. After three weeks, six mice were selected randomly and were subjected to a delayed type hypersensitivity assay. This assay involved injection of 35–100 $\mu$g of antigen in 25 $\mu$l of HBSS, subcutaneously into hind footpads. Contralateral footpads were injected with 25 $\mu$l of HBSS. The antigen used in the assay was the same one administered to the mice previously. The footpad thickness was measured before and 18 hours after injection, using a dial gauge micrometer. Scores were taken from the difference between these values. Previous experimental work by Petersen et al. had shown that maximal swelling occurs 18–24 hours after injection.

If the subject mice had footpad swelling responses to the antigen significantly greater than the response to the diluent ($p<0.05$), all mice in the group were sacrificed. Spleens were removed aseptically, and single cell suspensions were prepared by gently forcing the cells through sterile 60 mesh stainless steel screens. The cells were washed three times with HBSS, an aliquot was removed, and mononuclear cells counted using trypan blue as vital exclusion dye. Overall viability was always greater than 90%. Cells were then suspended in sterile purified water in 50 ml sterile propylene centrifuge tubes, and lysed via repeated freezing in dry ice—ethanol baths and thawing in 37° C. water baths. When microscopic observation confirmed that lysis was essentially complete, the lysates were placed in dialysis bags which had previously been boiled in purified water. These bags had molecular weight cut offs of 6000–8000 Daltons. Dialysis was carried out at 4° C. against 50 volumes of sterile purified water under constant stirring for 24 hours. This was conducted twice, serially. The dialysates which resulted were pooled and lyophilized, and the lyophilized material reconstituted to $10^8$ mononuclear cell equivalents (ce)/ml, using purified sterile water. After sterilization by passage through a 0.22 $\mu$m filter, and confirmation of sterility by testing an aliquot on blood agar plates, the cells were stored at –20° C.

EXAMPLE 2

The dialysates were assayed for transfer factor activity as described by Kirkpatrick et al., the disclosure of which is incorporated by reference.[44]

Volatile solvents were removed from samples by lyophilization. Samples were brought to a concentration of $10^8$ mononuclear cell equivalents per milliliter using sterile purified water as diluent. Test materials were administered to mice by intra-peritoneal injection of 1.0 ml sample per mouse. Six mice were used for each data point unless indicated otherwise. The assay for delayed-type hypersensitivity was initiated 24 hours following injection of transfer factor sample.

For purposes of quantitating recovery between purification steps, one unit of transfer factor activity was defined as the material producing a half-maximal footpad swelling response from a dose-response curve of $\log_{10}$ of the mononuclear splenocyte equivalents versus the increment of footpad swelling. With the exception of the crude dialysates, the various purified preparations contained such small amounts of protein that substantial proportions of the samples would be required for conventional protein assays. For purposes of this application, the specific activity of the preparations is described in terms of the number of units of transfer factor activity per absorbance unit at 214 nm. The various volatile solvents were removed from samples through lyophilization. The samples were dissolved in purified water for absorbance measurements. These absorbance measurements were made using self-masking quartz glass microcuvettes (type 18M-S; NSG Precision Cells, Inc., Farmingdale, N.Y.) and a Gilford model 260 UV spectrophotometer (Gilford Instrument Laboratories, Inc. Oberlin, Ohio).

This assay is the protocol used for all tests of activity described herein, whenever reference is made to an "in vivo transfer factor assay."

EXAMPLE 3

This example describes affinity purification of transfer factor, following Kirkpatrick et al., which is incorporated herein by reference.[45] Immulon 2 Removawell strips were filled with antigen at a 100–200 $\mu$M concentration in a 0.05M sodium carbonate buffer, pH 9.6. Wells (Dynatech) were incubated overnight at 4° C. in a humid chamber, followed by washing three times with a PBS-TWEEN 20 solution (0.15M PBS, pH 7.4, 0.5 ml TWEEN-20/liter). Bovine serum albumin was then added at a concentration of 100 mg/ml. The wells were incubated at room temperature for one hour to saturate remaining protein binding sites.

The wells were washed three more times with the PBS-TWEEN solution. Then, spleen cell dialysates containing transfer factor were applied at $10^8$ mononuclear ce (cell equivalents)/ml in a volume of 300 µl. Dialysates corresponded to the antigen that had been added previously, e.g., cell lysates from animals immunized with ferritin were used with ferritin treated strips. The strips were then incubated at 4° C., 24 hours in a humid chamber.

The wells were washed two more times with PBS-TWEEN 20, and then once more with PBS. Following this, 300 µl of acetonitrile were added, and the wells were incubated for ten minutes at room temperature. Supernatants were removed, and an amount corresponding to $2.4 \times 10^8$ ce (2.4 ml) were set aside for the in vivo transfer factor assay described above. Samples were dried under nitrogen in a 37° C. water bath. The samples for the assay were reconstituted to $10^7$ ce/ml, using purified water. The material used in further purification steps was dissolved in from 1–5 ml of 5 mM ammonium bicarbonate. The use of this material is described herein.

EXAMPLE 4

Affinity purified transfer factor was then applied to reversed phase high performance liquid chromatography. It should be noted here that use of conventional column solvents, e.g., trifluoroacetic acid, results in inactivation of the transfer factors. Therefore, a new solvent system for running the columns had to be devised to preserve transfer factor activity.

Between 10 and $30 \times 10^8$ ce were dissolved in a 0.2 to 0.5 ml volume of purified water, and this was applied to a 4.6×250 mm Vydac, 218TP54 octadecylsilane column, using 5.0 mM ammonium bicarbonate at flow rate 1.0 ml/min. Fractions were collected at 1 minute intervals, and UV data permitted detection. This was done via UV spectral data taken over 1.0 second intervals, between 203 and 280 nm, and monitoring absorbance at 214 nm.

Results not shown here demonstrated that when 5 mM ammonium bicarbonate and acetonitrile were used, with acetonitrile ranging from 0–60% of the eluate, all transfer factor activity eluted in the void volume. As a result, elution was carried out isocratically using 5 mM ammonium bicarbonate, and the unretained peak collected. Aliquots, usually containing $2.5 \times 10^8$ ces, were set aside for transfer factor in vivo transfer factor assays. The remainder was lyophilized, reconstituted using 1.0 ml of 10 mM formic acid, and retained at −20° C. for further purification by polytypic high performance liquid chromatography on gel filtration columns.

EXAMPLE 5

This example is directed to the purification of transfer factor using polytypic high performance liquid chromatography on gel filtration columns.

The manufacturer of the columns recommends an eluent ionic strength of at least 0.1M to minimize non-specific interactions between sample components and the column bed material. Optimal resolution of the transfer factor samples was achieved using a ten fold lower ionic strength than that recommended by the manufacturer.

To accomplish this, $20-30 \times 10^8$ ces of mononuclear cells were applied in 0.2 to 0.5 ml volumes to two 7.8×300 mm gel filtration high performance liquid chromatography columns, linked in series. This was eluted with 10 mM formic acid, pumped at a flow rate of 0.5 ml/mm. This system had a void volume of 12.2 ml and fractions were collected at 1.0 minute intervals, detection being accomplished as indicated above.

EXAMPLE 6

Comparative data were obtained by using the ion pairing agent TBAP and a 4.0×300 mm octadecylsilane column for reversed phase high performance liquid chromatography. Gradient elution in pilot experiments using 5 mM TBAP as starting solvent and 80% acetonitrile as final solvent indicated that all transfer factor eluted prior to a 25% (v/v) acetonitrile concentration. Linear gradients were performed using 5 mM TBAP/acetonitrile (92:8; v/v) as solvent "A" and 5 mM TBAP/acetonitrile (75:25; v/v) as solvent "B". Gradients were of the form: 0% B (10 minutes), 0–100% B (5 minutes) and 100% B (5.5 minutes). Flow rate was 0.5 ml/min, detection being carried out as described above.

EXAMPLE 7

A molecular weight determination was carried out using an adaptation of gel filtration high performance liquid chromatography methodology developed by Meyerson et al.[46] Individual samples were passed through two 7.8×300 mm gel filtration high performance liquid chromatography columns linked in series, using 50 mM potassium phosphate buffer, pH 7.0 with 200 mM NaCl as eluant. Samples were dissolved either in eluant or 1.0 mM HCl, depending on solubility. Empirically determined flow rate of 0.49 ml/min was used for eluant. The void volume was 12.0 ml (24.4 min), and total permeation volume of 22.5 ml (46.0 min).

EXAMPLE 8

A microdialysis method was used to analyze purified transfer factor preparations. The microdialysis method was a modification of that described in Overall.[47] Spectra/por 7 dialysis tubing was cut into small squares and washed in purified water. Potential peptide binding sites were saturated by incubating rinsed dialysis membranes at 4° C. for 16 hours with 0.1% (w/v) $NaN_3$ solution containing 25 µg/ml of a glutamic acid terpolymer of Mr 405, together with 25 µ/ml of peptide LWMRFA, Mr 823. Supernatant was discarded, and purified water added to the tube, followed by moderate shaking. Rinsing was repeated at least 8 times.

Following this, a cap of a 1.5 ml microcentrifuge tube was punctured using the wide end of a heated Pasteur pipette. Samples for dialysis ranging from 200 to 1000 µl were placed in the tubes, and dialysis membrane pieces placed across the open end. The cap was closed, and the tube inverted and fixed, using tape to the inner wall of a dialysis chamber containing 500 ml pure water. Trapped air was removed using "u" or hook shaped tipped Pasteur pipettes, covered with a small piece of tubing.

Dialysis was carried out at 4° C. under constant stirring for from 2–6 hours, depending on sample volume. Dialysate was discarded and, as needed, the above was repeated. Microcentrifuge tube was removed and centrifuged for 10 seconds in a microcentrifuge. The sample was carefully removed using a sterile tipped micropipette.

EXAMPLE 9

Dose-response studies were carried out using the splenocyte dialysates and affinity purified materials described above. In these experiments, the foot pad delayed-type hypersensitivity assay described above was carried out. Groups of 6 mice were used for each data point, and the testing was performed by injecting the antigen 24 hours after i.p. injection of the sample. Responses were taken 18 hours after this.

Figure 2A:
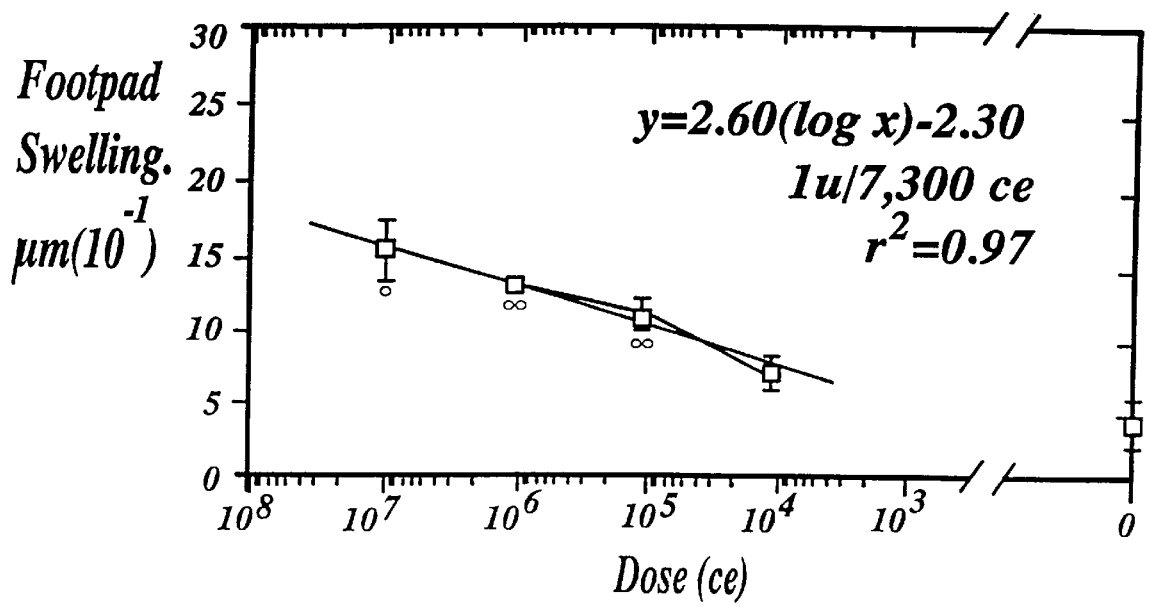
FIG. 2 shows dose-response relationships for dialysates of lysed splenocytes which contain transfer factor.
Figure 2B:
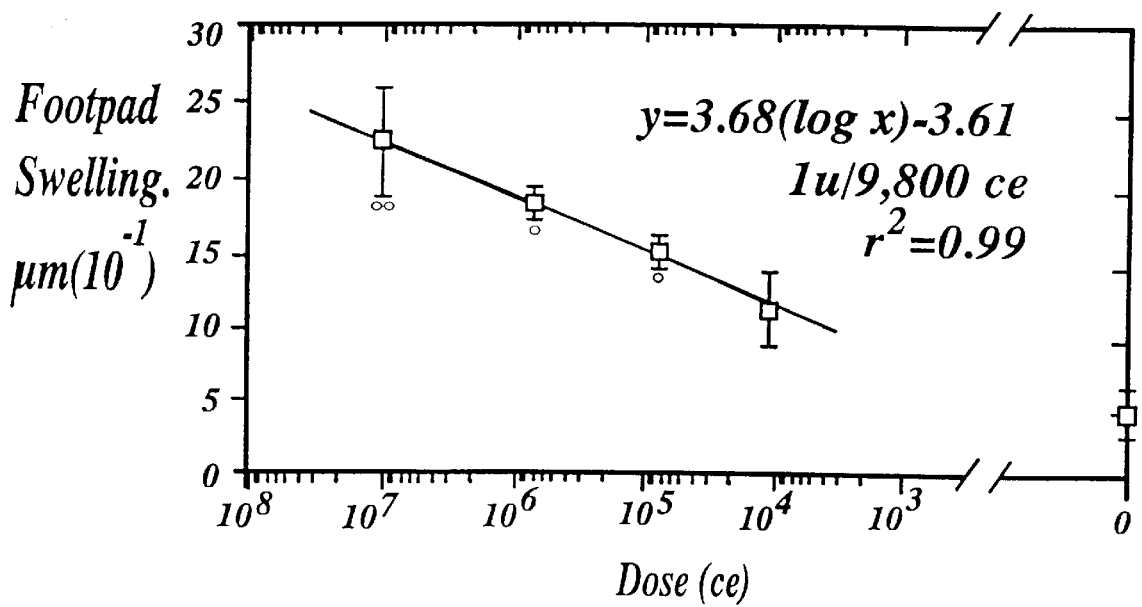

Background footpad response represents mice which received no i.p. sample. This is represented by "0 ce" in FIGS. 2 and 3. Coefficients of determination are expressed by $r^2$.

FIGS. 2 and 3 present these data. In each case, "A" represents results obtained using ovalbumin specific transfer factor, and "B" ferritin specific transfer factor.

In these data, magnitude of footpad swelling was proportional to the $\log_{10}$ of the dose when crude dialysates were used. This was previously observed by Rozzo et al. Coefficients of determination (r2) were 0.97 (FIG. 2A) and 0.99 (FIGS. 2B); therefore, the data describes the relationship well.

Figure 3A:
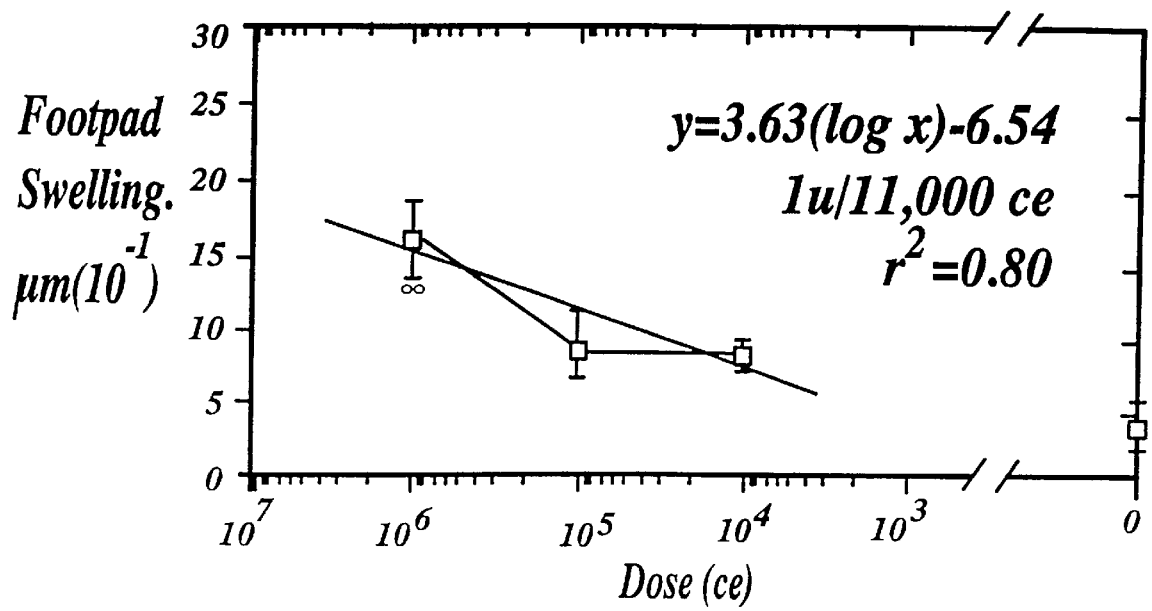
FIG. 3 shows the dose response relationship for transfer factor after affinity purification.
Figure 3B:
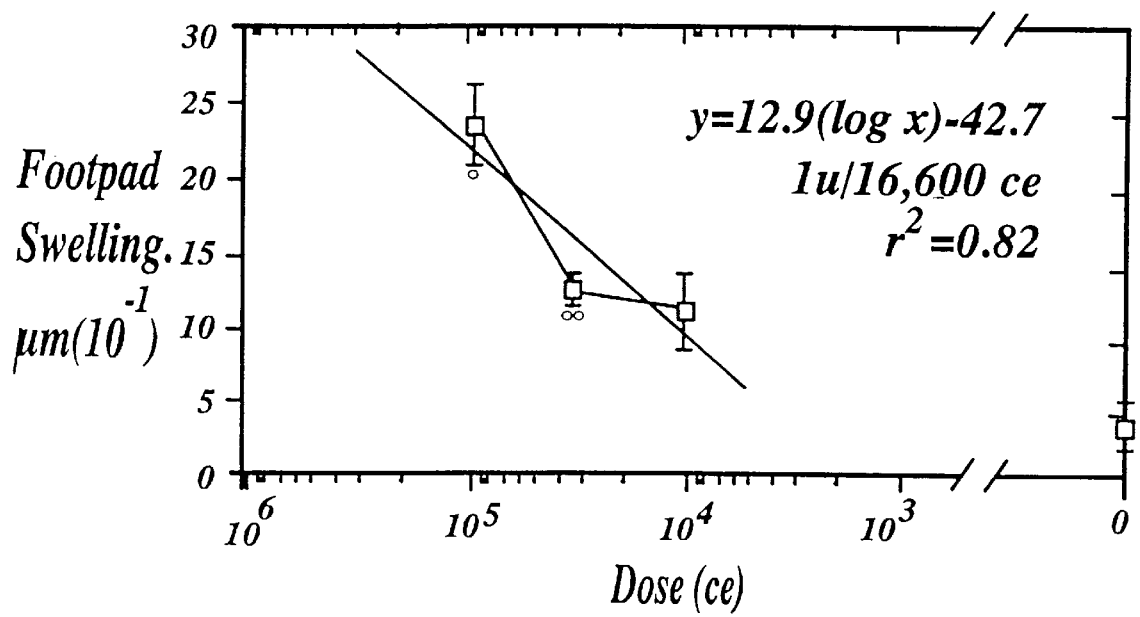

As shown in FIG. 3, the curves were similar, but the coefficients of determination were lower, being 0.80 for FIG. 3A, and 0.82 for FIG. 3B.

EXAMPLE 10

Following the purification protocols described above, yield and specific activity were calculated, also as indicated above. These results are presented in Table 1, which follows. Ovalbumin transfer factor showed a 46-fold enhancement of specific activity with a 66% yield, while ferritin transfer factor gave values of 53 fold and 59%.

In Table I, "RPLC" refers to reversed phase liquid chromatography, and "GFC" to the polytypic high performance liquid chromatography on gel filtration columns.

Figure 4:
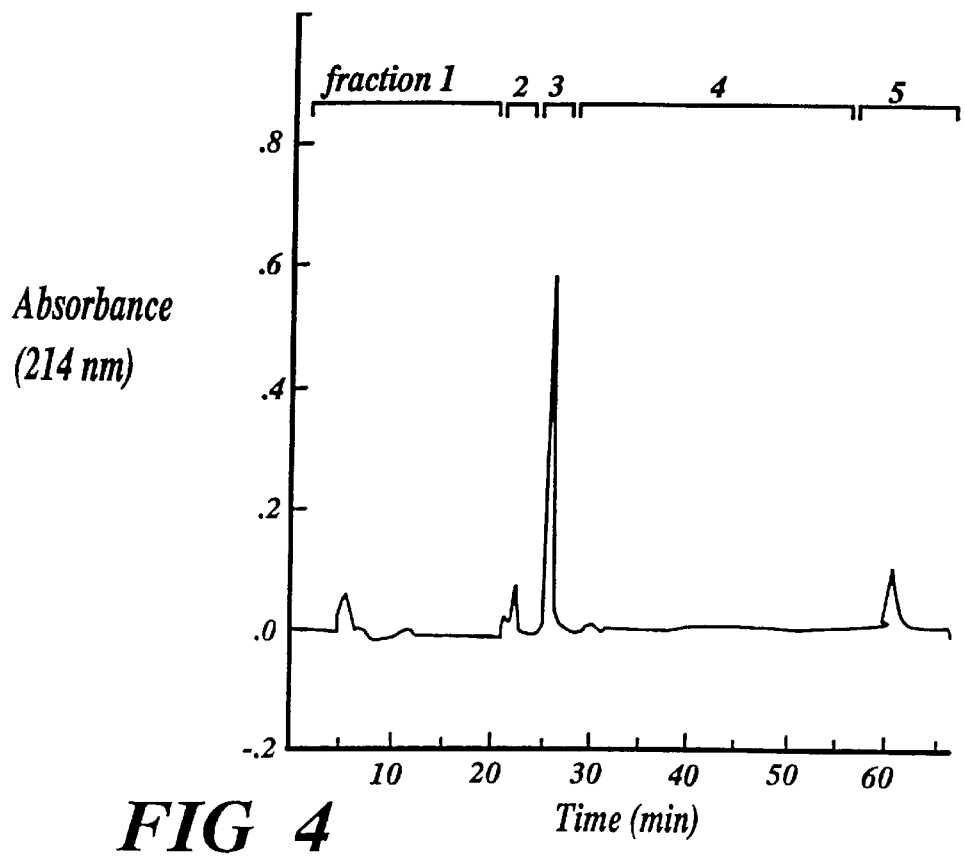
FIG. 4 shows reversed phase high performance liquid chromatography of affinity purified ferritin specific transfer factor.

With reference to Example 6, fractions were analyzed. The major chromophore detected at 214 nm. (Fraction 3; time=26.4 minutes) contained transfer factor activity. Fractions 1 and 5 also showed the activity at much lower levels, as can be seen via reference to FIG. 4, showing data obtained using ferritin specific transfer factor. The activity was measured using the previously mentioned footpad assay.

These results caused focus to be placed on fraction 3.

EXAMPLE 12

Figure 5:
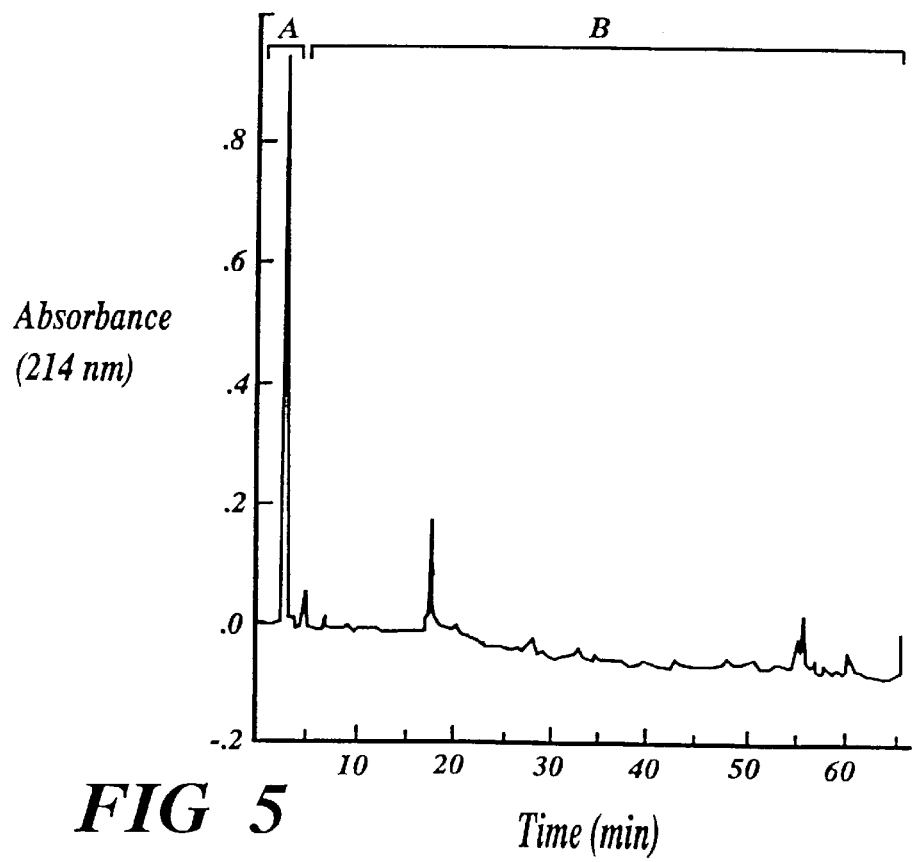
FIG. 5 shows reversed phase high performance liquid chromatography of affinity purified ovalbumin specific transfer factor.

The elution profiles of affinity purified transfer factors were obtained, a typical one being shown in FIG. 5. To obtain this, $23.3 \times 10^8$ ce of affinity purified albumin specific transfer factors, using rplc were applied in 50 ul volumes. All transfer factor activity eluted in unretained peak (fraction A), while contaminants were retained. Transfer factor activity was measured using the above mentioned footpad assay. Fraction A showed $17.33 \pm 1.20 \times 10^{-2}$ mm (p<0.001) swelling, fraction B (impurities) showed $5.5 \pm 1.61 \times 10^{-2}$ mm, with p being not significant.

EXAMPLE 13

The fraction A described above was assayed and showed only a 7% enrichment in specific activity. Yield, however, was 100%, as shown in Table I. These data were confirmed by studies which showed that rechromatography of lyophilized, reconstituted fraction A sample showed essentially the same unretained peak.

EXAMPLE 14

Fraction A type materials were obtained for ferritin specific transfer factor, just as ovalbumin specific transfer factor

TABLE I

Yield and Specific Activities for Purified Materials[1]

| Preparation | Units TF per $10^7$ ce | $AU_{214}$ per $10^7$ ce | $UNITS_{TF}$ per $AU_{214}$ | Total Cell Equivalents ce($10^{-8}$) | Total Units T.F. Activity ce($10^{-8}$) | Individual Yield (%) | Cumulative Yield (%) |
|---|---|---|---|---|---|---|---|
| Ovalbumin Transfer Factor | | | | | | | |
| Dialysate | 1.370 | 2.770 | 495 | 484 | 66.3 | — | — |
| Aff. Purified | 910 | 0.040 | 22,800 | 470 | 42.8 | 66 | 66 |
| Fraction A[2] | 910 | 0.037 | 24,600 | 465 | 42.3 | 100 | 66 |
| Fraction AIII[3] | 770 | 0.035 | 22,000 | 463 | 35.7 | 85 | 56 |
| Ferritin Transfer Factor | | | | | | | |
| Dialysate | 1.020 | 2.340 | 436 | 145 | 14.8 | — | — |
| Aff. Purified | 600 | 0.026 | 23,100 | 143 | 8058 | 59 | 59 |
| Fraction A[2] | 1,270 | 0.020 | 63,500 | 130 | 16.5 | 212 | 125 |
| Fraction AIII[3] | 600 | 0.080 | 33,300 | i23 | 7.38 | 47 | 50 |

[1] A unit of transfer factor activity is defined as the amount of transfer factor-containing sample (expressed in the number of mononuclear cell equivalents (ce) from which it was derived) required to produce a one-half maximal footpad swelling response. Specific activity is defined as the number of units of transfer factor activity per absorbance unit at 214 nm.
[2] Prepared using an ammonium bacarbonate-based reversed-phase high pressure liquid chromatography method.
[3] Prepared using gel filtration high pressure liquid chromatography columns in a polytypic application.

EXAMPLE 11

Affinity purified material, as described above, was subjected to chromatographic analysis using rplc incorporating 5 mM TBAP as ion pairing agent. "TBAP" refers to a 25 tetrabutylammonium phosphate based solvent system. In these experiments, $43.2 \times 108$ ces were applied in a 400 $\mu$l volume.

was obtained. This fraction showed 2.75 fold enrichment (Table I); however, there was an apparent two fold (212%) yield over affinity purified sample, and 125% yield relative to crude dialysate.

EXAMPLE 15

Figure 6A:
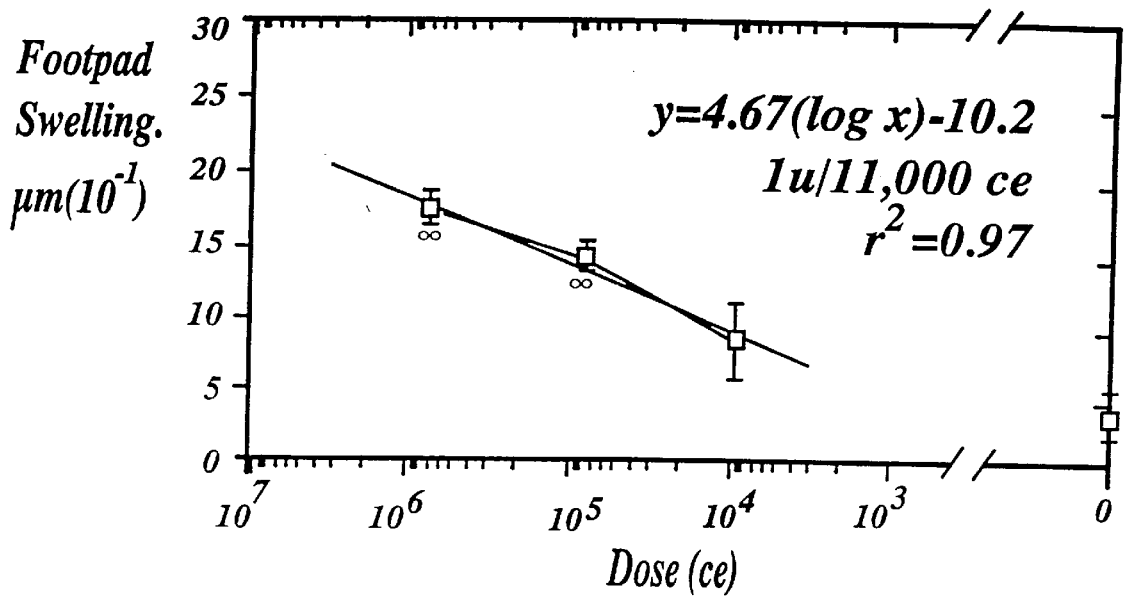
FIG. 6 shows dose response relationships for reversed phase high performance liquid chromatography purified transfer factor.
Figure 6B:
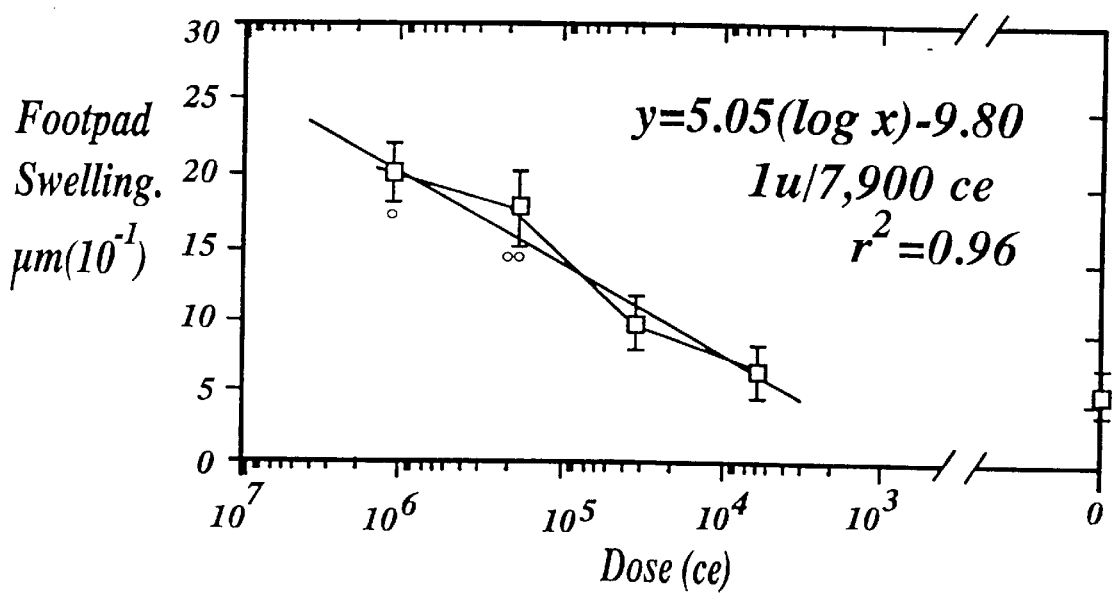

Dose response curves for the "fraction A" for both ovalbumin and ferritin specific transfer factors were obtained, as set out in Example 9. The results are depicted in FIGS. 6A and 6B (ovalbumin and ferritin, respectively). Coefficients of determination are 0.96 and 0.97, respectively.

EXAMPLE 16

Figure 7:
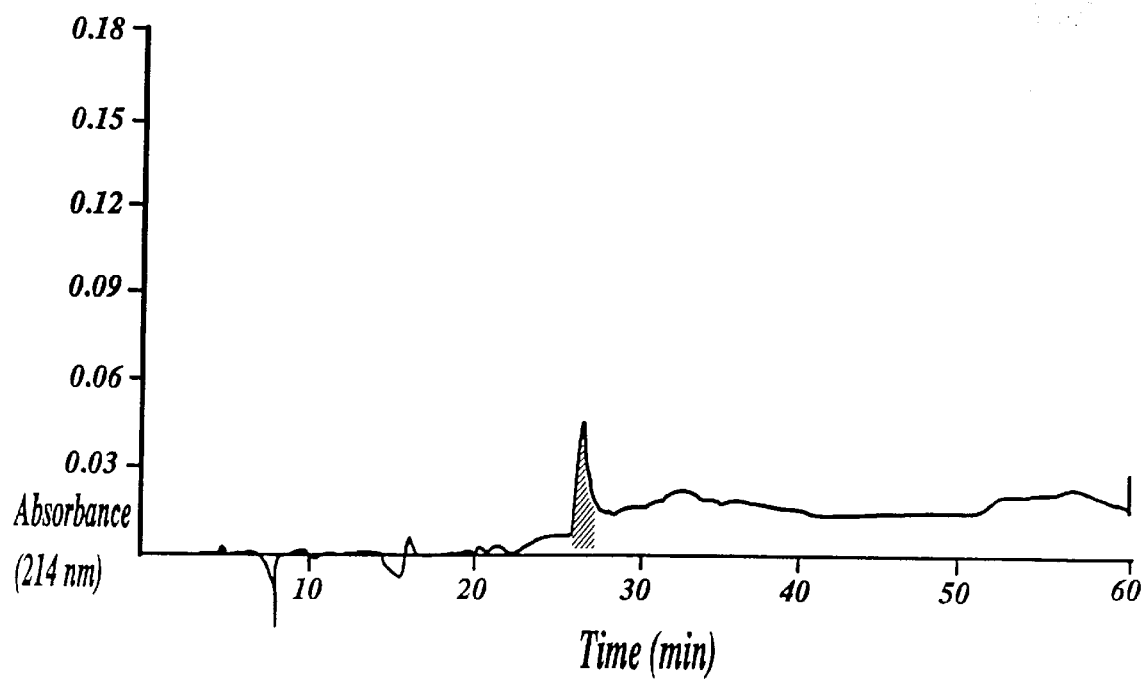
FIG. 7 depicts analysis of reversed phase high performance liquid chromatography fractions of ferritin specific transfer factor.

Fraction A ferritin specific transfer factor material was analyzed using a TBAP system. $10.5 \times 10^8$ ce were applied to the column in a 100 µl volume. The analysis, as indicated by FIG. 7, contained four components which eluted at 4.7, 16.1, 21.3 and 26.4 minutes. Transfer factor activity was found in the last of these. After correcting for solvent baseline absorbance characteristics of the gradient, this corresponds to approximately 90% of the 214 nm absorbing material.

EXAMPLE 17

Figure 8:
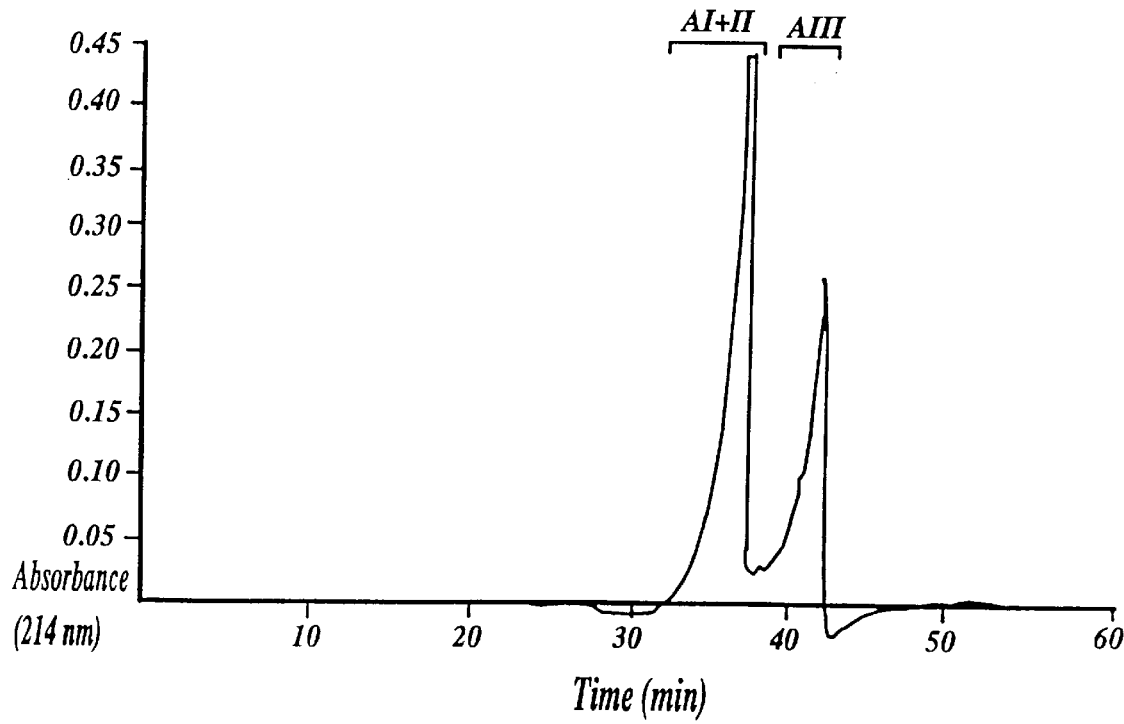
FIG. 8 presents polytypic chromatography of affinity and reversed phase high performance liquid chromatography purified transfer factor on gel filtration high performance liquid chromatography columns.

Fraction A material was purified further, using polytypic gel filtration high performance liquid chromatography. To do so, $25.4 \times 10^8$ ce were applied to the columns in volumes of 200 µl. The eluant was 10 mM formic acid, and an elution profile, for ferritin specific transfer factor fraction A is shown in FIG. 8. Fraction "AIII", i.e., the 3rd fraction to eluate, contained all of the transfer factor activity and was studied further.

EXAMPLE 18

Figure 9:
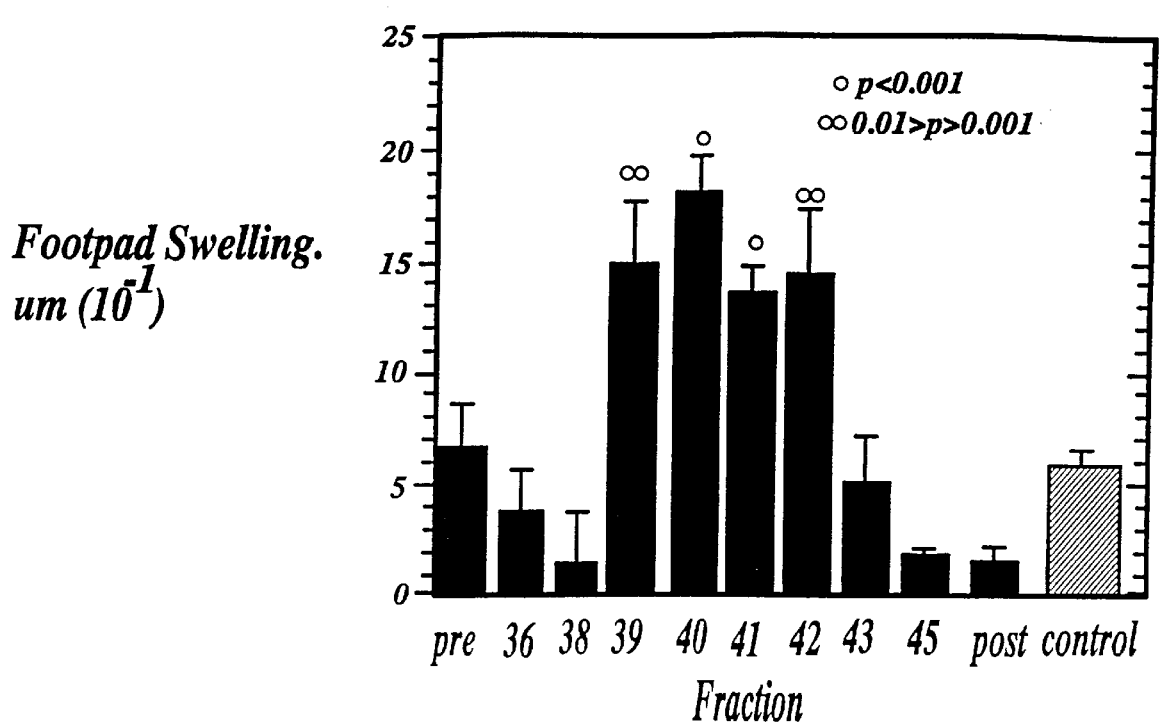
FIG. 9 presents activity data for transfer factor for ferritin, from individual fractions of polytypic gel filtration high performance liquid chromatography.

Ferritin specific transfer factor fraction AIII from the gel filtration high performance liquid chromatography was analyzed, by neutralizing 50 µl aliquots from individual fractions with 50 mM ammonium bicarbonate, and diluted with sterile, purified water to $1.8 \times 10^6$ ce/ml. Activity was analyzed for each fraction. "Pre" fractions represent a pool of fractions 24 through 32, and "post" fractions 47–60. Transfer factor activity was found only in fractions 39–42 (FIG. 9).

EXAMPLE 19

Figure 10A:
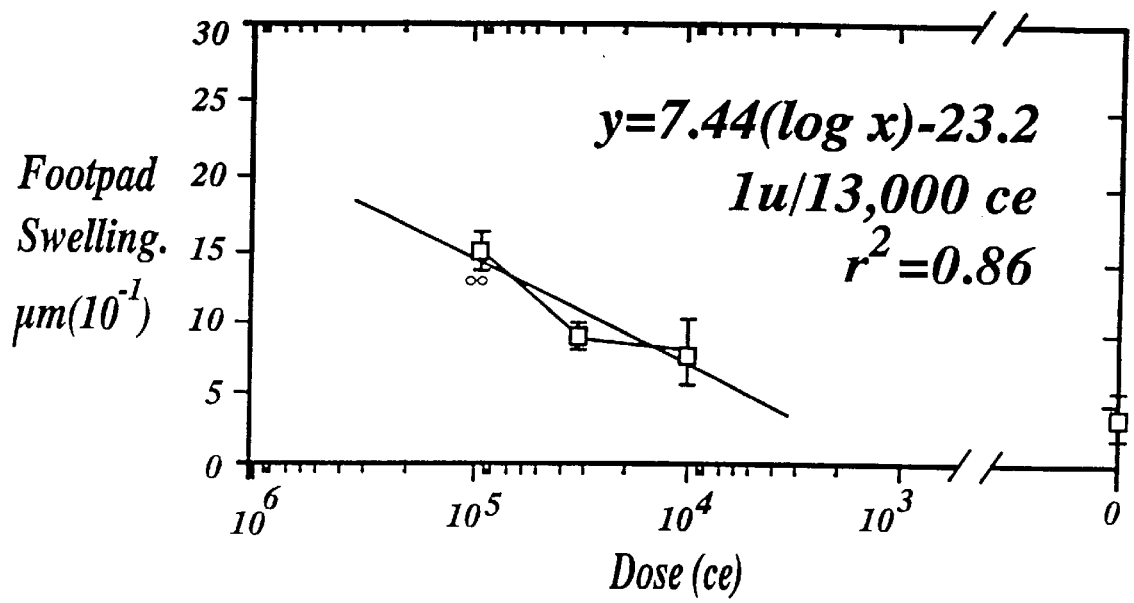
FIG. 10 shows dose response relationships for the fraction described in FIG. 8.
Figure 10B:
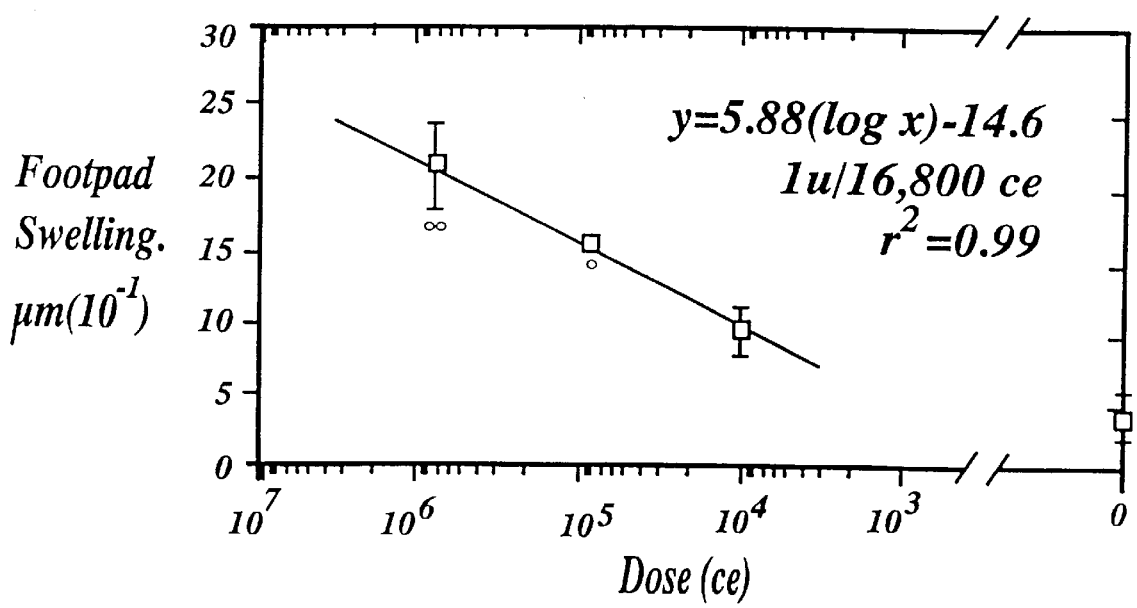

Dose response curves were derived for "Fraction AIII" materials (both types) as done in prior experiments. These results are shown in FIGS. 10A and 10B for ovalbumin and ferritin specific transfer factor, respectively. For ovalbumin, the coefficient of determination, $r^2$, was 0.86, and one unit of activity per $1.3 \times 10^4$ ce. ferritin specific transfer factor showed $r^2$ of 0.99, and one unit per $1.68 \times 10^4$ ce. These results lead to the conclusion that spleens from mice given a single sensitizing dose of antigen and containing 0.5 to $2.0 \times 10^8$ mononuclear leukocytes would yield $3.8 \times 10^3$ to $1.5 \times 10^4$ units of transfer factor for ovalbumin. The data for ferritin would suggest $3 \times 10^3$ to $1.5 \times 10^4$ units for comparable mice, wherein the purification scheme of FIG. 1 is used.

Specific activity of the ovalbumin specific fraction was 11% less than the fraction A material, but the yield was 85%, suggesting 44 fold enrichment. With respect to the ferritin specific fraction, specific activity was 48% lower than fraction A, but 1.4 fold higher than affinity purified material, and 76 fold higher than the dialysate. Yield was 47%, giving a cumulative yield of 50%.

EXAMPLE 20

Figure 11:
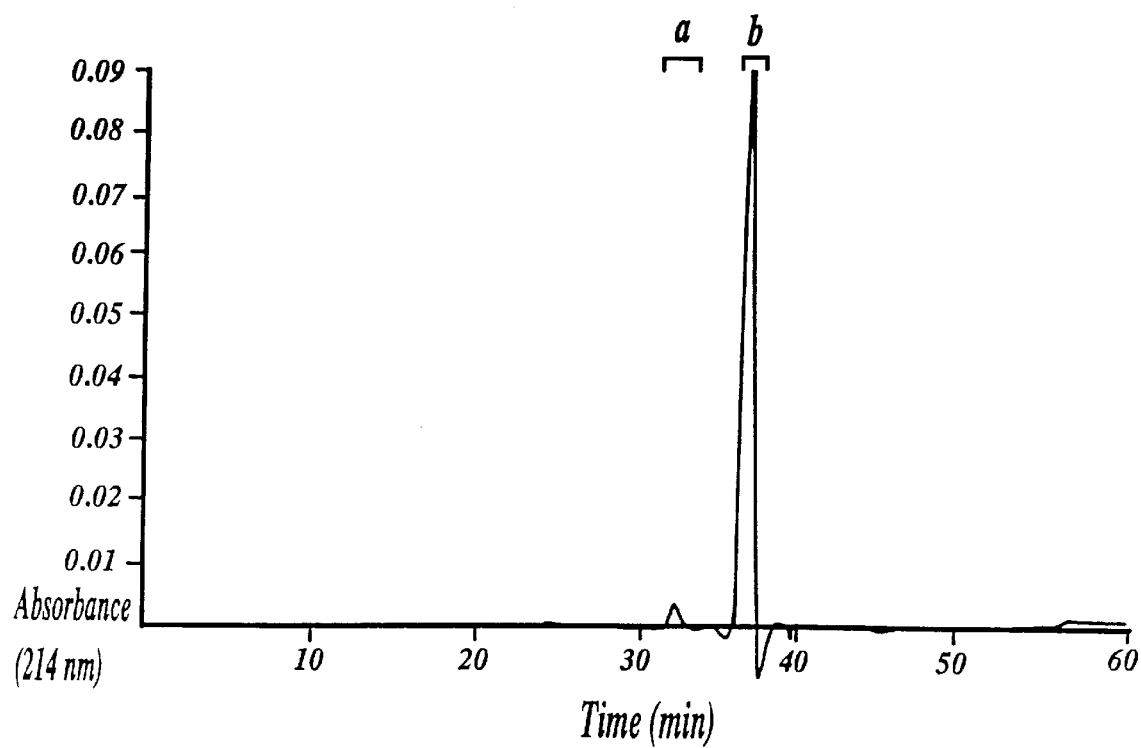
FIG. 11 presents gel filtration chromatography of a transfer factor fraction as in FIG. 8.

The gel filtration high performance liquid chromatography method of Meyerson et al[48] was used to analyze the purity of Fraction AIII as well as to determine the molecular weight of transfer factor. An elution profile of Fraction AIII material applied to this system is shown in FIG. 11. Two peaks were observed, with the major chromophore (peak b) representing 98% of the 214 nm-absorbing material as quantified by integrated peak area. As low recovery is frequently observed when very small quantities of proteins are subjected to conventional dialysis, therefore material from each peak was desalted by a modification of the microdialysis method reported by Overall[49] prior to in vivo assay for transfer factor activity. In pilot experiments, use of this technique resulted in quantitative recovery of transfer factor activity (data not shown). After microdialysis, samples were brought to a concentration of $4 \times 10^7$ ce per ml and tested for transfer factor activity. Activity was detected only for material in peak b.

Figure 12:
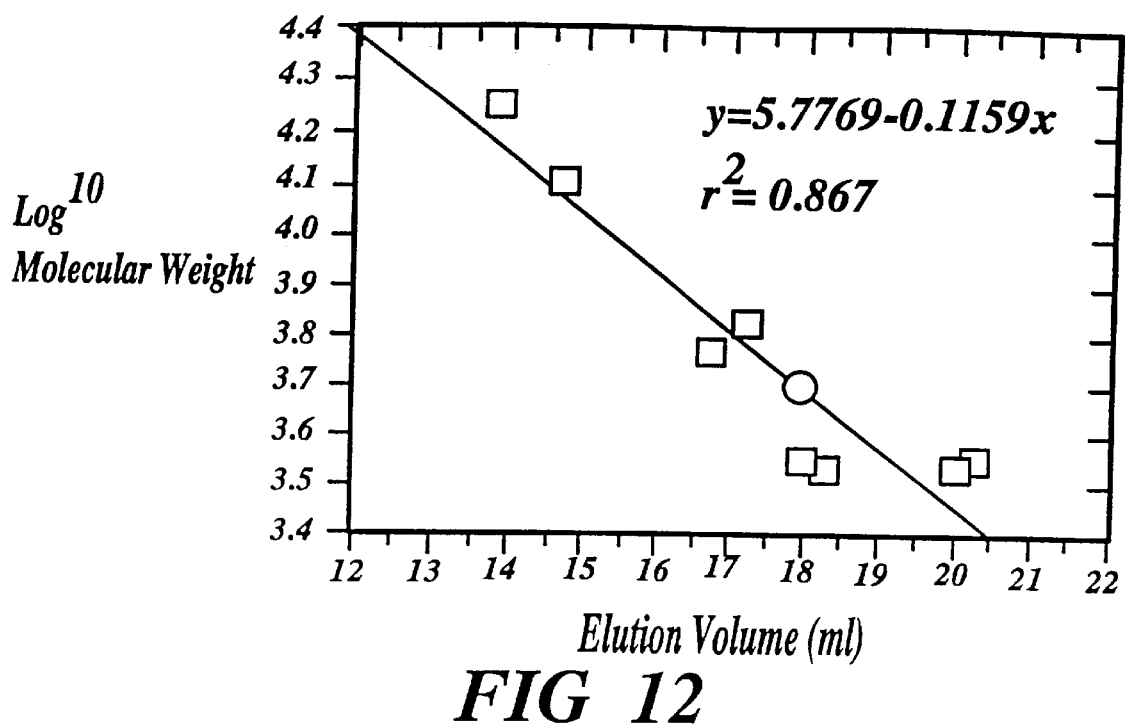
FIG. 12 shows a standard curve obtained from gel filtration chromatography of molecular weight markers.

This system was used to obtain a standard curve (of the form $\log_{10}$ molecular weight=5.7769–(0.1159)(elution volume); $r^2=0.87$; FIG. 12), the data for which were obtained by applying 8 individual molecular weight markers in separate runs. Chicken egg albumin was used to determine the void volume of the system (12.0 ml), while acetone was used to determine the total permeation volume (22.5).

The retention time of peak b was used to determine an elution volume (17.98 ml), which was in turn used to calculate a relative molecular mass for transfer factors of 4,900 Daltons. Transfer factor activity for ferritin specific material coincided with elution volume of 17.98 ml (fraction b). Footpad responses by recipients of $4 \times 10^7$ ce for fraction a were $5.83 \pm 2.31 \times 10^{-2}$ mm (p is insignificant) and $19.50 \pm 1.82 \times 10^{-2}$ mm (p<0.001) for fraction b. The peak representing fraction b contains 98% of the 214 nm absorbing material.

To determine molecular weight, the same system was used to obtain the standard curve shown in FIG. 12, for which data were obtained by using molecular weight markers in separate runs. The analysis yields an estimated molecular weight of transfer factor of about 4900 to about 5500 Daltons.

EXAMPLE 21

Spectral Data for purified transfer factors

Figure 13:
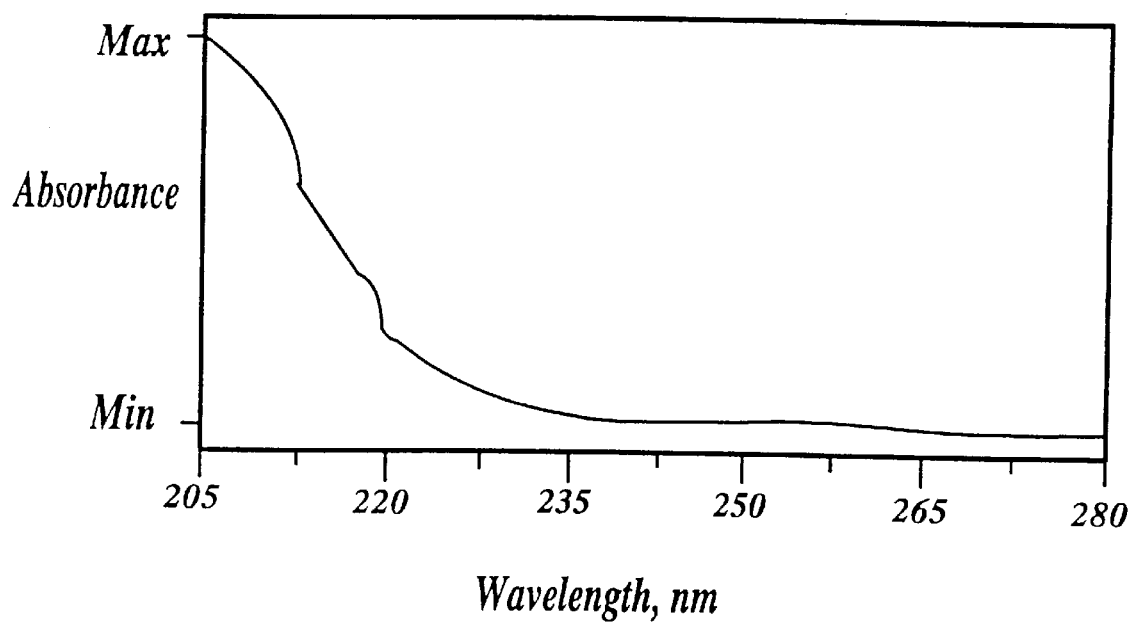
FIG. 13 shows the UV absorbance spectrum of a ferritin specific transfer factor.

An ultraviolet spectrum taken at the maximum of peak b (corrected for solvent absorbance) is shown in FIG. 13. These data, obtained from $2.5 \times 10^8$ mononuclear cell equivalents of material, show relatively little absorbance at wavelengths greater than 235 nm, including wavelengths classically used to monitor transfer factor purifications, such as 254 nm, 260 nm, and 280 nm. In fact, transfer factors have approximately 100-fold greater absorbance at 214 nm than at 254 or 280 nm. Thus, chromatography solvents which permit the use of low wavelengths, such as 214 nm, appear to provide substantial benefit in the sensitivity of transfer factor detection when monitoring chromatography using ultraviolet spectrophotometers.

EXAMPLE 22

Figure 14:
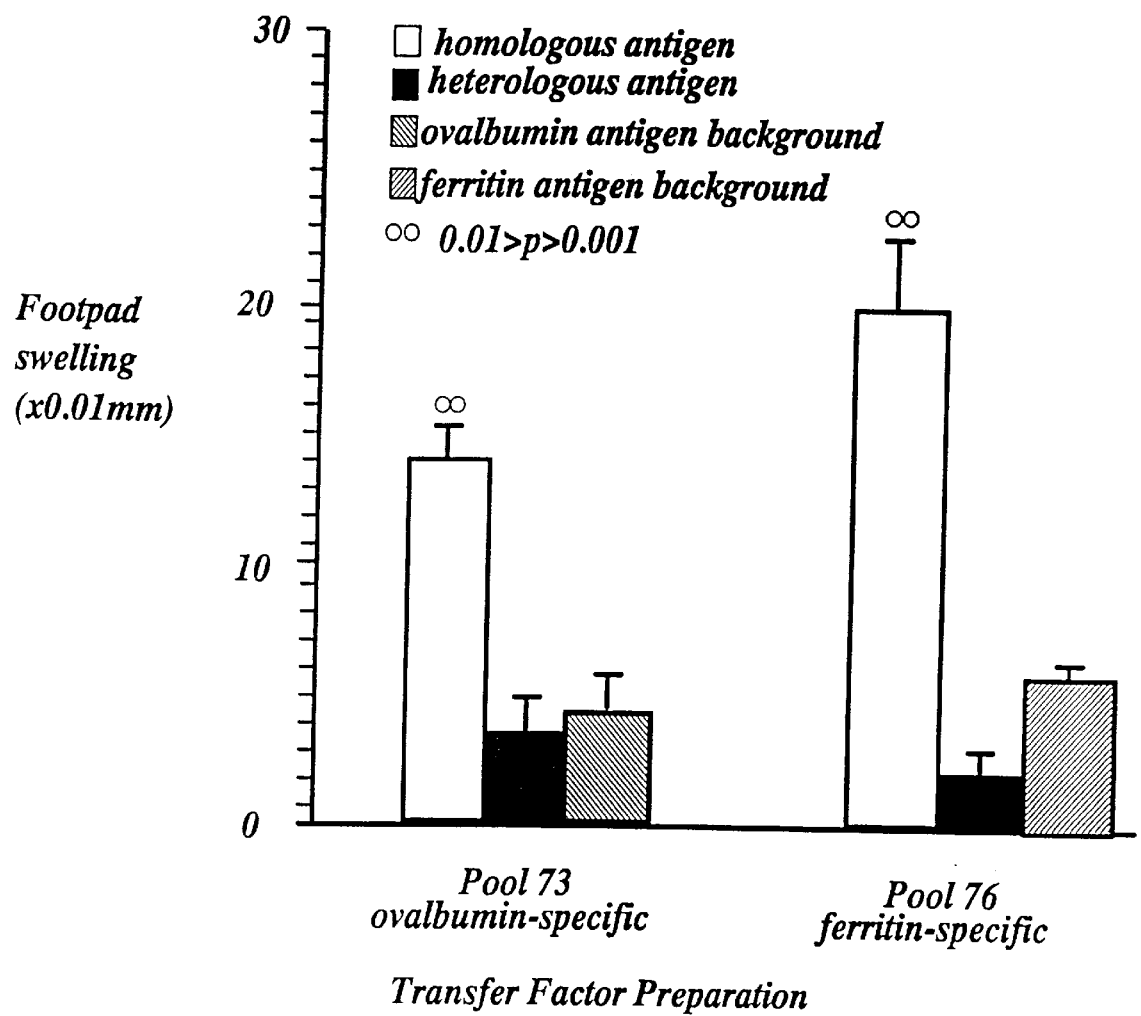
FIG. 14 depicts antigen specificity for highly purified transfer factor.

Antigen specificity of the purified AIII fraction transfer factors was studied. Mice were injected with a transfer factor preparation produced in response to one of either ovalbumin or ferritin ($10^6$ ce in 1.0 ml) followed by challenge 24 hours later with ovalbumin and ferritin. Neither preparation induced response to the heterologous antigen, but both showed the delayed hypersensitivity reaction with the homologous material indicating that the transfer factor retained antigen specificity (FIG. 14).

The transfer factor-containing dialysates described herein showed very similar specific activity (ovalbumin: 495 units at 214 nm; ferritin: 436 units at 214 nm), indicating extremely potent preparations. The data of Table 1 suggest that the spleen of one sensitized mouse, containing about $10^8$ mononuclear leukocytes, produces enough transfer factor to transfer significant delayed type hypersensitivity to at least 1000, and perhaps as many as 10,000 unsensitized recipients.

The affinity purification step, i.e., where transfer factor is reacted with its antigen, causes a loss of about 40% of transfer factor activity, but enhances specified activity by about 50-fold. Thus the purified transfer factor is extremely specific and very active.

Affinity purified transfer factor, when used in an $NH_4HCO_3$ based system, was eluted in void volume eluate, indicating the highly polar nature of the material. Data obtained for affinity purified ovalbumin specific transfer factor shows a slight increase in specific activity, and no loss of active material. The ferritin specific transfer factor gave less predictable results. The 2.75 fold increase in specific activity, taken with an apparent yield of 213%, coupled with decrease in ultraviolet absorbency, may suggest, inter alia, that an inhibitor of the transfer factor was removed. Indeed, Rozzo et al., Borkowsky et al., and Gottlieb, suggest existence of such factors.[50,51,52]

It has been noted that earlier work postulated an oligonucleotide residue as part of the transfer factor molecule. While it is possible that the described process removed this residue, it would not account for the absence of significant 280 nm absorbance, nor would it account for the retention of biological activity. Thus, it appears that antigen specific transfer factors are peptide molecules having a molecular weight of from about 4900 to about 5000 Daltons. These transfer factors are produced in sensitized animals in extremely small, but extremely potent amounts.

EXAMPLE 23

Amino acid composition analysis of purified transfer factor

Purified transfer factors were analyzed to acquire information on the characteristics and properties of these molecules. Samples of Fractions III (from polytypic chromatography on Sephadex G-10) and Fractions AIII (from polytypic high performance liquid chromatography) were used for this purpose. Whenever possible, nondestructive methods requiring a minimal amount of sample handling and providing high sensitivity were applied. This was important due to the small physical quantity of material available and the need, in some cases, to preserve biological activity.

Amino acid composition analysis, reduction and alkylation followed by chromatographic analysis and mass spectroscopy, gel filtration high performance liquid chromatography, SDS-polyacrylamide gel electrophoresis, and ultraviolet spectral analysis were performed to examine the purity and molecular characteristics of transfer factors. The antigen specificity of responses by recipients of purified transfer factors was studied as well.

Several strategies were used in efforts to obtain primary structure information. This was followed by a series of peptide mapping experiments using cyanogen bromide, trypsin or V8 protease to effect cleavage, followed by microbore high performance liquid chromatography. Amino acid sequence analysis was performed on the products of these experiments.

A sample of ferritin-specific Fraction III material comprised of a corrected value of $5.3 \times 10^8$ ce was subjected to amino acid composition analysis. The results are shown in Table II. The results are consistent with a proteinaceous nature for transfer factors, consisting of 65% polar amino acids. The data suggest that approximately 0.5 pmol of transfer factor is obtained from $10^8$ mononuclear cells.

The data were transformed to mole fraction values through normalization to the molar content of phenylalanine. Based on mole fraction values, a molecular weight of approximately 5,500 Daltons is predicted for transfer factors.

Potency of purified transfer factors. Since approximately 6,000 units of ferritin transfer factor activity are obtained from $1 \times 10^8$ mononuclear splenocytes (Table II), and approximately 0.5 pmol of transfer factors are obtained from $10^8$ ce, the results suggest quantities of transfer factor on the order of $10^{-16}$ moles are sufficient to induce significant sensitivity for expression of DTH responsiveness. The results underscore the high biological potency of transfer factors.

TABLE II

Amino Acid Composition Analysis of a Ferritin Transfer Factor-containing Fraction III

| Amino Acid | Quantity (pmol) | No. of Residues[1] | Contribution to molecular mass |
|---|---|---|---|
| Asx | 2.3 | 1 | 133 |
| Glx | 10.7 | 3 | 440 |
| S | 22.0 | 6 | 522 |
| G | 44.4 | 12 | 685 |
| H | 5.8 | 2 | 274 |
| R | 7.5 | 2 | 312 |
| T | 13.8 | 4 | 404 |
| A | 19.0 | 5 | 355 |
| P | 5.89 | 2 | 194 |
| Y | 10.4 | 3 | 490 |
| V | 7.9 | 2 | 198 |
| M | 8.8 | 2 | 262 |
| I | 5.4 | 2 | 226 |
| L | 17.2 | 5 | 566 |
| F | 3.6 | 1 | 147 |
| K | 6.7 | 2 | 256 |
| Totals[2] | 191.3 | 54 | 5482[3] |

[1]Data was normalized to phenylalanine.
[2]W and C are destroyed during hydrolysis and are not included.
[3]Adjusted for 1 mol water for non-peptidyl residues.

EXAMPLE 24

Chromatographic analysis of reduced and alkylated transfer factor

Figure 15A:
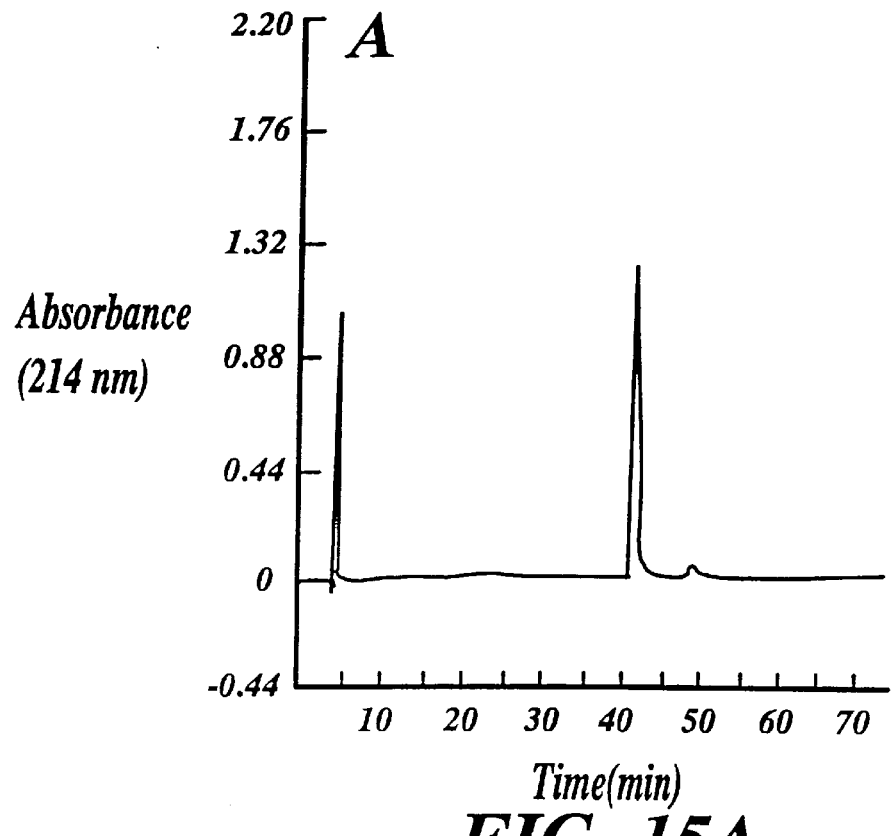
FIG. 15A shows the elution profile from a reduction and alkylation blank sample.
Figure 15B:
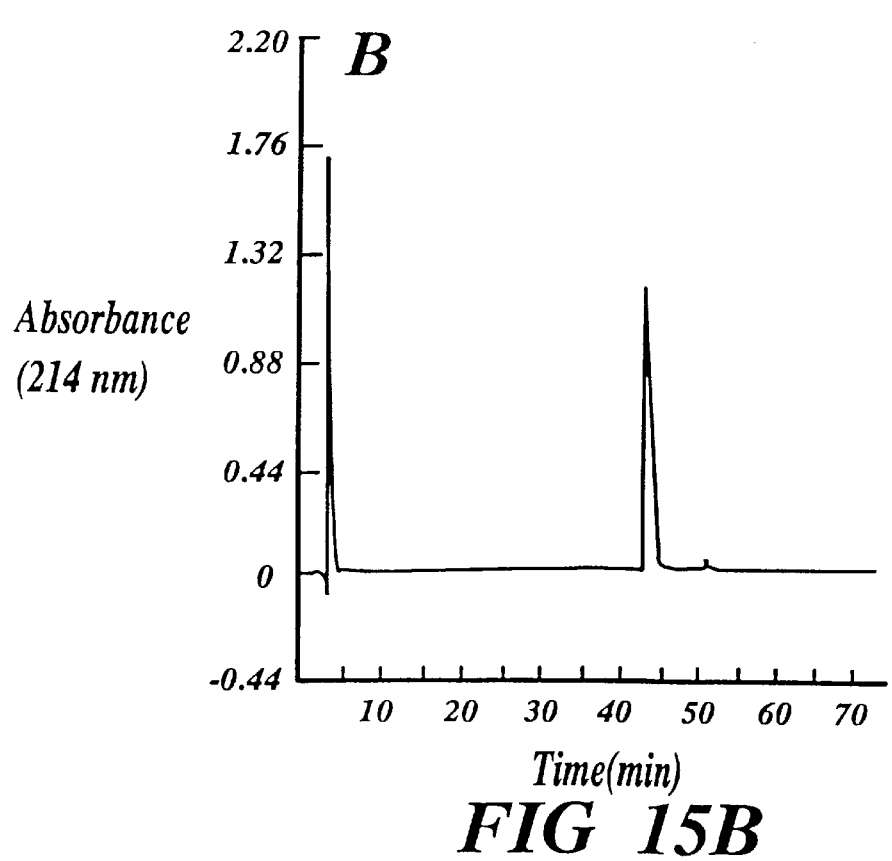
FIG. 15B shows the elution profile from a reduction and alkylation sample of transfer factor.

Fraction III ferritin-specific transfer factor was reduced and alkylated using dithiothreitol and 4-vinylpyridine, respectively, to obtain structural information. The reduced and alkylated sample was applied to an high performance liquid chromatography column containing an octadecylsilane matrix. Elution was accomplished using 5.0 mM ammonium bicarbonate as starting solvent and incorporating a linear gradient from 0 to 60% acetonitrile. FIG. 15A shows the elution profile from a reduction and alkylation blank sample, whereas FIG. 15B shows that of a reduced and alkylated Fraction III transfer factor. The unretained peak was significantly larger for the reduced and alkylated Fraction III than for the blank sample. There were no other apparent differences between the two chromatograms.

The elution of reduced and alkylated Fraction III in the unretained fraction from the ammonium bicarbonate-based reversed-phase high performance liquid chromatography system (FIG. 15B) is consistent with a lack, or small increase, in hydrophobicity.

Figure 16A:
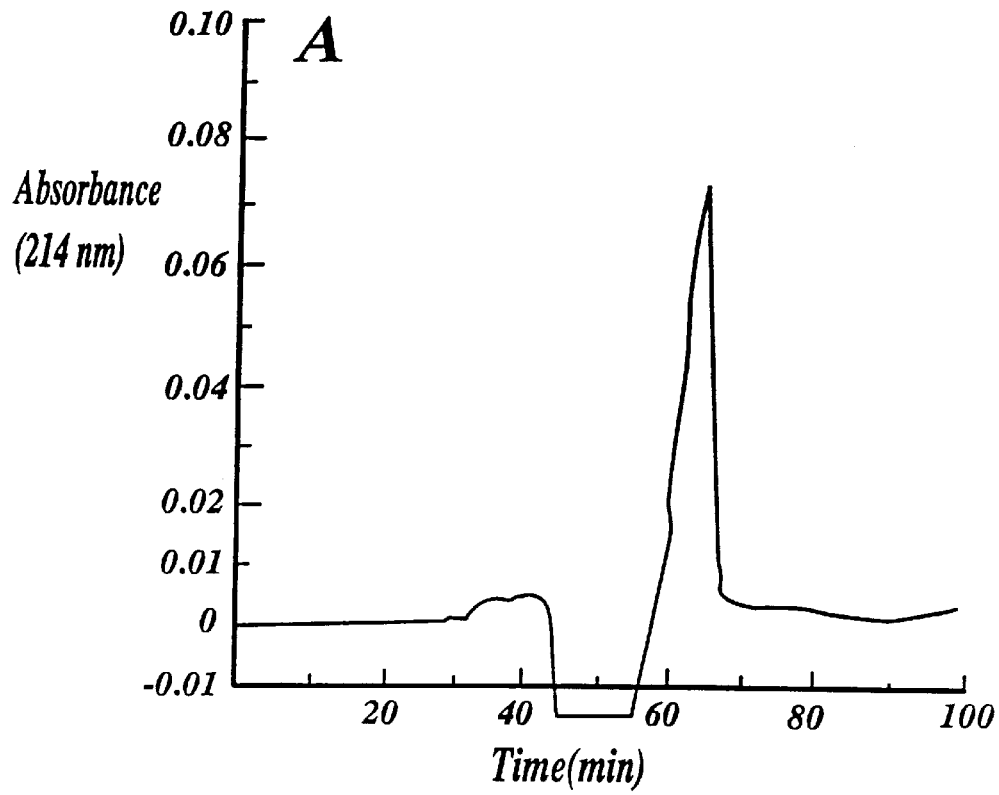
FIG. 16A shows a Sephadex G10 elution profile for control sample
Figure 16B:
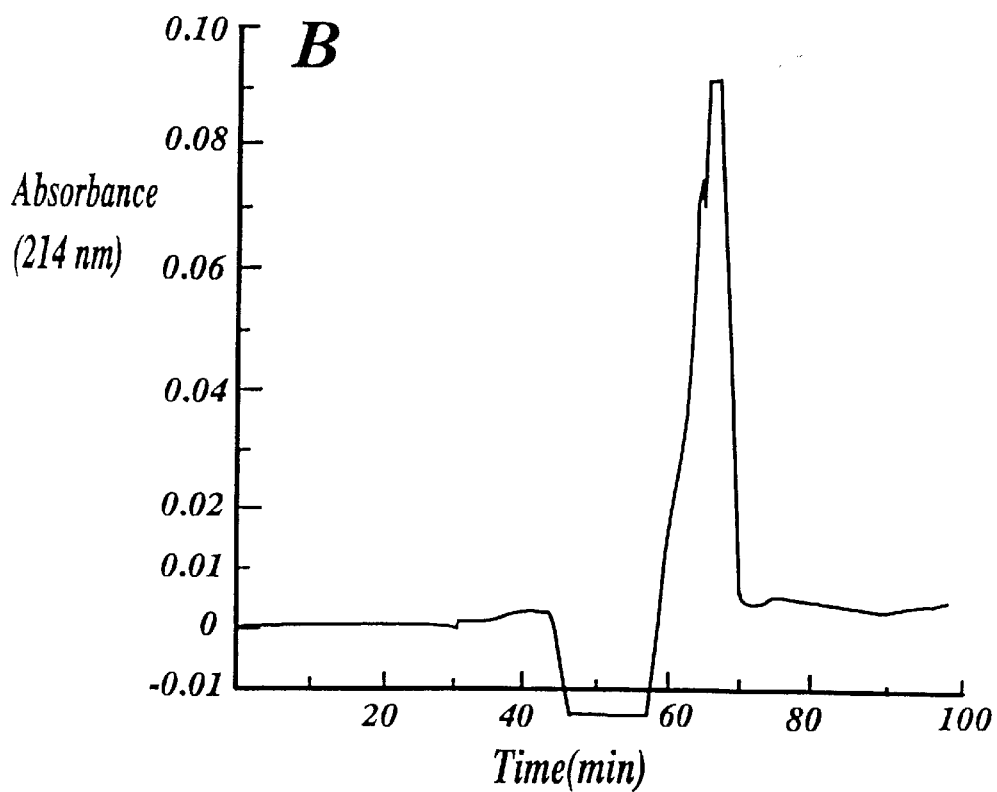
FIG. 16B shows a Sephadex G10 elution profile for Fraction III transfer factor.

The unretained peaks were collected and applied individually to the Sephadex G10 chromatography system. FIGS. 16A and 16B show the elution profiles for the control and Fraction III samples, respectively. A single unique peak was observed for the experimental sample (tR=67.60 min.).

The application of the unretained fraction to the Sephadex G-10 system resulted in the appearance of a single, retained peak (FIG. 16B) relative to the blank (FIG. 16A). There appears to be a shift in the retention time for the reduced and alkylated Fraction III relative to native Fraction III.

EXAMPLE 25

SDS—Polyacrylamide gel electrophoresis analysis of purified transfer factors

Figure 17:
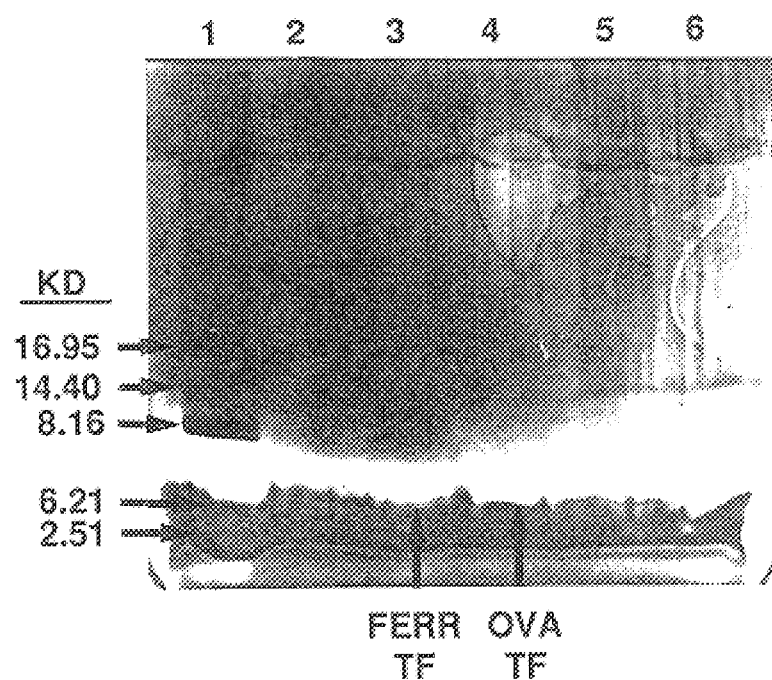
FIG. 17 shows an SDS-polyacrylamide gel electrophoresis profile of transfer factor under non-reducing conditions.

SDS-polyacrylamide gel electrophoresis analysis of Fraction AIII materials was performed under non-reducing conditions. The results, shown in FIG. 17, support those observed using analysis by gel filtration chromatography. A single band was observed for each preparation following overdevelopment using silver staining. Both preparations produced bands which were "negatively" stained and had identical migration distances into the separating gel, although the band for ovalbumin-specific transfer factor was more prominent than that for ferritin-specific transfer factor. The apparent relative paucity of amino acids capable of reducing the silver from the ionic to the metallic state induced us to subsequently stain the gel using Coomassie Blue R-350. This resulted in development of a positive image surrounded by a clear zone for ovalbumin-specific transfer factor, but some decrease in the band/background contrast for the less-prominent ferritin-specific transfer factor band. The results are indicative of a relative molecular mass of 5,400 Daltons for both transfer factors and indicate a high degree of purity for each preparation.

EXAMPLE 26

Peptide mapping of transfer factors and purification of cleavage fragments.

Peptide mapping for transfer factors was done using CNBr to cleave transfer factors. Either ferritin-specific or ovalbumin-specific Fraction AIII transfer factor was dissolved in acidic solution and CNBr was added. Following incubation, the reaction mixtures were lyophilized, reconstituted, and applied to reversed phase microbore high performance liquid chromatography. A linear gradient from 0.1% TFA in water to 50% acetonitrile in water was used for this purpose. No significant unique peaks were observed in experimental samples relative to the blank.

Figure 18A:
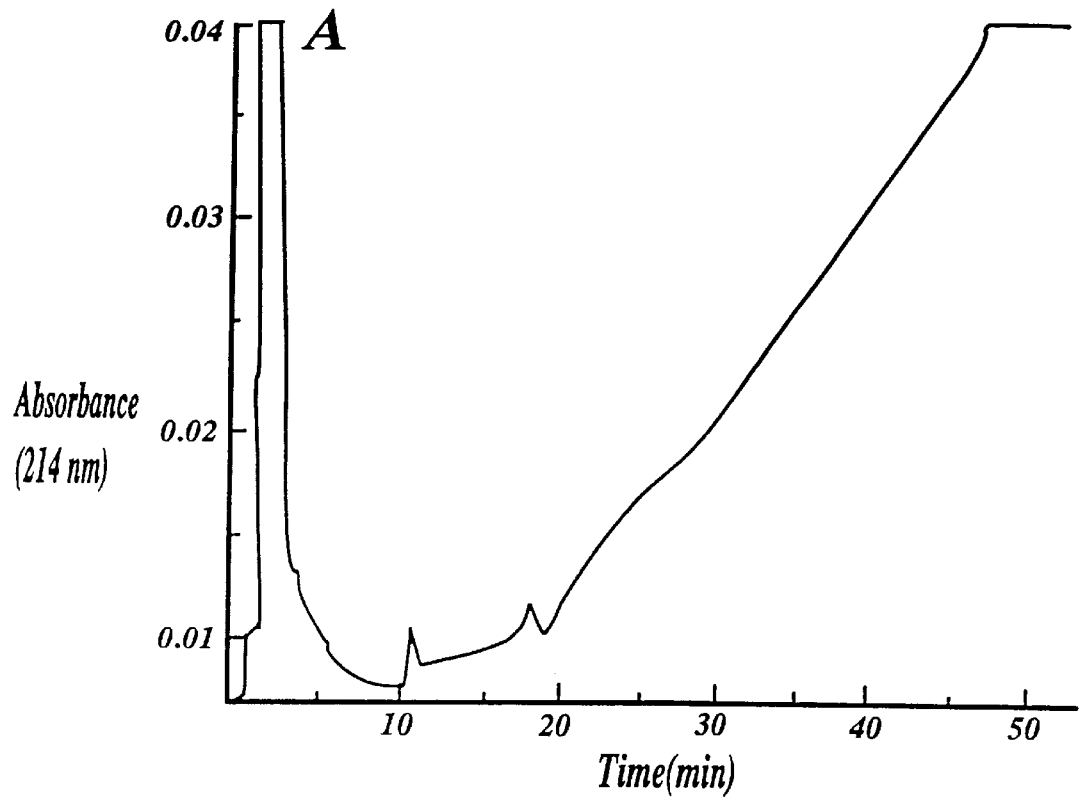
FIG. 18A is the control elution profile for the trypsin digestion of transfer factor.
Figure 18B:
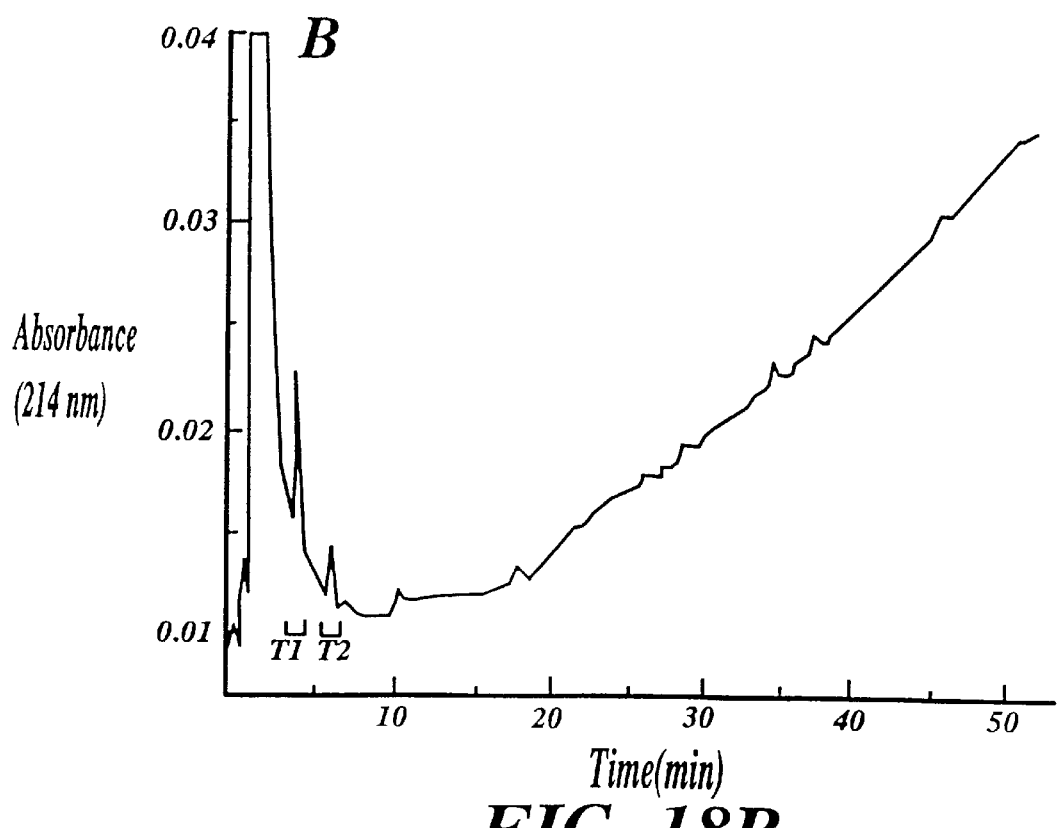
FIG. 18B shows elution profiles for Fraction AIII ferritin-specific transfer factor after trypsin digestion.

Fraction AIII ferritin-specific transfer factor was incubated in the presence of trypsin in order to perform peptide mapping. Elution profiles from microbore reversed phase high performance liquid chromatography of the reaction mixtures are shown in FIG. 18. Two unique peaks were observed for the transfer factor containing sample (FIG. 18B) relative to the control sample (FIG. 18A). No amino acid sequence data was obtained from materials from either of these peaks.

Either ferritin-specific or ovalbumin-specific Fraction AIII transfer factors, or chromatographic effluent control samples, were dissolved in a solution of ammonium bicarbonate and sodium dodecyl sulfate. V8 protease was added to these solutions, and the solutions were incubated for 18 h. Following incubation the samples were applied directly to a 1.0×100 mm reversed-phase microbore high performance liquid chromatography column containing an octadecylsilane packing. Elution was performed using a linear gradient of 5 mM ammonium bicarbonate containing 0.01 % (W/v) SDS as starting solvent and an acetonitrile/5 mM ammonium bicarbonate solution (60:40;V/v) containing 0.01% (W/v) SDS as final solvent.

Figure 19A:
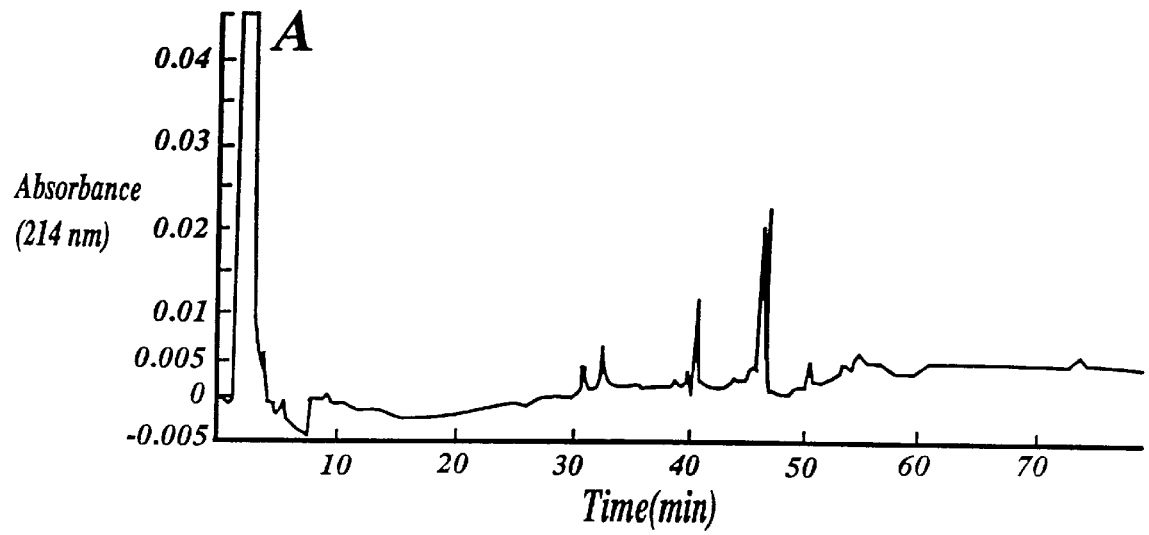
FIG. 19A is the control elution profile of transfer factor digested with V8 protease.
Figure 19B:
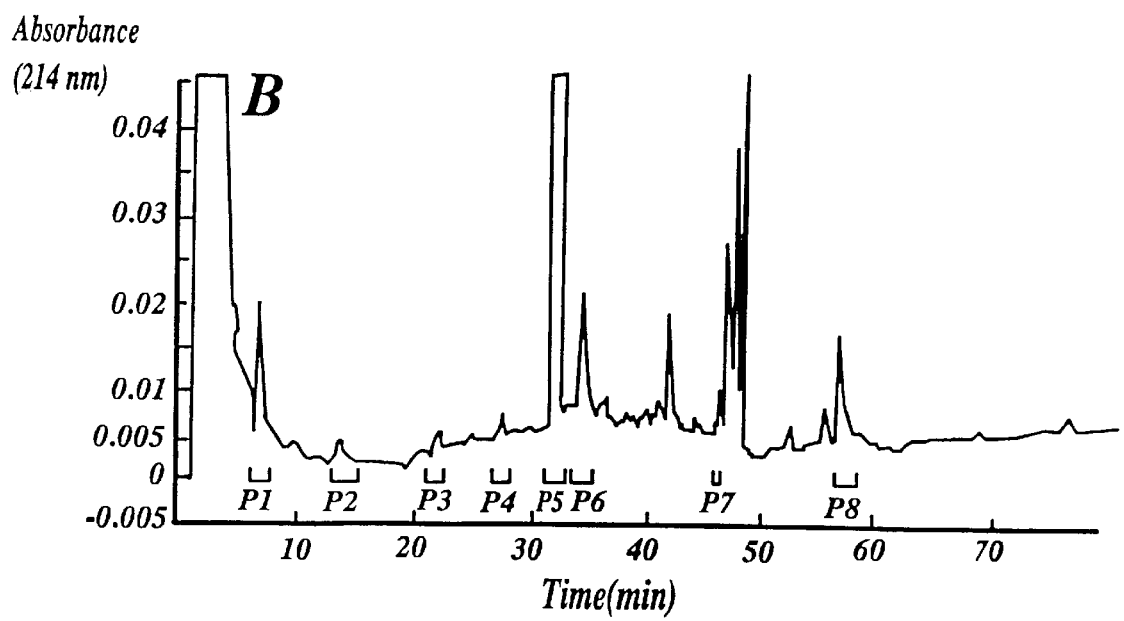
FIG. 19B is the elution profile of chicken egg albumin-specific transfer factor digested with V8 protease.
Figure 19C:
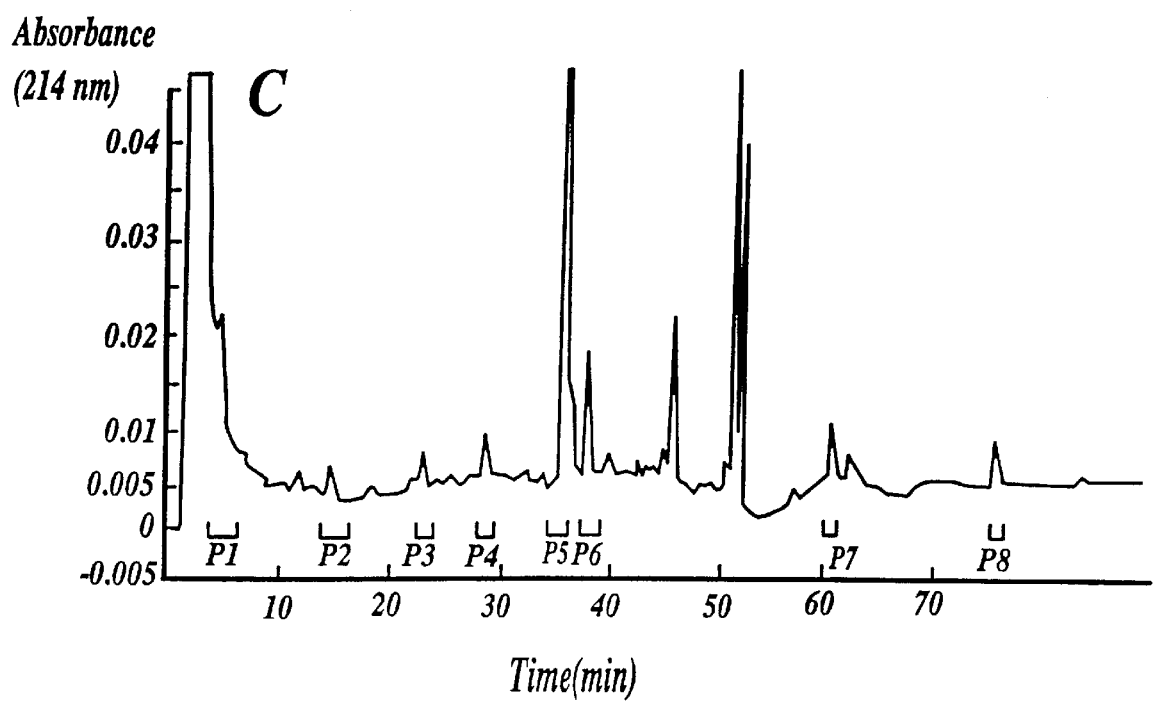
FIG. 19C is the elution profile of ferritin-specific transfer factor digested with V8 protease.

Elution profiles obtained from these experiments are shown in FIG. 19. V8 protease digests of 3 effluent controls for ferritin-specific transfer factor and 2 effluent controls for ovalbumin-specific transfer factor were analyzed using microbore high performance liquid chromatography. Essentially identical results were obtained for all five control samples. Eight transfer factor-derived peaks were observed for a chicken egg albumin-specific transfer factor digest (FIG. 19B) and ferritin-specific transfer factor digest (FIG. 19C) when compared to effluent controls (FIG. 19A). Comparing the transfer factor elution profiles to one another, three peaks were common to both preparations while 5 others were not (Table III). Of the 5 peaks, 4 appeared to have distinct, but similar, retention times, and appeared to be similar in their relative positions within each chromatogram. Each preparation produced one peak which appeared completely unrelated in its retention characteristics compared to any in the other preparation.

TABLE III

Retention Times for V8 Protease Digests of Purified Transfer Fragments

| Peak Designation | Retention Time (min) |
| --- | --- |
| Ovalbumin-Specific Transfer Factor Fraction AIII | |
| p1 | 7.0[4] |
| p2 | 13.9[1] |
| p3 | 21.6[2] |
| p4 | 26.6[3] |
| p5 | 30.6[5] |
| p6 | 33.3[6] |
| p7 | 44.9[8] |
| p8 | 55.3[7] |
| Ferritin-Specific Transfer Factor Fraction AIII | |
| p1 | 4.6[4] |
| p2 | 13.6[1] |
| p3 | 21.0[2] |
| p4 | 26.0[3] |
| p5 | 32.2[5] |
| p6 | 34.1[6] |
| p7 | 53.7[7] |
| p8 | 67.0[9] |

[1,2,3]common peaks
[4,5,6,7]potentially-related peaks having similar, but distinct, chromatographic mobility
[8,9]peaks having unique chromatographic motility As has been shown, the prior art molecules consisting of peptide and oligonucleotide have been implicated in treatment of many pathological conditions. It has been shown herein that the purified proteinaceous transfer factor does transfer the delayed type hypersensitivity to a specific antigen. Thus, the invention embraces the treatment of pathological conditions where an immune response is needed or an immune deficiency must be corrected via administering an amount of the transfer factor to a non-sensitized individual in an amount sufficient to provoke expression of cell mediated immunity against an antigen.

EXAMPLE 27

Treatment of chronic or recurrent *Herpes simplex* infections with Herpes-specific transfer factor Subjects for this treatment have culture-proved cutaneous, labial and/or genital infections with HSV-1 or HSV-2. The dosage for recipients of transfer factor extracted from immune lymphocytes is $5 \times 10^8$ lymphocyte equivalents. This is approximately 50 ng of substantially pure transfer factor prepared according to the protocol outlined in Examples 1 through 20 herein. Recipients of synthesized transfer factor receive approximately 50 ng of material at each treatment. All preparations have potency testing by the quantitative footpad swelling assay described above. The injections are given monthly. Monitoring of responses is done with a lesion and symptom score card and by monitoring cell-mediated immune responses to *Herpes simplex* antigens.

EXAMPLE 28

Treatment of chronic mucocutaneous candidiasis with specific transfer factor

The general protocol is modeled after that used by Kirkpatrick and Greenberg.[53] The subjects are first treated with an antifungal agent such as amphotericin B, fluconazole, or Ketoconazole to reduce the burden of infecting organisms.

Specific transfer factor therapy with material extracted from immune lymphocytes requires a dosage of $6 \times 10^8$ lymphocyte equivalents. This dosage translates into approximately 60 ng of purified transfer factor and this is the dosage that is used for synthetic transfer factor. Patients receive this dosage monthly for months 1, 2, 3 and 4; then every other month for months 6, 8, 10, and 12. Subsequently, treatments with the same dosage are given at 4 month intervals to maintain remission.

EXAMPLE 29

Treatment of mycobacterial and fungal infections with transfer factors

The rationale for use of an immunologically oriented therapy in these patients is based on the observations that cell-mediated immunity and microbiocidal activity may be deficient. The mechanisms producing the immune deficiency are only partially understood and it is probable that there are somewhat different mechanisms in patients with different infections.

Treatment with specific transfer factor employs $5 \times 10^8$ lymphocyte equivalents (50 ng of substantially pure transfer factor) per dosage. Treatment with synthetic transfer factors employs 1.2 pgm of material that is specific for the infection that affects the patient. The actual dosage of each lot is determined by a potency assay using the quantitative foot pad assay. Treatments are administered at monthly intervals and continued until the infection is cured.

EXAMPLE 30

Preparation of *Herpes-simplex* Virus Type-1 Specific Transfer Factor

A. Preparation of *Herpes simplex* virus

A clinical isolate of *Herpes simplex* virus type-1 (HSV-1) was propagated on human embryonic lung fibroblasts. The cells were collected by centrifugation and disrupted by sonication. The cellular debris was collected by centrifugation and the cell-free supernatant that contained the virus particles was aliquoted and stored at $-80°$ C. After at least 24 hours at $-80°$ C. an aliquot of the virus suspension was thawed and serial dilutions were used to infect monolayers of human embryonic lung fibroblasts to determine the number of plaque-forming units (pfu) of infectious virus per ml of suspension.

B. Preparation of HSV-1 for immunization and skin testing

The purpose of this procedure is to prepare non-infectious virus that can be used to immunize donor animals for production of *Herpes simplex*-specific transfer factors and for testing immune donors for delayed-type hypersensitivity to antigens of *Herpes simplex*.

Suspensions of infectious virus were exposed to ultraviolet light (Mineralite model R52G) at an energy of 2,200 µW/cm² (distance 7.6 cm) for 30 minutes. The virus suspension was in an ice bath during the exposure. This procedure totally eliminates infectivity, but does not alter immunogenicity of the virus preparations.

C. Immunization of Cattle

Virus suspensions were irradiated with ultraviolet light as described above. The suspension was emulsified into an equal volume of Freund's complete adjuvant. The emulsion was injected subcutaneously into the flanks of young adult cattle (Hereford or Holstein) of either sex and weighing 200–400 pounds (90–182 Kg). Typically, $2 \times 10^8$ pfu of virus in a volume of 2.0 ml was injected into 10 sites of 0.2 ml each.

D. Testing for delayed type hypersensitivity

Ultraviolet-irradiated *Herpes simplex* virus ($10^7$ pfu/ml) in a volume of 0.1 ml was injected intradermally into the skin of the neck of the animal. Appropriate controls such as diluent (usually Hank's balanced salt solution) and a suspension of another unrelated antigen were also injected into nearby sites. The inflammatory response was defined as the millimeters of induration that develop at the injection sites by 48 hours. A positive delayed type hypersensitivity (DTH) response is $\geq 5$ mm of induration.

E. Collection of HSV-1 specific transfer factors

1. Venous blood: Jugular vein blood was collected into 3.8% aqueous sodium citrate. The whole blood was diluted with an equal volume of Hank's balanced saline solution (HBSS) (without calcium or magnesium) and the cells were collected by centrifugation at 1,000×g for 30 minutes. The cells were washed twice with HBSS and collected by centrifugation at 1,000×g for 30 minutes.

2. Spleen cells: After several collections of venous blood, the cattle were euthanized with phenobarbital and the spleen was removed. A small portion (2–3 grams) was removed and a single cell suspension was made and the spleen cells were counted. This value was adjusted to the total weight of the spleen to provide an estimate of the total number of cells in the spleen. The spleen may be stored at $-20°$ C. until it is processed. To prepare spleen cell transfer factor, the spleen pulp was separated from the capsule by gentle scraping.

F. Processing of Transfer Factors

Venous blood or spleen cells were lysed by repeated cycles of freezing in a mixture of dry ice and ethanol and thawing at $37°$ C. Lysis was confirmed by microscopy. The transfer factors were separated from macromolecules by dialysis through boiled Spectra/por 1 dialysis membranes with a molecular weight cut-off (MWCO) of 6,000–8,000 Da (Spectrum Laboratories, Los Angeles, Calif.). The dialysates were concentrated by continuous flow ultrafiltration using a membrane with a 1,000 Da MWCO (Pellicon, Millipore Corp., Milford Mass.). The final concentrate contained $\geq 10^8$ ce of transfer factor/ml.

G. Affinity Purification of HSV-1 Specific Transfer Factor

The HSV-1 coat protein, glycoprotein D (HSV-1 gD) was used as the antigen during affinity purification of HSV-1 specific transfer factor. Recombinant HSV-1 gD (rHSV-1 gD) with a poly-histidine (6×) carboxyterminal tail was expressed in baculovirus.[54] Baculovirus conditioned medium containing rHSV-1 gD was loaded onto a histidine affinity resin column (Nickle-NTA resin, Qiagen, Inc., Chatsworth, Calif. 91311 USA) previously deionized with water.

More specifically, rHSV-1 gD was bound to Ni-NTA beads according to the following procedure: The Ni-NTA beads were washed with 5–10×volumes of Phosphate Buffered Saline (PBS, pH 7.3)(the PBS formula is: 0.23 g $NaH_2PO_4$ (anhydrous) (1.9 mM), 1.15 g $NaH_2PO_4$ (anhydrous) (8.1 mM), 9.00 g NaCl (154 mM), add $H_2O$ to 900 ml, adjust to desired pH (7.2 to 7.4) using 1M NaOH or 1M HCl and add H$_2$O to 1 liter); centrifuged at 2000×g for 7 minutes at 4° C. This wash procedure was repeated two additional times. The rHSV-1 gD (1.5 mg/ml in PBS) was added to the washed beads (1:1; vol:vol; gD:Ni-NTA beads). The beads were rotated with rHSV-1 gD for 2 hours at 4° C. The preparation was centrifuged at 2000×g for 7 minutes (40° C.) and the supernatant was discarded. The beads were washed with 5–10×volumes of PBS; centrifuged at 2000×g for 7 minutes at 4° C. This wash procedure was repeated two additional times.

After the final wash procedure, the supernatant was discarded and bovine serum albumin (BSA; 100 mg/ml in water) was added to the Ni-NTA beads containing bound HSV-1 gD (1:1; vol:vol; BSA:gD Ni-NTA beads) in order to block remaining non-specific protein binding sites. Alternatively, as little as 5 mg/ml can be used. The beads were rotated for 2 h at room temperature and then centrifuged at 2000×g for 7 minutes. The beads were washed three times with 10×volume of PBS. Ni-NTA beads that did not contain gD were processed in an identical manner to provide a control for the affinity purification. After the final wash, dialysate containing HSV-1 specific transfer factor was added to the gD Ni-NTA and control beads. The beads were rotated for 16 to 20 hours at 4° C. 1 ml of gD Ni-NTA beads was capable of binding 7 to 10×10$^8$ ce of HSV-1 specific transfer factor.

The suspension of dialysate and gD Ni-NTA beads was centrifuged at 2000×g for 7 minutes at 4° C. The supernatant (post absorption fraction) was removed (saved for DTH assay), and the gD NI-NTA beads were washed three times with PBS as described above. Bound HSV-1 specific transfer factor was eluted initially by adding 100% acetonitrile (CH$_3$CN) (6:1; vol:vol; CH$_3$CN:gD Ni-NTA beads) and rotating the beads for 40 minutes at 4° C. The eluate was removed by centrifuging the beads at 2000×g for 7 minutes. This elution procedure was repeated using 50:50 CH$_3$CN:water. Both eluants were combined, the CH$_3$CN was removed by evaporation using nitrogen, and the remaining aqueous sample was dialyzed extensively against deionized water, frozen & lyophilized. A portion of the HSV-1 specific transfer factor affinity purified material was redissolved in PBS and assayed for bioactivity using the DTH assay, as described in Example 31.

The results of this procedure are shown in FIG. 20. The transfer factor activity in the starting material (the ultrafiltrate) is completely removed by absorption on the gD immune absorbant (post absorption gD), but not by the NTA-Nickel-Agarose beads that do not have gD (post absorption Ni). The transfer factor activity is recovered from the gD-beads by elution (Eluate).

EXAMPLE 31

Delayed Type Hypersensitivity Assay of *Herpes simplex* VirusType-1 Antigen and *Herpes simplex* Virus Type-1 Glycoprotein D Specific Transfer Factor Herpes simplex antigen or recombinant glycoprotein D (1500 μg/ml) dissolved in PBS is used as the test antigen. 25 μl of either HSV-1 antigen containing 50×10$^5$ plaque forming units (pfu) or gD solution (37.5 μg) is injected into one footpad and 25 μl of HBSS is injected into the contralateral footpad. The changes in footpad thickness are measured after 18 hours, as described above. An example of the transfer factor activity in these preparations is shown in FIG. 21. Mice that were treated with HBSS did not develop swelling in footpads that were injected with HBSS or glycoprotein D. In contrast, ultrafiltrates from HSV-1 immune cattle sensitized recipients to express delayed-type hypersensitivity to glycoprotein D (middle bars) and this activity was not lost after lyophilization of the sample (right hand bars).

For purposes of quantitating recovery between purification steps, one unit of transfer factor activity can be defined as the material producing half-maximal footpad swelling response from a dose-response curve of log$_{10}$ of the mononuclear splenocyte equivalents versus the increment of footpad swelling. With the exception of crude dialysates, the various purified preparations contained such small amounts of protein that substantial proportions of the samples would be required for conventional protein assays. For purposes of this application, the specific activity of the preparations is described in terms of the number of units of transfer activity per absorbance unit at 214 nm. The various volatile solvents were removed from samples through lyophilization. The samples were dissolved in purified water for absorbance measurements. Absorbance measurements were made using self-masking quartz glass microcuvettes (type 18M-S; NSG Precision Cells Inc., Farmingdale, N.Y.) and a Gilford model 260 UV spectrophotometer (Gilford Instrument Laboratories, Inc., Oberlin, Ohio).

EXAMPLE 32

Transfer of Antigen Specific Cellular Immune Response for *Herpes simplex* Virus-1 Between Species with Herpes-Specific Transfer Factor The transfer factor with antigen specificity for *Herpes simplex* virus-1 (HSV-1), was isolated from one mammalian species, as described in Example 30, and used to treat another mammalian species as follows:

Animal models for Herpes simplex infections

1. Systemic infections. Various doses of infectious *Herpes simplex* virus in a volume of 0.5 ml were injected intraperitoneally into BALB/c mice, aged 6–10 weeks. The mice were examined daily and morbidity and mortality were recorded. The results of dose-survival studies are summarized in FIG. 22.

2. Cutaneous infections. The general model is adapted from Simmons and Nash, *J. Virol.* 52:816–821, 1984. BALB/c female mice, aged 6–7 weeks, were depilated by first shaving, and then application of an emulsion containing calcium hydroxide (Nair, Carter-Wallace, Inc., New York, N.Y). The following day the dosage of infectious *Herpes simplex* virus (10$^4$–10$^5$ pfu) in a volume of 10 μl is applied to the skin. The area is scarified with 18 strokes with a 26 gauge hypodermic needle.

The course of the infections was monitored daily. The scorer was unaware of the treatment given to the various groups of mice. Numerical scores were assigned to the general health of the mice, the progress or regression of the cutaneous infections and the development and clinical course of neurological lesions. The scoring key is shown in Table IV.

TABLE IV

Scoring Key For Cutaneous Herpes Simplex Infections In Mice

General Health:

0 Normal weight, good coat, active
1 Scruffy coat
2 Weight loss
3 Death

Skin Lesions:

0 No lesion
1 Edema at site of infection
2 Pock at site of infection
3 Pock with satellite lesions
1 Healing lesions

TABLE IV-continued

Scoring Key For Cutaneous Herpes Simplex Infections In Mice

Neurological Functions:

0 No Neurological Dysfunction
1 Weakness in one hind leg
2 Weakness in both hind legs
2 Paralysis in one hind leg
3 Paralysis in both hind legs Seriously ill or moribund animals were euthanized and given a score of 3.

Assessment of Efficacy of Transfer Factor Treatment

The goal of these studies was to measure the protective activity of transfer factors against challenges with virulent Herpes simplex virus. The transfer factor-containing solution was given intraperitoneally in a volume of 0.5 ml. Seven (7) days later the mice were challenged with Herpes simplex virus either by intraperitoneal infection or cutaneous scarification as described above. Mice with cutaneous infections were monitored for 14 days, and mice with systemic infections were monitored for 35 days.

Natural history of Herpes simplex Infections in BALB/c Mice

1. Systemic infections. As shown in FIG. 22, systemic infections with $10^4$ or more plaque-forming units of virus caused infections that were fatal for 80 percent of the mice.

2. Cutaneous infections. By day two there was edema at the site of infection. In untreated mice, a pock formed within 3–4 days. The infection progressed with development of satellite lesions along the course of the superficial nerves. Approximately 20 percent of the untreated mice developed paresis or paralysis of the lower extremities, and all of these mice died or were euthanized. The overall mortality of these infections in untreated mice is 30–40 percent. However, mice that survive to day 14 recover (FIG. 23).

Effects of Transfer Factor Treatment on the Clinical Course of Herpes simplex Infections 1. Systemic infections. Pretreatment of mice with $10^9$ spleen cell equivalents of bovine herpes simplex-specific transfer factor, which had a specific activity of greater than 5,000 units, significantly prevented mortality of the Herpes simplex infections. As shown in FIG. 24, the control mice that were not treated experienced 80 percent mortality by day 11. In contrast, 83 percent of the transfer factor treated mice were alive on day 11, although the overall mortality reached 33 percent by day 13.

2. Cutaneous infections. The natural history of cutaneous infections with Herpes simplex is summarized in FIG. 25. All mice, treated or untreated, developed edema at the sites of infection and scarification. Pock formation was uncommon in treated mice, and when pocks developed, they resolved quickly. A few treated mice developed satellite lesions, but they resolved during the second week after infection. One mouse in the transfer factor-treated groups (a population of 50 mice) developed neurological disease and was euthanized.

Therefore, Herpes simplex-specific transfer factors from bovine sources protected mice from challenges with doses of virulent Herpes simplex virus that are lethal for 80 percent of untreated mice. Thus, the protective activities of transfer factors are not restricted by species barriers.

Pretreatment of mice with Herpes simplex-specific transfer factor significantly reduced morbidity and mortality of experimental Herpes simplex infections. Pretreatment of mice with identical dialysates or ultrafiltrates from leukocytes of cattle that were not immune to Herpes simplex did not provide protection against experimental Herpes simplex infections.

EXAMPLE 33

Reverse Phase Chromatography of Herpes simplex Type-1 Glycoprotein D Specific Transfer Factor Affinity Purified HSV-1 specific transfer factor (25 to $30 \times 10^8$ ce isolated from 800–1000 ml of bovine blood lymphocytes) produced as described in Example 30 was redissolved in 1.0 ml of deionized water. The sample was centrifuged at 10,000×g for 4 minutes and passed through a 0.2 μm filter. Aliquots (200 μl) of the filtered sample were injected onto a reverse phase C18 column (RP-C18, Vydac 4.6×250 mm) previously equilibrated with 5 mM tetrabutyl ammonium phosphate (TBAP, hplc grade Pierce, Rockford, Ill.; buffer A). The bound protein was eluted with a linear gradient (1% change in % buffer B/min) of 5 mM TBAP, 100% acetonitrile ($CH_3CN$ hplc grade Fisher, Pittsburgh, Pa.; buffer B) at a flow rate of 1 ml/min. Elution of protein was monitored at 214 nm. A single major peak eluted at 5 to 10% $CH_3CN$ can be seen in FIG. 26. The peaks from 5 separate runs were pooled, dialyzed against deionized water and lyophilized. An aliquot ($7 \times 10^8$ ce) was used to assay for bioactivity.

FIG. 27 shows the DTH response of the TBAP purified HSV-1 specific transfer activity. Bovine HSV-1 specific transfer factor dialysate was lyophilized and dissolved in 2.0 ml water. HSV-1 dialysate, the acetonitrile eluate of gD Ni-NTA beads (gD eluate) and RP-C18 peak were diluted in HBSS to a concentration of $5 \times 10^7$ ce/ml. $5 \times 10^7$ ce (1.0 ml) of each fraction was administered intraperitoneally (ip) to each mouse in all experimental groups (n=6). Twenty-four hours later, footpads were injected with 25 μg of recombinant HSV-1 glycoprotein D (rHSV-1 gD) in 25 μl HBSS; contralateral footpads were injected with 25 μl HBSS. DTH response (footpad swelling) induced by HSV-1 specific transfer factor dialysate, gD eluate, and C18 Pk was determined twenty-four hours after injection of the antigen.

EXAMPLE 34

Amino-terminal Sequence Analysis of Ferritin Specific Transfer Factor

As described in more detail below, cyanogen bromide was used to cleave the substantially purified transfer factor polypeptide at the carboxyl side of methionine residues prior to sequencing. A modified Edman degradation protocol was used to obtain amino acid sequence information.

The sequence data for one sample of murine ferritin-specific transfer factor, three samples of murine ovalbumin-specific transfer factor and one sample of bovine HSV-1 gD-specific transfer factor are presented in Examples 34–39. The primary calls were made after determining the molar concentrations of each amino acid at each cycle of degradation. Secondary calls were made based on other amino acids that appeared in the same cycle, at a lesser concentration. As described in more detail in Example 39, from these data the conserved sequence AQDLED (SEQ ID NO:1) or LLYAQDLEDN (SEQ ID NO:2), or alternatively LLYAQDVEDN (SEQ ID NO:3), is believed to represent at least a portion of the conserved region of a transfer factor molecule.

The lyophilized gel filtration purified ferritin specific transfer factor (10 to $12 \times 10^8$ ce) prepared as in Example 5 was redissolved in 1.0 ml deionized water. The ferritin specific transfer factor was concentrated onto a polyvinyl difluoride (PVDF) membrane using a Prosorb sample preparation cartridge (Prosorb, Perkin Elmer-ABI, Foster City, Calif.). The membrane was subjected to N-terminal sequence analysis (ABI 492 gas phase sequencer, Perkin Elmer-ABI, Foster City, Calif.). No sequence was observed during 5 cycles of the Edman chemistry. The PVDF membrane in the sequencer blot cartridge containing bound ferritin specific transfer factor was removed from the sequencer, and a glass fiber filter (ABI #401111, Perkin Elmer-ABI, Foster City, Calif.) was placed over the PVDF membrane and wetted with 35 μl of 30 mg/ml cyanogen bromide (CNBr) in 70% formic acid. The glass filter and membrane were wrapped in aluminum foil and left at room temperature for 12–16 hours. The PVDF membrane was unwrapped, allowed to dry in a hood, and re-loaded into the sequencer. The yield of amino acids identified at each Edman cycle is summarized in Table V.

secondary sequence(s) may suggest the presence of lower amounts of a different CNBr fragment. The amino acid at position 10 was either aspartate (D), or at a significantly lower probability, glutamate (E) as a secondary call. By the designation "X" is meant that an unidentified amino acid was detected at that position, and therefore, "X" may represent any of the naturally occurring amino acids. Lower case letters represent less certainty in calls. Methionine (M) residues at the amino terminus of the sequence shown can be inferred due to cyanogen bromide cleavage.

TABLE V

N-Terminal Sequence of CNBr Fragment (Ferritin TF-1)

| | D | N | S | Q | T | G | E | A | H | Y | R |
|---|---|---|---|---|---|---|---|---|---|---|---|
| 1 | | | | | | | | | | | |
| 2 | 7.33 | 5.72 | 0 | 0 | 2.7 | 12.4 | 5.35 | 4.12 | 0 | 3.6 | 0.23 |
| 3 | 7.36 | 5.7 | 0 | 12.9 | 1.52 | 10.3 | 7.67 | 3.39 | | 2.12 | |
| 4 | 7.58 | 4.87 | 0 | 0 | 1.38 | 11.6 | 4.96 | 2.45 | 0 | 5.45 | 0.18 |
| 5 | 5.3 | 3.9 | 0 | 9.71 | 1.26 | 10.5 | 6.07 | 4.62 | 0 | 2.93 | 0 |
| 6 | 4.16 | 3.28 | 0 | 13.4 | 0.86 | 8.4 | 5.01 | 2.79 | | 2.3 | 0.16 |
| 7 | 7.26 | 4.52 | 0 | 11.1 | 1.26 | 8.56 | 4.16 | 4.52 | | 3.34 | |
| 8 | 4.17 | 2.97 | 0 | | 1.25 | 8.18 | 3.6 | 5.21 | | 2.77 | |
| 9 | 4.45 | 2.08 | 0 | 10.6 | 1.56 | 8.89 | 5.2 | 3.62 | | 2.88 | |
| 10 | 5.64 | 1.56 | 0 | 10.8 | 1.17 | | 3.91 | 3.31 | | 2.92 | |
| 11 | 4.24 | 3.4 | 0 | 11.9 | 0.53 | 7.6 | 3.68 | 3.47 | | 2.62 | |
| 12 | 4.01 | 2.76 | 0 | 11.4 | 1.51 | 7.6 | 3.06 | 2.41 | | 1.95 | 0.11 |
| 13 | 3.09 | 3.04 | 0 | 12.3 | 0.95 | 6.93 | 3.02 | 3.2 | | 2.37 | 0.16 |
| 14 | 3.96 | 2.35 | 0 | 12.4 | 1.28 | 7.7 | 4.2 | 2.36 | | 1.63 | |
| 15 | 3.33 | 1.81 | 0 | 8.55 | 0.94 | 6.78 | 3.52 | 2.53 | | 1.4 | |
| 16 | 2.49 | 2 | 0 | 10.9 | 1.09 | 6.2 | 3.16 | 2.75 | | 1.21 | |
| 17 | 2.79 | 2.21 | 0 | 0.95 | 1.18 | 6.76 | 2.94 | 3.43 | | 1.1 | |
| 18 | 2.03 | 2.04 | 0 | 11.35 | | | 3.52 | 2.96 | | 1.48 | |
| 19 | | | 0 | | | | | | | | |
| 20 | .22 | 2.04 | 0 | 9.86 | 1.2 | 6.49 | 3.06 | 2.22 | | 1.87 | |

| | P | M | V | W | F | I | K | L | 1° CALL | 2° CALL |
|---|---|---|---|---|---|---|---|---|---|---|
| 1 | | | | | | | | | | |
| 2 | 1.95 | 0.24 | 3.65 | 0 | 3.2 | 2.89 | 2.68 | 7.74 | L | |
| 3 | 2.33 | | 3.35 | 0 | 3.1 | 2.69 | 1.75 | 11.9 | L | E |
| 4 | 2.83 | 0.87 | 3.77 | 0 | 2.51 | 3.31 | 1.41 | 9.77 | Y | PGV |
| 5 | 2.22 | 0.97 | 3.32 | 0.54 | 3.12 | 3.31 | | 9.32 | AE | F |
| 6 | 3.02 | | 3.73 | | 2.26 | 2.88 | | 10 | Q | PVL |
| 7 | 2.33 | 0.47 | 2.3 | | 2.19 | 3.52 | 0.73 | 10.9 | D | NTG |
| 8 | 2.2 | 0.47 | 3.13 | | 2.03 | 4.18 | | 12.42 | LV | AI |
| 9 | 1.8 | 0.74 | 2.6 | | 2.24 | 0.19 | 0.49 | 0.91 | E | GDF |
| 10 | 2.01 | 0.91 | 2.84 | 0.24 | 1.89 | 4.31 | | 6.21 | D | Y |
| 11 | 1.86 | 0 | 2.89 | 0 | 1.9 | 4.2 | | 7.25 | N | L |
| 12 | 1.43 | | 2.86 | | 1.98 | 6.34 | | 7.94 | I | TL |
| 13 | 1.52 | | 2.84 | | 1.71 | 4.24 | 0.85 | 6.03 | N | YAP |
| 14 | 1.38 | 0.49 | 2.6 | | 1.59 | 3.15 | 0.96 | 4.8 | ED | GT |
| 15 | 1.41 | 0.41 | 2.63 | | 1.7 | 4.33 | | 4.72 | I | FP |
| 16 | 1.14 | 0.77 | 1.48 | | 1.74 | 3.98 | 0.9 | 4.8 | (AK) | T |
| 17 | 1.07 | 0.47 | 2.26 | | 1.38 | 2.09 | 0.51 | 6.34 | L | AVD NT |
| 18 | 1.38 | 0.59 | 1.82 | | 2.17 | 2.59 | | 5.47 | (FI) | EY |
| 19 | | | | | | | | | | |
| 20 | 1.3 | 0.47 | 1.78 | 0 | 1.78 | 2.36 | | 4.44 | | |

A fragment with a free $NH_2$ was detectable and sequenceable on the CNBr treated membrane. This fragment had the sequence:

XLLYAQDVEDNINDIalf (SEQ ID NO:4), or
XLLYAQDVEENINDIalf (SEQ ID NO:5)

Significantly lower levels of alternative amino acids representing secondary sequence(s), shown in the lower sequence, were also detected on the membrane. These

EXAMPLE 35

Amino-terminal Sequence Analysis of Ovalbumin Specific Transfer Factor

The lyophilized gel filtration purified material (10 to $12 \times 10^8$ ce) prepared as in Example 5 was redissolved in 1.0 ml deionized water. The ovalbumin specific transfer factor material was concentrated onto a polyvinyl difluoride (PVDF) membrane using a Prosorb sample preparation cartridge (Prosorb, Perkin Elmer-ABI, Foster City, Calif.). The membrane was subjected to N-terminal sequence analysis (ABI 492 gas phase sequencer, Perkin Elmer-ABI, Foster City, Calif.). No sequence was observed during 5 cycles of the Edman chemistry. The PVDF membrane in the sequencer blot cartridge containing bound ovalbumin specific transfer factor was removed from the sequencer, and a glass fiber filter (ABI #401 11 1, Perkin Elmer-ABI, Foster City, Calif.) was placed over the PVDF membrane and wetted with 35 μl of 30 mg/ml cyanogen bromide (CNBr) in 70% formic acid. The glass filter and membrane were wrapped in aluminum foil and left at room temperature for 12–16 hours. The PVDF membrane was unwrapped, allowed to dry in a hood, and re-loaded into the sequencer. The yield of amino acids identified at each Edman cycle is summarized in Table VI.

shown in the lower sequence were also detected on the membrane. These secondary sequence(s) may suggest the presence of lower amounts of a different CNBr fragment. The invention contemplates that each secondary call could be individually or jointly present in a sequence, however, the primary call (upper) sequence is most preferred. By the designation "X" is meant that an unidentified amino acid was detected at that position, and therefore, "X" may represent any of the naturally occurring amino acids. Lower case letters represent less certainty in calls. Methionine (M) residues at the amino terminus of the sequence shown can be inferred due to cyanogen bromide cleavage.

TABLE VI

N-Terminal Sequence of CNBr Fragment
(Ovalbumin Transfer Factor; OVA-1)

|    | D    | N    | S    | Q    | T    | G    | E    | A    | H | Y    | R |
|----|------|------|------|------|------|------|------|------|---|------|---|
| 1  | 7.24 | 4.96 |      |      | 5.52 | 14.8 | 3.2  | 0.26 |   | 4.16 |   |
| 2  | 4.46 | 2.23 | 3.58 | 2.29 | 2.69 | 11.8 | 2.76 | 2.58 |   | 1.56 |   |
| 3  | 4.11 | 1.66 | 2.03 |      | 1.81 | 8.19 | 2.5  | 2.11 |   | 1.72 |   |
| 4  | 3.27 | 1.39 | 1.48 |      | 1.34 | 5.3  | 1.93 | 1.29 |   | 1.59 |   |
| 5  | 2.91 | 1.34 | 2.06 |      | 1.12 | 5.24 | 2.16 | 1.89 |   | 1.06 |   |
| 6  | 2.41 | 0.93 | 1.95 | 2.18 | 1.35 | 3.95 | 1.99 | 1.53 |   | 1.28 |   |
| 7  | 3.59 | 1.1  | 1.56 | 1.84 | 0.93 | 3.92 | 2.01 | 1.63 |   | 0.85 |   |
| 8  | 2.69 | 1.02 | 1.26 | 1.65 | 1.09 | 3.8  | 1.57 | 1.96 |   | 1.07 |   |
| 9  | 2.37 | 0.98 | 1.54 |      | 1.0  | 3.55 | 1.87 | 1.65 |   | 1.26 |   |
| 10 | 2.61 | 0.65 | 1.21 |      | 0.97 | 3.31 | 1.75 | 1.42 |   | 1.2  |   |
| 11 | 2.22 | 0.85 | 1.28 | 1.4  | 0.9  | 2.88 | 1.44 | 1.44 |   | 1.29 |   |
| 12 | 2.17 | 0.8  |      |      | 1.15 | 3.09 | 1.6  | 1.25 |   | 1.05 |   |
| 13 | 1.9  | 0.89 |      |      | 1.06 | 2.72 | 1.46 | 1.45 |   | 1.24 |   |
| 14 | 1.86 | 0.99 |      |      | 0.95 | 2.87 | 1.41 |      |   | 1.0  |   |
| 15 | 1.97 | 0.59 |      |      | 0.75 | 2.46 | 1.51 | 1.04 |   | 0.55 |   |
| 16 | 1.55 | 0.88 |      |      | 0.67 | 2.62 | 1.29 | 1.08 |   | 0.74 |   |
| 17 | 1.39 | 0.84 |      |      | 0.52 | 2.57 | 1.25 | 1.14 |   | 0.82 |   |
| 18 | 1.21 | 0.61 |      |      | 0.89 | 2.5  | 1.31 | 1.12 |   | 0.72 |   |
| 19 | 1.32 | 0.59 |      |      | 0.75 | 2.46 | 1.46 | 1.04 |   | 0.55 |   |
| 20 | 1.36 | 0.66 |      |      | 1.06 | 2.7  | 1.47 | 1.12 |   | 1.0  |   |

|    | P    | M    | V    | W    | F    | I    | K    | L    | 1° CALL | 2° CALL |
|----|------|------|------|------|------|------|------|------|---------|---------|
| 1  |      |      | 3.28 |      | 1.25 | 7.79 |      | 2.77 | X       |         |
| 2  |      |      | 2.14 |      | 1.48 | 5.76 | 1.49 | 2.0  | X       |         |
| 3  | 1.96 |      | 1.91 | 1.08 | 1.6  | 3.2  | 1.49 | 3.68 | L       | (P,F)   |
| 4  | 1.84 |      | 1.82 |      | 0.96 | 2.97 | 1.32 | 3.04 | Y       | X       |
| 5  | 1.56 |      | 1.84 | 0.8  | 1.07 | 2.37 | 101  | 2.57 | A       | E       |
| 6  | 1.68 |      | 1.95 | 0.75 | 1.1  | 1.75 | 0.81 | 2.55 | Q       | (Y,P)   |
| 7  | 1.59 |      | 1.56 | 0.31 | 1.02 | 1.63 | 1.16 | 2.76 | D       | K       |
| 8  | 0.97 | 0.28 | 1.96 |      | 1.24 | 0.93 | 1.04 | 3.29 | (V,A,L) | X       |
| 9  | 1.25 |      | 1.52 | 0.66 | 1.24 | 1.06 | 0.78 | 2.7  | E       | X       |
| 10 | 1.22 |      | 1.51 |      | 0.87 | 1.5  | 0.8  | 2.09 | D       | X       |
| 11 | 0.94 |      | 1.47 | 0.23 | 1.0  | 1.74 | 0.58 | 2.23 | (I,N)   | X       |
| 12 | 0.96 |      | 1.64 |      | 1.21 | 1.56 | 0.5  | 2.48 | E       |         |
| 13 |      |      | 1.43 | 0.66 | 0.98 | 1.35 | 0.42 | 1.91 | A       |         |
| 14 | 0.97 |      | 1.5  |      | 0.86 | 1.05 | 0.81 | 1.69 | (D,K)   |         |
| 15 | 0.54 |      | 1.23 |      | 1.22 | 1.01 | 0.61 | 1.63 |         |         |
| 16 | 0.87 |      | 1.17 | 0.23 | 1.02 | 1.17 |      | 1.46 |         |         |
| 17 | 0.68 |      | 1.26 | 1.4  | 0.42 | 0.64 | 1.07 | 2.08 |         |         |
| 18 | 0.88 |      | 1.06 | 0.32 | 0.98 | 0.91 | 0.42 | 1.75 |         |         |
| 19 | 0.54 |      | 1.23 |      | 1.22 | 1.01 | 0.61 | 1.6  |         |         |
| 20 | 0.63 |      | 1.28 | 0.31 | 0.99 | 0.68 | 0.91 | 1.77 |         |         |

A fragment with a free $NH_2$ was detectable and sequenceable on the CNBr treated membrane. This fragment had the sequence:

XXLYAQDVEDNEAD (SEQ ID NO:6) or
XXLYAQDLEDIEAK (SEQ ID NO:7)

Significantly lower levels of alternative amino acids at positions 8, 11 and 14 representing secondary sequence(s)

EXAMPLE 36

Amino-terminal Sequence Analysis of HSV-1 Specific Transfer Factor

The lyophilized RP-C18 (TBAP) purified material prepared as in Example 33 was redissolved in 0.3 ml deionized water. 40% of the purified HSV-1 specific transfer factor (5 to $10 \times 10^8$ ce) was blotted onto a polyvinyl difluoride (PVDF) membrane (PROBLOT, Perkin Elmer-ABI, Foster city, Calif.). The membrane was subjected to N-terminal sequence analysis (ABI 492 gas phase sequencer, Perkin Elmer-ABI, Foster City, Calif.). No sequence was observed during 5 cycles of the Edman chemistry. The PVDF membrane in the sequencer blot cartridge containing bound HSV-1 specific transfer factor was removed from the sequencer, and a glass fiber filter (ABI #401111, Perkin Elmer-ABI, Foster City, Calif.) was placed over the PVDF membrane and wetted with 35 μl of 30 mg/ml cyanogen bromide (CNBr) in 70% formic acid. The glass filter and membrane were wrapped in aluminum foil and left at room temperature for 12–16 hours. The PVDF membrane was unwrapped, allowed to dry in a hood, and re-loaded into the sequencer. The yield of amino acids identified at each Edman cycle is summarized in Table VII.

sequence were also detected on the membrane. These secondary sequence(s) may suggest the presence of lower amounts of a different CNBr fragment. The amino acid at position 8 was either valine (V) or at a significantly lower probability leucine (L). By the designation "X" is meant that an unidentified amino acid was detected at that position, and therefore, "X" may represent any of the naturally occurring amino acids. Lower case letters represent less certainty in calls. Methionine (M) residues at the amino terminus of the sequence shown can be inferred due to cyanogen bromide cleavage.

TABLE VII

N-Terminal Sequence of CNBr Fragment
(HSV-1 Transfer Factor)

| | D | N | S | Q | T | G | E | A | H | Y | R |
|---|---|---|---|---|---|---|---|---|---|---|---|
| 1 | 14.6 | 6.96 | | | | | | | | 5.19 | |
| 2 | 9.86 | 4.56 | | | | | | 3.26 | | 2.29 | |
| 3 | 8.76 | 4.86 | | | 1.76 | 8.9 | | 2.88 | | 1.64 | |
| 4 | 9.25 | 3.75 | | | 2.3 | 8.08 | 5.01 | 2.38 | | 3.58 | |
| 5 | 6.38 | 3.44 | | 2.63 | 1.19 | 8.04 | 5.43 | 3.74 | | 2.46 | |
| 6 | 4.91 | 2.61 | | 5.42 | 1.54 | 7.1 | 5.18 | 2.54 | | 1.87 | |
| 7 | 9.29 | 3.47 | | 3.16 | 1.38 | 7.01 | 4.52 | 2.8 | | 1.74 | |
| 8 | 5.18 | 2.41 | | 2.4 | 1.97 | 6.56 | 3.66 | 2.91 | | 2.15 | |
| 9 | 6.28 | 1.65 | | 1.93 | 1.7 | 6.62 | 5.29 | 2.57 | | 2.09 | |
| 10 | 7.3 | 1.71 | | 2.68 | 1.4 | 6.39 | 3.94 | 2.67 | | 1.95 | |
| 11 | 5.64 | 2.7 | | 2.66 | 1.29 | 5.88 | 3.33 | 2.97 | | 1.94 | |
| 12 | 4.63 | 2.52 | | | 2.03 | 5.63 | 2.92 | 2.03 | | 1.67 | |
| 13 | 3.99 | 2.73 | | | 1.66 | 5.52 | 2.71 | 2.13 | | 1.88 | |
| 14 | 5.0 | 1.82 | | | 1.31 | 5.44 | 3.46 | 1.61 | | 1.7 | |
| 15 | 4.01 | 1.55 | | | 1.76 | 5.33 | 2.76 | 1.6 | | 1.42 | |
| 16 | 3.45 | 1.79 | | | 1.37 | 5.27 | 2.64 | 1.85 | | 1.19 | |
| 17 | 3.75 | 1.97 | | | 1.28 | 5.11 | 2.55 | 2.18 | | 1.11 | |
| 18 | 3.32 | 1.65 | | | 1.0 | 5.03 | 3.29 | 2.04 | | 1.09 | |
| 19 | 3.16 | 1.31 | | | 1.04 | 5.13 | 2.93 | 1.72 | | 1.64 | |
| 20 | 3.16 | 1.56 | | | 1.22 | 4.92 | 2.99 | 1.7 | | 1.24 | |

| | P | M | V | W | F | I | K | L | 1° CALL | 2° CALL |
|---|---|---|---|---|---|---|---|---|---|---|
| 1 | 2.52 | 0.59 | 4.3 | 2.36 | 2.2 | 4.34 | 5.89 | 3.95 | X | |
| 2 | 2.21 | 0.57 | 3.27 | 1.84 | 1.63 | 2.97 | 2.92 | 6.83 | L | A |
| 3 | 2.44 | 0.33 | 3.54 | 2.17 | 1.38 | 2.66 | 3.16 | 8.33 | L | GKF |
| 4 | 2.6 | 0.48 | 2.99 | 1.4 | 1.49 | 2.88 | 2.6 | 6.87 | Y | D |
| 5 | 1.97 | 0.4 | 2.12 | 2.16 | 2.15 | 2.49 | 1.51 | 6.04 | A | E |
| 6 | 2.22 | 0.28 | 2.99 | 2.1 | 1.57 | 2.68 | 1.47 | 6.66 | Q | V(IP) |
| 7 | 1.65 | 0.53 | 2.3 | 1.02 | 1.2 | 2.21 | 1.59 | 6.34 | D | |
| 8 | 1.52 | 0.52 | 3.09 | 2.39 | 1.23 | 2.73 | 2.13 | 7.58 | V | L |
| 9 | 1.67 | 0.4 | 2.24 | 2.78 | 1.23 | 2.25 | 1.89 | 5.39 | E | W |
| 10 | 1.45 | 0.26 | 2.26 | 1.55 | 1.34 | 1.39 | 1.3 | 3.84 | D | |
| 11 | 1.4 | 0.46 | 2.39 | 2.2 | 1.08 | 2.73 | 1.4 | 4.35 | N | LI |
| 12 | 1.43 | 0.69 | 2.12 | 1.96 | 1.07 | 3.32 | 0.85 | 4.96 | LT | I |
| 13 | 1.21 | 0.68 | 2.22 | 2.25 | 1.2 | 2.42 | 1.82 | 3.93 | K | NY |
| 14 | 1.37 | 0.41 | 2.20 | 2.5 | 1.13 | 1.74 | 1.6 | 2.97 | D | EPW |
| 15 | 1.29 | 0.28 | 2.57 | 2.11 | 0.9 | 2.09 | 0.96 | 3.25 | VT | IL |
| 16 | 1.27 | 0.29 | 1.91 | 1.78 | 0.89 | 2.14 | 1.74 | 3.41 | K | AN |
| 17 | 1.55 | | 1.84 | 2.11 | 0.88 | 1.66 | 1.68 | 4.22 | L | PWD |
| 18 | 1.03 | 0.64 | 1.95 | 2.54 | 0.94 | 1.22 | 1.38 | 3.5 | E | V |
| 19 | 0.91 | 0.58 | 1.49 | 2.29 | 1.28 | 0.82 | 0.62 | 3.32 | Y | F |
| 20 | 1.13 | | 1.38 | 2.96 | 0.95 | | 0.85 | 2.75 | | |

A major fragment with a free $NH_2$ was detectable and sequenceable on the CNBr treated membrane. This fragment had the sequence:

XLLYAQDVEDNTKDVKley (SEQ ID NO:8) or
XLLYAQDLEDNTKDVKley (SEQ ID NO:9)

Significantly lower levels of alternative amino acids representing secondary sequence(s) shown in the lower

EXAMPLE 37

Reverse Phase Chromatography of Ovalbumin Specific Transfer Factor Using Tetrabutyl Ammonium Phosphate Solvent System and Sequencing Thereof Affinity purified ovalbumin specific transfer factor (13× $10^8$ ce) isolated from murine spleen lymphocytes prepared as in Example 3 was redissolved in 0.5 ml of deionized water. The sample was centrifuged at 10,000×g for 4 minutes and passed through a 0.2 μm filter. Aliquots (200 μl) of the filtered sample were injected onto a reverse phase C18 column (RP-C18, Vydac 4.6×250 mm) previously equilibrated with 5 mM tetrabutyl ammonium phosphate (TBAP, hplc grade Pierce, Rockford, Ill.; buffer A). The bound protein was eluted with a linear gradient (1% change in % buffer B/min) of 5 mM TBAP, 100% acetonitrile ($CH_3CN$ hplc grade Fisher, Pittsburgh, Pa.; buffer B) at a flow rate of 1 ml/min. Elution of protein was monitored at 214 nm. A single major peak eluted at 5 to 10% $CH_3CN$ as shown in FIG. 28. The peaks from 3 separate runs were pooled, dialyzed against deionized water and lyophilized.

cartridge containing bound ovalbumin specific transfer factor was removed from the sequencer, and a glass fiber filter (ABI #401111, Perkin Elmer-ABI, Foster City, Calif.) was placed over the PVDF membrane and wetted with 35 μl of 30 mg/ml cyanogen bromide (CNBr) in 70% formic acid. The glass filter and membrane were wrapped in aluminum foil and left at room temperature for 12–16 hours. The PVDF membrane was unwrapped, allowed to dry in a hood, and re-loaded into the sequencer. The yield of amino acids identified at each Edman cycle is summarized in Table VIII.

TABLE VIII

N-Terminal Sequence of CNBr Fragment (Ovalbumin Transfer Factor; OVA-2)

| | D | N | S | Q | T | G | E | A | H | Y | R |
|---|---|---|---|---|---|---|---|---|---|---|---|
| 1 | 7.50 | 3.32 | | 3.67 | | | 7.3 | 5.09 | | 0.14 | |
| 2 | 5.24 | 2.71 | | | | 10.3 | 8.32 | 3.42 | | 0.27 | |
| 3 | 4.56 | 2.82 | | | | 8.16 | 8.05 | 2.54 | | 2.19 | |
| 4 | | | | | | | | | | | |
| 5 | 11.5 | 2.71 | 5.09 | 2.09 | | 8.22 | 11.1 | | | 4.47 | 0.79 |
| 6 | 2.59 | 1.87 | | 4.02 | 2.1 | 6.4 | 6.51 | 2.52 | | 1.75 | |
| 7 | 4.51 | 2.04 | | 3.35 | 1.85 | 6.05 | 6.33 | 2.63 | | 1.85 | |
| 8 | 3.03 | 1.56 | | | 2.11 | 5.7 | 5.54 | 2.36 | | 1.82 | |
| 9 | 3.0 | 1.13 | | | 1.97 | 5.44 | 6.9 | 2.17 | | 1.59 | |
| 10 | 3.71 | 1.24 | | | 1.85 | 5.29 | 5.86 | 2.16 | | 1.66 | |
| 11 | 2.85 | 1.72 | | | 1.68 | 4.86 | 4.86 | 2.5 | | 1.69 | 0.27 |
| 12 | 2.75 | 1.57 | | | 2.22 | 4.54 | 4.56 | 2.02 | | 1.48 | 0.38 |
| 13 | 2.19 | 1.6 | | | 2.33 | 4.37 | 4.43 | 1.81 | | 1.6 | 0.49 |
| 14 | 2.68 | 1.29 | | | 1.57 | 4.22 | 4.94 | 1.66 | | 1.55 | 0.46 |
| 15 | 1.95 | 1.16 | | | 1.45 | 3.78 | 4.28 | 1.73 | | 1.15 | |
| 16 | 1.82 | 1.12 | | | 1.62 | 3.84 | 3.96 | 1.49 | | 1.15 | 0.5 |
| 17 | 1.97 | 1.33 | | | 1.61 | 3.68 | 3.94 | 1.74 | | 1.22 | |
| 18 | 1.47 | 1.15 | | | 1.77 | 3.82 | 4.47 | 1.53 | | 1.17 | |
| 19 | 1.88 | 1.03 | | | 1.75 | 3.71 | 4.01 | 1.41 | | 1.41 | |
| 20 | 1.9 | 1.24 | | | 1.57 | 7.05 | 4.48 | 1.54 | | 1.28 | |

| | P | M | V | W | F | I | K | L | 1° CALL | 2° CALL |
|---|---|---|---|---|---|---|---|---|---|---|
| 1 | | | 3.41 | | 1.73 | 1.68 | 2.87 | 3.27 | X | |
| 2 | 5.24 | | 3.61 | 3.61 | 2.16 | 2.06 | 1.59 | 5.55 | L | EF |
| 3 | 8.66 | | 3.31 | 2.78 | 1.66 | 2.12 | 1.48 | 6.42 | L | YP |
| 4 | | | | | | | | | | |
| 5 | 3.3 | 0.38 | 2.38 | | 1.99 | 2.62 | 1.0 | 5.15 | EYRD | |
| 6 | 2.97 | 0.56 | 2.81 | 2.49 | 1.45 | 1.92 | 0.86 | 4.81 | Q | TV |
| 7 | 2.81 | 1.29 | 2.28 | 4.24 | 1.29 | 2.58 | 1.83 | 4.74 | D | KIW |
| 8 | 3.42 | 0.28 | 2.89 | 1.11 | 1.19 | 2.82 | 0.85 | 6.01 | L | PI |
| 9 | 2.44 | 0.26 | 2.14 | 2.72 | 1.17 | 1.47 | 0.72 | 3.82 | E | |
| 10 | 2.24 | 0.34 | 2.11 | 2.74 | 1.19 | 2.03 | 0.69 | 3.46 | D | I |
| 11 | 2.28 | 0.3 | 2.34 | 2.67 | 0.89 | 1.77 | 0.71 | 3.23 | N | AV |
| 12 | 2.0 | 0.72 | 2.15 | 2.07 | 1.05 | 2.02 | 0.36 | 3.58 | T | |
| 13 | 2.16 | 0.41 | 2.23 | 2.33 | 0.94 | 1.17 | 0.67 | 3.32 | T | K |
| 14 | 1.98 | 0.45 | 2.26 | | 0.76 | 1.39 | 0.66 | 2.77 | D | K |
| 15 | 1.75 | 0.45 | 2.05 | 2.22 | 0.95 | 1.41 | 0.83 | 2.88 | K | A |
| 16 | 1.65 | 0.6 | 1.82 | 1.11 | 0.61 | 1.08 | 0.44 | 2.96 | R | |
| 17 | 1.71 | 0.52 | 1.81 | 2.18 | 0.72 | 0.66 | 0.83 | 3.01 | A | |
| 18 | 1.87 | 0.21 | 1.84 | | 0.83 | 1.22 | 0.69 | 3.15 | E | W |
| 19 | 1.83 | 0.32 | 1.6 | 2.37 | 1.07 | 0.26 | 1.22 | 2.9 | KYD | F |
| 20 | 1.97 | 0.49 | 1.66 | 2.27 | 0.91 | 1.19 | 0.80 | 2.56 | E | P |

Amino-terminal Sequence Analysis of Ovalbumin Specific Transfer Factor

The lyophilized RP-C18 TBAP purified material was redissolved in 1.0 ml deionized water. The purified material was concentrated onto a PVDF membrane using a Prosorb sample preparation cartridge (Prosorb, Perkin Elmer-ABI, Foster City, Calif.). The membrane was subjected to N-terminal sequence analysis (ABI 492 gas phase sequencer, Perkin Elmer-ABI, Foster City, Calif.). No sequence was observed during 5 cycles of the Edman chemistry. The PVDF membrane in the sequencer blot cartridge containing bound ovalbumin specific transfer factor was removed from the sequencer, and a glass fiber filter. A fragment with a free $NH_2$ was detectable and sequenceable on the CNBr treated membrane. This fragment had the sequence:

XLLXXQDLEDNTTDKrae (SEQ ID NO:10)

By the designation "X" is meant that an unidentified amino acid was detected at that position, and therefore, "X" may represent any of the naturally occurring amino acids. Lower case letters represent less certainty in calls. A methionine (M) residue at the amino terminus of the sequence shown can be inferred due to cyanogen bromide cleavage.

EXAMPLE 38

Figure 29:
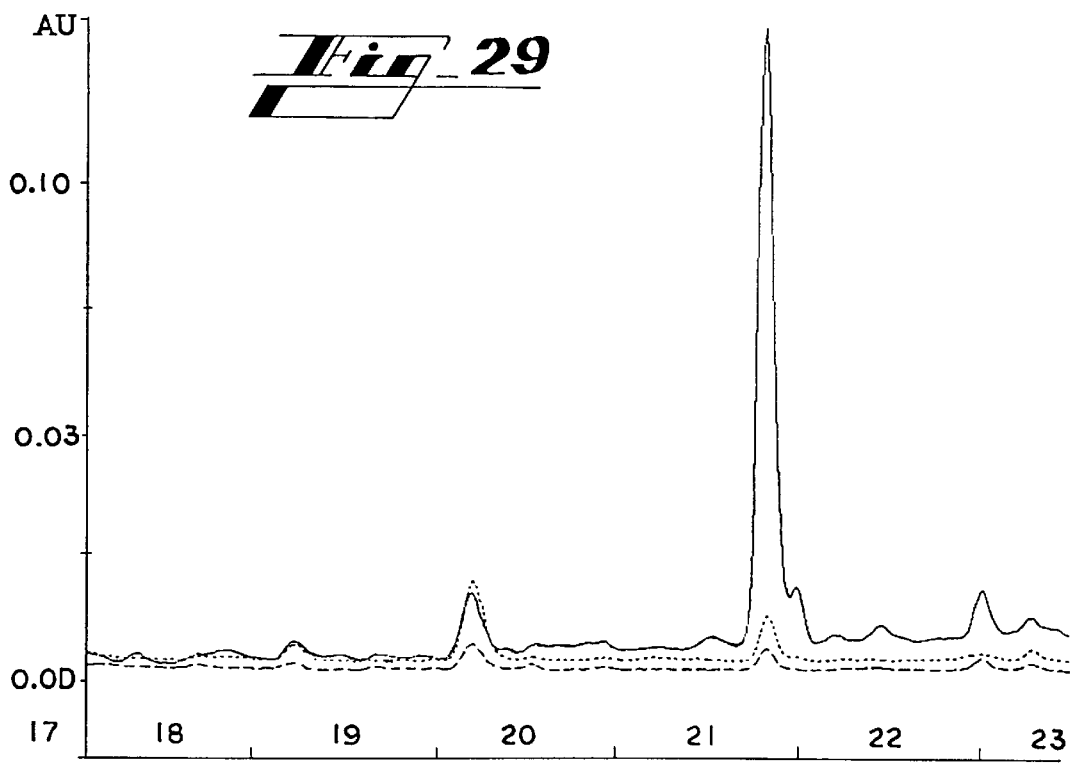
FIG. 29 shows a reverse chromatography of ovalbumin specific transfer factor using trifluoracetic acid (TFA) solvent system. Affinity purified ovalbumin specific transfer factor (5 to $6 \times 10^8$ ce) isolated from murine spleen lymphocytes was redissolved in 0.2 ml of deionized water. The sample was centrifuged at 10,000×g for four minutes and the supernatant was retained. Aliquots (10 to 100 μl) of the filtered sample were injected onto a reverse phase C18 column (RP-C18, Vydac 2.1×250 mm) previously equilibrated with 0.05% trifluoroacetic acid (TFA, hplc grade Pierce, Rockford, Ill.; buffer A). The bound protein was eluted with a linear gradient (1% change in % buffer B/min)

Reverse Phase Chromatography of Ovalbumin Specific Transfer Factor using Trifluoroacetic Acid Solvent System and Sequencing Thereof Affinity Purified ovalbumin specific transfer factor (5 to $6 \times 10^8$ ce) isolated from murine spleen lymphocytes prepared as in Example 3 was redissolved in 0.2 ml of deionized water. The sample was centrifuged at 10,000×g for 4 minutes, and the supernatant was retained. Aliquots (10 to 100 µl) of the filtered sample were injected onto a reverse phase C18 column (RP-C18, Vydac 2.1×250 mm) previously equilibrated with 0.05% trifluoroacetic acid (TFA, hplc grade Pierce, Rockford, Ill.; buffer A). The bound protein was eluted with a linear gradient (1% change in % buffer B/min) of 0.045% TFA, 100% acetonitrile ($CH_3CN$ hplc grade Fisher, Pittsburgh, Pa.; buffer B) at a flow rate of 100 µl/min. Elution of protein was monitored at 214, 260 and 280 nm. (FIG. 29). Sequential injections of increasing quantities of specific transfer factor (blank, 0.26, 0.72 and $3 \times 10^8$ ce) demonstrated that a single major peak eluted at 30% $CH_3CN$ as seen in FIG. 30. The height of this peak increased in direct proportion to quantity injected. Background peaks (present in buffer A blank) did not increase in height. The peak observed from an injection of $3 \times 10^8$ ce of affinity purified ovalbumin specific transfer factor was collected (FIG. 29), and subjected to N-terminal sequence analysis. An aliquot ($7 \times 10^7$ ce) was saved to test bioactivity, shown in FIG. 31.

Amino-terminal Sequence Analysis of Ovabumin Specific Transfer Factor

The RP-C18 TFA purified material ($3 \times 10^8$ ce) was blotted onto a polyvinyl difluoride (PVDF) membrane (Prosorb, Perkin Elmer-ABI, Foster City, Calif.). The membrane was subjected to N-terminal sequence analysis (ABI 492 gas phase sequencer, Perkin Elmer-ABI, Foster City, Calif.). No sequence was observed during 5 cycles of the Edman chemistry. The PVDF membrane in the sequencer blot cartridge containing bound ovalbumin specific transfer factor was removed from the sequencer, and a glass fiber filter (ABI #401111, Perkin Elmer-ABI, Foster City, Calif.) was placed over the PVDF membrane and wetted with 35 µl of 30 mg/ml cyanogen bromide (CNBr) in 70% formic acid. The glass filter and membrane were wrapped in aluminum foil and left at room temperature for 12–16 hours. The PVDF membrane was unwrapped, allowed to dry in a hood, and re-loaded into the sequencer. The yield of amino acids identified at each Edman cycle is summarized in Table IX.

TABLE IX

N-Terminal Sequence of CNBr Fragment (Ovalbumin Transfer Factor -3)

| | D | N | S | Q | T | G | E | A | H | Y | R | P | M | V | W | F | I | K | L | 1° CALL | 2° CALL |
|---|---|---|---|---|---|---|---|---|---|---|---|---|---|---|---|---|---|---|---|---|---|
| 1 | 6.88 | 3.99 | | | 0 | 2.58 | 0 | 1.48 | | 1.75 | 0 | 0 | 0 | | | 0 | 0 | 2.69 | 0.55 | X | G |
| 2 | 3.20 | 1.24 | | | 0.77 | 2.01 | 1.38 | 0.46 | | 0.34 | 0.86 | 0 | 0.74 | 0.14 | | 0.71 | 0.41 | 0.3 | 1.08 | L | |
| 3 | 1.62 | 0.65 | | | 0.55 | 1.91 | 1.21 | 0.71 | | 0.19 | 0.93 | 0 | 0.6 | | | 0 | 0 | 0.48 | 1.52 | L | P |
| 4 | 1.56 | 0.65 | | | 0.44 | 1.94 | 0.97 | 0.71 | | 0.54 | 0.52 | 0 | 0.36 | | | 0.4 | 0 | 0.36 | 1.21 | Y | |
| 5 | 0.87 | 0.61 | | | 0.37 | 1.92 | 1.02 | 1.16 | | 0.51 | 0.4 | 0 | 0.42 | 0.29 | | 0.28 | 0 | 0.48 | 1.2 | A | |
| 6 | 0.69 | 0.5 | | | 0.37 | 1.62 | 0.72 | 0.62 | | 0.41 | 0 | 0 | 0.75 | | | 0.21 | 0.36 | 0 | 1.39 | V | |
| 7 | 1.39 | 0.64 | | | 0.44 | 1.71 | 0.71 | 0.86 | | 0.48 | 0.54 | 0.26 | 0.57 | | | 0 | 0.38 | 0 | 1.35 | D | AP |
| 8 | 0.7 | 0.25 | | | 0.5 | 1.63 | 0.65 | 0.67 | | 0.44 | 0.37 | 0 | 0.49 | | | 0 | 0.37 | 0 | 1.08 | T | |
| 9 | 0.84 | 0.36 | | | 0.31 | 1.37 | 0.63 | 0.77 | | 0.15 | 0.42 | 0.33 | 0.55 | | | 0 | 0.26 | 0 | 1.15 | V | A |
| 10 | 0.89 | 0.43 | | | 0.78 | 1.42 | 0.71 | 0.57 | | 0.31 | 0.27 | 0.18 | 0 | | | 0 | 0 | 0.16 | 0.86 | T(D) | |
| 11 | 0.75 | 0.49 | | | 0.63 | 1.52 | 0.69 | 0.71 | | 0.64 | 0.47 | 0 | 0.29 | | | 0.19 | 0.39 | 0.43 | 0.9 | YK | A |
| 12 | 0.83 | 0.46 | | | 0.62 | 1.26 | 0.55 | 0.22 | | 0.5 | 0 | | 0.31 | | | 0 | 0.38 | 0 | 1.11 | (D) | |
| 13 | 0.62 | 0.45 | | | 0.41 | 1.35 | 0.32 | 0.61 | | 0.42 | 0.26 | | 0.43 | | | 0.42 | 0.32 | 0.25 | 0.7 | V | F |
| 14 | 0.61 | 0.26 | | | 0.45 | 1.16 | 0.57 | 0.38 | | 0.22 | 0.26 | | 0 | | | 0.23 | 0 | 0 | 0.32 | N | |
| 15 | 0.5 | 0.49 | | | 0.29 | 1.35 | 0.59 | 0.39 | | 0.21 | 0.18 | | 0.21 | | | 0.42 | 0.58 | 0.4 | 0.69 | IL | FG |
| 16 | 0.38 | 0.24 | | | 0.29 | 0.97 | 0.36 | 0.55 | | 0.31 | 0 | | 0.32 | | | 0.2 | 0 | 0.37 | 0.58 | A | |
| 17 | 0.49 | 0.4 | | | 0.36 | 1.27 | 0.52 | 0.50 | | 0 | 0 | | 0.31 | | | 0.17 | 0.36 | | 0.97 | DL | G |
| 18 | 0 | 0.5 | | | 0.22 | 1.31 | 0.64 | 0.54 | | 0.28 | 0 | | 0 | | | 0.32 | 0.35 | | 0.75 | F | G |
| 19 | 0 | 0 | | | | | | 0.29 | | 0.15 | | | | | | 0.28 | | 0.6 | 0.6 | | |
| 20 | 0 | 0 | | | | | | | | | | | | | | | | | 0 | | |

A major fragment with a free $NH_2$ was detectable and sequenceable on the CNBr treated membrane. This fragment had the sequence:

XLLYAVDtv (SEQ ID NO:11)

By the designation "X" is meant that an unidentified amino acid was detected at that position, and therefore, "X" may represent any of the naturally occurring amino acids. Lower case letters represent less certainty in calls. A methionine (M) residue at the amino terminus of the sequence shown can be inferred due to cyanogen bromide cleavage.

EXAMPLE 39

Comparison of Amino-terminal Sequences of Specific Transfer Factors with Different Specificities Transfer factors with 3 different specificities (ovalbumin, ferritin and HSV-1) were isolated and subjected to both CNBr cleavage and N-terminal sequence analysis of the resultant peptides, as described in the above examples. The N-terminal sequences of the major CNBr fragments sequenced in Examples 34–38 are compared below in Table X. As previously described, where more than one sequence is provided for a species of transfer factor, the upper sequence represents primary amino acid calls, and different amino acids in the lower sequence represents secondary calls.

TABLE X

Summary of Amino Acid Sequences of CNBr Fragments of
Various Transfer Factors

| | | |
|---|---|---|
| Conserved: | A Q D L E D | (SEQ ID NO:1) |
| | L L Y A Q D L E D N | (SEQ ID NO:2) |
| | L L Y A Q D V E D N | (SEQ ID NO:3) |
| mFer TF-1: | X L L Y A Q D V E D N I N D E I a l f | (SEQ ID NO:4) |
| | X L L Y A Q D V E E N I N D E I a l f | (SEQ ID NO:5) |
| mOva TF-1: | X X L Y A Q D V E D N E A D | (SEQ ID NO:6) |
| | X X L Y A Q D L E D I E A K | (SEQ ID NO:7) |
| bHSV-1 TF-1: | | |
| | X L L Y A Q D L E D N T K D V K l e y | (SEQ ID NO:8) |
| | X L L Y A Q D L E D N T K D V K l e y | (SEQ ID NO:9) |
| mOva TF-2: | X L L X X Q D L E D N T T D K r a e | (SEQ ID NO:10) |
| mOva TF-3: | X L L Y A V D t v | (SEQ ID NO:11) |

•mFer TF-1 represents murine ferritin specific transfer factor-1 purified by the gel filtration system.
•mOva TF-1 represents murine ovalbumin specific transfer factor-1 purified by the gel filtration system.
•bHSV-1 TF-1 represents bovine HSV-1 specific transfer factor-1 purified by the RP-C18 TBAP system.
•mOva TF-2 represents murine ovalbumin specific transfer factor-2 purified by the RP-C18 TBAP System.
•mOva TF-3 represents murine Ovalbumin specific transfer factor-3 purified by the RP-C18 TFA System.
•Lower case letters designates less certainty in calls.

Inspection of these sequences reveals that amino acids 2 to 11, and more specifically 5 to 10, in the major CNBr fragment present in all transfer factor specificities are nearly identical, or conserved, among the different species of animals. The amino acid sequences of the CNBr fragments from the different specificities appear to be more variable after the initial 11 amino acids. The apparent increased variability in their sequences after this conserved region further suggests that unique variable regions in transfer factors with different specificities also exists.

Isolation of Specific Transfer Factors Using Different Processes Yield Identical Conserved Sequence Further inspection of the CNBr fragment sequence data reveals that a nearly identical conserved amino acid sequence is obtained upon N-terminal sequence analysis of specific transfer factors, not only with different specificities, but also isolated from different species and using different purification processes. The diagram shown in FIG. 32 summarizes these data.

EXAMPLE 40

Amplification and Isolation of Transfer Factor Coding Genetic Information

Design of Oligonucleotide Primers

Table XI shows the conserved partial amino acid sequence from cyanogen bromide treatment and Edman degradation of several purified transfer factors described above. Oligonucleotides were designed based on the codons for seven amino acids, shown underlined, within the peptide. Three oligonucleotides (SE15, SE16, and SE17) were designed and synthesized (rather than 1 oligonucleotide) due to (1) the "V/L" ambiguity at position 8 of the amino acid sequence shown, and (2) the large number of codons specified by leucine. In Table XI, differences in oligonucleotide sequences are underlined. Nucleoside residues are designated as follows:

A=adenosine; C=cytosine; G=guanosine; T=thymidine;
N=inosine; R=A or G; and Y=C or T.

TABLE XI

Conserved Amino Acid and Putative Nucleic Acid Sequences

Peptide:

| 1 | 2 | 3 | 4 | 5 | 6 | 7 | 8 | 9 | 10 | 11 |
|---|---|---|---|---|---|---|---|---|---|---|
| X | L | L | Y | A | Q | D | V/L | E | D | N |

Oligonucleotides:

SE15: TAY GCN CAR GAY G̲T̲N̲ GAR GA (SEQ ID NO:12)
SE16: TAY GCN CAR GAY C̲T̲N̲ GAR GA (SEQ ID NO:13)
SE17: TAY GCN CAR GAY T̲T̲R̲ GAR GA (SEQ ID NO:14)

RNA isolation from spleen cells

Mice were immunized against chicken ovalbumin or horse ferritin. After 2–3 weeks, RNA was isolated from spleen cells as follows. Mice were anesthetised with carbon dioxide, and quickly killed by cervical dislocation. Spleens were removed and chilled. The following procedures were all performed at 0°–4° C. Spleens were dissected (diced) and cells were washed several times in phosphate buffered saline (PBS). RNA was prepared as described by T. Clarkson in PCR: A Practical Approach, eds: M. J. McPherson, P. Quirke, and G. R. Taylor, vol. 1, p. 197.

cDNA Synthesis

Total RNA (1 μg) was first incubated in 15 μl at 70° C. for 5 min with 10 pmoles of oligonucleotide SE19 (sequence of SE19 is:

5' GTAGAAGGCAGTGATCTGCTTTTTTTTTTTT-TTT) (SEQ ID NO: 16). The reaction was shifted to 42° C. and incubated 1 hour in 25 μl with AMV reverse transcriptase (Promega) in the presence the recommended buffers and RNasin (a ribonuclease inhibitor), but without sodium pyrophosphate (FIG. 33A–D).

3'RACE (PCR)

3 μl of the cDNA synthesis reaction were amplified in a 100 μl polymerase chain reaction (PCR) (FIG. 33E–F). Taq polymerase and buffers were supplied by Promega. Magnesium chloride concentration was 2.5 mM. Oligonucleotide primers SE15, SE16, SE17 and SE18 (sequence of SE18 is: 5' GTAGAAGGCAGTGATCTGC) (SEQ ID NO:15) were 0.3 nmoles/ml. The deoxynucleoside triphosphates, dATP, dCTP, dGTP, and dTTP, were each 0.2 mM. 3 to 5 units of Taq polymerase were added to the reaction at 90° C. immediately prior to the start of the first amplification cycle. Each cycle consisted of six steps: step 1, ramping to 94° C. in 20 sec; step 2, holding at 94° C. for 60 sec; step 3, ramping to 53° C. in 60 sec; step 4, holding at 53° C. for 60 sec; step 5, ramping to 72° C. in 30 sec; step 6, holding at 72° C. for 120 sec. In steps 3 and 4, 55° or 56° C. can also be used. The use of ramping (heating and cooling) to reach the next temperature in the cycle is described by Kawasaki, E. S. in PCR Protocols, eds. M. A. Innis, D. H. Gelfand, J. J. Sninsky, and T. J. White, Academic Press, 1990, p. 21. Thirty amplification cycles were performed. A schematic depicting the cDNA synthesis and 3' RACE process is shown in FIG. 33. A 1 kbp fragment was produced when primers SE17 and SE18 were used (FIG. 34), but was not observed when SE17 was replaced with either SE15 or SE16 (FIG. 35 and Table XII). The 3' RACE protocol was originally described by Frohman, M. A., M. K. Dush, and G. R. Martin, Proc. Natl. Acad. Sci. U.S.A., (1988) 85, 8998–9002.

TABLE XII

Comparison of Probe Specific Amplifications

| Components of PCR | 1 kbp Fragment |
| --- | --- |
| Complete System* | ++ |
| Reverse Transcriptase omitted | – |
| 70° C. Annealing | – |
| Oligo SE17 omitted | – |
| Oligo SE18 (3' end adaptor) omitted | +/– |
| Oligo SE17 replaced with SE15 | – |
| Oligo SE17 replaced with SE16 | – |

*Complete System includes Oligos SE17, SE18, and reverse transcribed RNA. PCR cycle consists of denaturation at 94° C., annealing at 53–56° C., and primer extension at 72° C.

PCR of RNA extracted from mouse tissue or bovine lymphocytes

Total RNA from various mouse tissues was purchased from Ambion, Inc. (Cat #7800). Total RNA was also isolated from Ficoll-Hypaque-purified lymphocytes from the blood of a calf immunized against *Herpes simplex* virus type-1 (HSV-1). 2 µg of RNA from mouse brain, heart, kidney, liver, ovary, spleen, and thymus, and 1 µg RNA from bovine lymphocytes were used for cDNA synthesis as described above. The cDNAs were amplified by the 3' RACE PCR method described above. The results of these reactions are shown in Table XIII, which demonstrates that the appearance of a 1 kbp PCR fragment is dependent on the tissue source of the mRNA.

TABLE XIII

Comparison of Tissue Specific Amplifications

| Source of RNA | 1 kb Fragment |
| --- | --- |
| Spleen cells from: | |
| ferritin-immunized mice | ++ |
| ovalbumin-immunized mice | ++ |
| Blood Lymphocytes from HSV-1-immunized calf. | + |
| Spleen† | + |
| Thymus† | + |
| Ovary† | + |
| Brain† | –‡ |

TABLE XIII-continued

Comparison of Tissue Specific Amplifications

| Source of RNA | 1 kb Fragment |
| --- | --- |
| Heart† | – |
| Kidney† | – |
| Liver† | –# |

†Mouse RNA from these tissues was purchased from Ambion, Inc.
++Distinct 1 kbp band is observed with little or no additional bands seen
+Distinct 1 kbp band is observed along with additional bands
–No distinct 1 kbp band is observed
‡1.5 kb fragment is observed
1.2 kb fragment is observed PCR Controls Several controls were performed to demonstrate the specificity of the PCR reaction. These data are summarized in Table XII. The requirement for reverse transcriptase indicates that the PCR product is derived from RNA, not contaminating DNA. The fact that the 1 kbp fragment is made when the annealing temperature is between 53°–56° C. but not at 70° C. indicates that oligonucleotide primers are required. Clearly, SE17 is preferred, and the fact that a very faint band is seen when SE18 is omitted is undoubtedly due to the carryover of a small amount of SE19 (which can substitute for SE18) from the cDNA synthesis reaction.

1 Kirkpatrick et al., J. Immunol. 134: 1723–1727 11985)
2 Peterson et al., J. Immunol. 126: 2480–2484 (1981)
3 Burger et al., Cell Immunol. 29: 410–413 (1977)
4 U.S. Pat. No. 3,991,182 to Spitler, et al.
5 Baram et al., J. Allergy 33: 498–506 (1962)
6 Baram et al., J. Immunol. 97: 407–420 (1966)
7 Lawrence et al., J. Clin. Invest. 34: 219–232 (1955);
8 Lawrence et al., J. Exp. Med. 104: 321323 (1956)
9 Lawrence et al., Trans. Assoc. Amer. Physicians 76: 84–89 (1963)
10 Gottlieb et al., Lancet 2: 822–823 (1973)
11 U.S. Pat. No. 4,468,379 to Gottlieb, et al.
12 U.S. Pat. No. 4,616,079 to Gottlieb, et al.
13 Arala-Chaves et al., Int. Arch. Allergy 31: 353–365 (1967)
14 Neidhart et al., Cell Immunol. 9: 319–323 (1973)
15 Reymond et al., Vox sang. 29: 338–351 (1975)
16 Dunnick et al., Proc. Natl. Acad. Sci. USA 72: 4573–4576 (1975)
17 Vandenbark et al., J. Immunol. 118: 636–641 (1977)
18 Dunnick et al., J. Immunol. 118: 1944–1950 (1977)
19 Burger et al., J. Immunol. 122: 1091–1098 (1979)
20 Wilson, Trans. Assoc. Amer. Physicians 92: 239–256 (1979)
21 Borvak et al., Acta Virol. 29: 119–128 (1985)
22 U.S. Pat. No. 4,435,384 to Warren
23 U.S. Pat. No. 4,001,080 to Goust, et. al.
24 U.S. Pat. No. 4,816,563 to Wilson, et. al.
25 Kirkpatrick, J. Allergy Clin Immunol, 81:803–813, 1988
26 Borkowsky, et al.., J. Immunol. 126:486–489, 1981.
27 Kirkpatrick, "Transfer Factor" Supra. at page 808
28 European Patent Application 101,200 to Viza et al.
29 U.S. Pat. No. 4,435,384
30 Kirkpatrick et al., in Khan et al., ed., Immune Regulators In Transfer Factor pg. 547–559 (Academic Press, 1979)
31 Khan et al., Dermatologica 163: 177–185 (1981)
32 Dwyer in Kirkpatrick et al., Immunobiology of Transfer Factor pg. 233–243 (Academic Press, 1983)
33 Viza et al., Lymphokine Res 4: 27–30 (1985)
34 Steele et al., New Eng. J. Med. 303: 355–359 (1980)
35 Louie, et al., Clin. Immunol. Immunopath 44: 329–334 (1987)
36 McMeeking et al., J. Infect. Dis 161: 108–112 (1990)
37 Lopez-Bernstein et al., Arch. Intern. Med. 149:2533–2536 (1989)
38 Steele, et al. Supra
39 McMeeking et al., Supra
40 Steele, et al., Supra
41 Burnet, J. Allergy and Clin. Immuno. 54:1–13 (1974)
42 Burnet, Supra
43 Petersen et al., J. Immunol 126: 2480–2484 (1981)
44 Kirkpatrick et al., J. Immunol 134: 1723–1727 (1985)

45 Kirkpatrick et al, J. Immunol 135: 4027–4033 (1985)
46 Meyerson et al., Peptides 7: 481–489 (1986)
47 Overall, Anal. Biochem. 165: 208–214 (1987)
48 Meyerson et al., supra
49 Overall, Supra
50 Rozzo et al., Cell Immunol. 115 130–145 (1988)
51 Borkowsky et al. in Kirkpatrick et al., ed., Immunobiology of Transfer Factor pg. 91–115 (Academic Press, 1983)
52 Gottlieb, U.S. Pat. Nos. 4,616,079 and 4,468,379
53 Kirkpatrick et al. in Khan et al., ed., Immune Regulators In Transfer Factor pg. 547–559 (Academic Press, 1979)
54 Sisk et al., Journal of Virology (1994), 68:766–775.

We claim:

1. A peptide having an amino acid sequence of LLYAQDLEDN (SEQ ID NO:2).

2. A peptide having an amino acid sequence of LLYAQDVEDN (SEQ ID NO:3).

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( x i ) SEQUENCE DESCRIPTION: SEQ ID NO:1:

```
Ala  Gln  Asp  Leu  Glu  Asp
1                  5
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( x i ) SEQUENCE DESCRIPTION: SEQ ID NO:2:

```
Leu  Leu  Tyr  Ala  Gln  Asp  Leu  Glu  Asp  Asn
1                  5                        10
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( x i ) SEQUENCE DESCRIPTION: SEQ ID NO:3:

```
Leu  Leu  Tyr  Ala  Gln  Asp  Val  Glu  Asp  Asn
1                  5                        10
```

( 2 ) INFORMATION FOR SEQ ID NO:4:

( i ) SEQUENCE CHARACTERISTICS:
        ( A ) LENGTH: 19 amino acids
        ( B ) TYPE: amino acid
        ( C ) STRANDEDNESS:
        ( D ) TOPOLOGY: linear ( x i ) SEQUENCE DESCRIPTION: SEQ ID NO:4:

```
Xaa  Leu  Leu  Tyr  Ala  Gln  Asp  Val  Glu  Asp  Asn  Ile  Asn  Asp  Glu  Ile
1                  5                        10                        15

Ala  Leu  Phe
```

( 2 ) INFORMATION FOR SEQ ID NO:5:

(i) SEQUENCE CHARACTERISTICS:
  (A) LENGTH: 19 amino acids
  (B) TYPE: amino acid
  (C) STRANDEDNESS:
  (D) TOPOLOGY: linear (xi) SEQUENCE DESCRIPTION: SEQ ID NO:5:

Xaa Leu Leu Tyr Ala Gln Asp Val Glu Glu Asn Ile Asn Asp Glu Ile
1               5                   10                  15

Ala Leu Phe (2) INFORMATION FOR SEQ ID NO:6:

(i) SEQUENCE CHARACTERISTICS:
    (A) LENGTH: 14 amino acids
    (B) TYPE: amino acid
    (C) STRANDEDNESS:
    (D) TOPOLOGY: linear (xi) SEQUENCE DESCRIPTION: SEQ ID NO:6:

Xaa Xaa Leu Tyr Ala Gln Asp Val Glu Asp Asn Glu Ala Asp
1               5                   10

(2) INFORMATION FOR SEQ ID NO:7:

(i) SEQUENCE CHARACTERISTICS:
    (A) LENGTH: 14 amino acids
    (B) TYPE: amino acid
    (C) STRANDEDNESS:
    (D) TOPOLOGY: linear (xi) SEQUENCE DESCRIPTION: SEQ ID NO:7:

Xaa Xaa Leu Tyr Ala Gln Asp Leu Glu Asp Ile Glu Ala Lys
1               5                   10

(2) INFORMATION FOR SEQ ID NO:8:

(i) SEQUENCE CHARACTERISTICS:
    (A) LENGTH: 19 amino acids
    (B) TYPE: amino acid
    (C) STRANDEDNESS:
    (D) TOPOLOGY: linear (xi) SEQUENCE DESCRIPTION: SEQ ID NO:8:

Xaa Leu Leu Tyr Ala Gln Asp Leu Glu Asp Asn Thr Lys Asp Val Lys
1               5                   10                  15

Leu Glu Tyr (2) INFORMATION FOR SEQ ID NO:9:

(i) SEQUENCE CHARACTERISTICS:
    (A) LENGTH: 19 amino acids
    (B) TYPE: amino acid
    (C) STRANDEDNESS:
    (D) TOPOLOGY: linear (xi) SEQUENCE DESCRIPTION: SEQ ID NO:9:

Xaa Leu Leu Tyr Ala Gln Asp Leu Glu Asp Asn Thr Lys Asp Val Lys
1               5                   10                  15

Leu Glu Tyr (2) INFORMATION FOR SEQ ID NO:10:

(i) SEQUENCE CHARACTERISTICS:
    (A) LENGTH: 18 amino acids
    (B) TYPE: amino acid
    (C) STRANDEDNESS:

( D ) TOPOLOGY: linear ( x i ) SEQUENCE DESCRIPTION: SEQ ID NO:10:

```
Xaa Leu Leu Xaa Xaa Gln Asp Leu Glu Asp Asn Thr Thr Asp Lys Arg
1               5                   10                  15
Ala Glu
```

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:11:

```
Xaa Leu Leu Tyr Ala Val Asp Thr Val
1               5
```

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..20
        ( D ) OTHER INFORMATION: /note= "N represents Inosine"

( x i ) SEQUENCE DESCRIPTION: SEQ ID NO:12:

TAYGCNCARG AYGTNGARGA        20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..20
        ( D ) OTHER INFORMATION: /note= "N represents Inosine"

( x i ) SEQUENCE DESCRIPTION: SEQ ID NO:13:

TAYGCNCARG AYCTNGARGA        20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..20
        ( D ) OTHER INFORMATION: /note= "N represents Inosine"

( x i ) SEQUENCE DESCRIPTION: SEQ ID NO:14:

TAYGCNCARG AYTTRGARGA        20

( 2 ) INFORMATION FOR SEQ ID NO:15:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (xi) SEQUENCE DESCRIPTION: SEQ ID NO:15:

GTAGAAGGCA GTGATCTGC      19

(2) INFORMATION FOR SEQ ID NO:16:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (xi) SEQUENCE DESCRIPTION: SEQ ID NO:16:

GTAGAAGGCA GTGATCTGCT TTTTTTTTT TTTTT      35